US011738080B2

United States Patent
Emalfarb et al.

(10) Patent No.: US 11,738,080 B2
(45) Date of Patent: Aug. 29, 2023

(54) **PRODUCTION OF FLU VACCINE IN *MYCELIOPHTHORA THERMOPHILA***

(71) Applicant: DYADIC INTERNATIONAL INC., Jupiter, FL (US)

(72) Inventors: Mark Emalfarb, Jupiter, FL (US); Teunis Cornelis Verwoerd, Renkum (NL); Mark R. Alfenito, Redwood City, CA (US); Mark Baer, San Francisco, CA (US); Isabelle Legastelois, Lentilly (FR); Marie-Pierre Kazek, Brindas (FR); Marie-Clotilde Bernard, Charbonnieres les Bains (FR); Jean Dubayle, Ville sur Jarnioux (FR); Richard Kensinger, Henryville, PA (US)

(73) Assignee: DYADIC INTERNATIONAL INC., Jupiter, FL (US)

( * ) Notice: Subject to any disclaimer, the term of this patent is extended or adjusted under 35 U.S.C. 154(b) by 5 days.

(21) Appl. No.: 16/640,483

(22) PCT Filed: Aug. 9, 2018

(86) PCT No.: PCT/IB2018/056003
§ 371 (c)(1),
(2) Date: Feb. 20, 2020

(87) PCT Pub. No.: WO2019/038623
PCT Pub. Date: Feb. 28, 2019

(65) Prior Publication Data
US 2020/0215183 A1 Jul. 9, 2020

Related U.S. Application Data

(60) Provisional application No. 62/547,885, filed on Aug. 21, 2017.

(51) Int. Cl.
*A61K 39/145* (2006.01)
*C12N 1/14* (2006.01)
*A61K 39/00* (2006.01)
*C12N 7/00* (2006.01)
*C12R 1/645* (2006.01)

(52) U.S. Cl.
CPC ............ *A61K 39/145* (2013.01); *C12N 1/145* (2021.05); *A61K 2039/5256* (2013.01); *C12N 7/00* (2013.01); *C12N 2760/16251* (2013.01); *C12N 2760/18134* (2013.01); *C12R 2001/645* (2021.05)

(58) Field of Classification Search
None
See application file for complete search history.

(56) References Cited

U.S. PATENT DOCUMENTS

| 8,163,533 B2 | 4/2012 | Stuart |
| 8,268,585 B2 | 9/2012 | Emalfarb |
| 8,871,493 B2 | 10/2014 | Emalfarb |
| 9,175,296 B2 | 11/2015 | Punt |
| 2012/0107856 A1 | 5/2012 | Punt |
| 2013/0315955 A1 | 11/2013 | Holtz |
| 2015/0087028 A1* | 3/2015 | Behrouzian ............... C12P 7/10 435/99 |
| 2015/0374813 A1 | 12/2015 | Smith |

FOREIGN PATENT DOCUMENTS

| EP | 1117808 A2 | 7/2001 |
| EP | 2505651 A2 | 10/2012 |
| JP | 2004504012 A | 2/2004 |
| WO | 9532309 A1 | 11/1995 |
| WO | 0020555 A2 | 4/2000 |
| WO | 2006044796 A2 | 4/2006 |
| WO | 2008073490 A1 | 6/2008 |
| WO | 2010117786 A1 | 10/2010 |
| WO | 2010150982 A2 | 12/2010 |
| WO | 2011091376 A2 | 7/2011 |
| WO | 2014151488 A1 | 9/2014 |
| WO | 2016097369 A1 | 6/2016 |
| WO | 2017093450 A1 | 6/2017 |

OTHER PUBLICATIONS

Athmaram et al., (2011) Yeast expressed recombinant Hemagglutinin protein of novel H1N1 elicits neutralising antibodies in rabbits and mice. Virol J 8: 524; 13 pages.
Bayne et al., (2013) Vaccination against influenza with recombinant hemagglutinin expressed by *Schizochytrium* sp. confers protective immunity. PLoS One 8(4): e61790; 10 pages.
Carter et al., (2016) Design and Characterization of a Computationally Optimized Broadly Reactive Hemagglutinin Vaccine for H1N1 Influenza Viruses. J Virol 90(9): 4720-4734.
Chang et al., (2009) A novel vaccine adjuvant for recombinant flu antigens. Biologicals 37(3): 141-147.
Khurana et al., (2010) Properly folded bacterially expressed H1N1 hemagglutinin globular head and ectodomain vaccines protect ferrets against H1N1 pandemic influenza virus. PLoS One 5(7): e11548; 11 pages.
Lai and Tamm (2007) Locking the kink in the influenza hemagglutinin fusion domain structure. J Biol Chem 282(33): 23946-23956 with supplemental data.
Marin-Felix et al., (2015) A re-evaluation of the genus *Myceliophthora* (Sordariales, Ascomycota): its segregation into four genera and description of *Corynascus fumimontanus* sp. nov. Mycologia 107(3): 619-632.

(Continued)

*Primary Examiner* — Benjamin P Blumel
(74) *Attorney, Agent, or Firm* — RAPHAEL BELLUM PLLC

(57) ABSTRACT

Recombinant expression of influenza virus surface proteins in the fungus *Myceliophthora thermophila* strain C1 is provided. The recombinant proteins are for use in influenza vaccine compositions.

20 Claims, 16 Drawing Sheets

Specification includes a Sequence Listing.

(56) References Cited

OTHER PUBLICATIONS

Murugan et al., (2013) Recombinant haemagglutinin protein of highly pathogenic avian influenza A (H5N1) virus expressed in Pichia pastoris elicits a neutralizing antibody response in mice. J Virol Methods 187(1): 20-25.

Pion et al., (2014) Characterization and immunogenicity in mice of recombinant influenza haemagglutinins produced in Leishmania tarentolae. Vaccine 32(43): 5570-5576.

Santiago et al., (2012) Antigenic and immunogenic properties of recombinant hemagglutinin proteins from H1N1 A/Brisbane/59/07 and B/Florida/04/06 when produced in various protein expression systems. Vaccine. Author manuscript; available in PMC Jun. 29, 2013. 25 pages.

Steel et al., (2010) Influenza virus vaccine based on the conserved hemagglutinin stalk domain. mBio 1(1) pii: e00018-10; 9 pages.

Weldon et al., (2010) Enhanced immunogenicity of stabilized trimeric soluble influenza hemagglutinin. PLoS One 5(9). pii: e12466; 8 pages.

Legastelois et al., (2017) Non-conventional expression systems for the production of vaccine proteins and immunotherapeutic molecules. Hum Vaccin Immunother 13(4): 947-961.

Uehara Memorial Life Sciences Foundation Research Reports Collection [online], 2015, vol. 29, pp. 1-9, 139: The development of inhibitors of the influenza virus particle forming switch, [search date: Jun. 6, 2022 (in Japanese)], https://www.ueharazaidan.or.jp/houkokushu/Vol.29/pdf/139_report.pdf. English translation of introduction.

\* cited by examiner

| Construct | Strain | Expression Gla1/A | Expression HA | Remarks 1 | Remarks 2 | HA Assay |
|---|---|---|---|---|---|---|
| Pchi1-ssGla1-Gla1-Kex2-NC-Flag-Tcbh1 | D389 | +++++ | +/- | Only Gla-HA fusion product visible | | - |
| Pchi1-ssGla1-Gla1-Kex2-NC-Flag-Tcbh1 | D382 | +++++ | - | | | - |
| Pcbh1-ssGlaA-GlaA-Kex2-NC-Flag-Tcbh1 | D240 | +++++ | - | | | - |
| Pchi1-ssGlaA-GlaA-Kex2-NC-Flag-Tcbh1 | D389 | +++++ | + | Only Gla-HA fusion product visible | | - |
| Pchi1-ssGlaA-GlaA-Kex2-NC-Flag-Tcbh1 | D382 | +++++ | - | | | - |
| Pchi1-ssGlaA-GlaA-Kex2-NC-Tcbh1 | D240 | +++++ | + | Only Gla-HA fusion product visible | | - |
| Pcbh1-ssGlaA-GlaA-Kex2-NC-Tcbh1 | D389 | +++++ | ++ | Only Gla-HA fusion product visible | Mainly intracellular accumulation | - |
| Phex1-ssGlaA-GlaA-Kex2-NC-Tcbh1 | D389 | +++++ | +++ | Only Gla-HA fusion product visible | Mainly intracellular accumulation | - |
| Phex1-ssGlaA-GlaA-Kex2-NC-Tcbh1 | D240 | +++++ | + | Only Gla-HA fusion product visible | | - |

Figure 1A

| Construct | Strain | Expression | | Remarks 1 | Remarks 2 | HA Assay |
|---|---|---|---|---|---|---|
| | | Gla1/A | HA | | | |
| Pchi1-ssCbh-NC-Flag-Tcbh1 | D389 | | - | | | - |
| Pcbh1-ssCbh-NC-Flag-Tcbh1 | D240 | | - | | | - |
| Pcbh1-ssEg2-Eg2-NC-Flag-Tcbh1 | D240 | Eg2 +++ | - | | | - |
| Pcbh1-ssGlaA-GlaA-Kex2-UR-Flag-Tcbh1 | D240 | +++++ | - | | | - |
| Pchi1-ssGlaA-GlaA-Kex2-UR-Flag-Tcbh1 | D389 | +++++ | - | | | - |
| Pcbh1-ssGlaA-GlaA-Kex2-FL-Flag-Tcbh1 | D240 | +++++ | - | | | - |
| Pchi1-ssGlaA-GlaA-Kex2-FL-Flag-Tcbh1 | D389 | +++++ | - | | | - |

Figure 1B

| Construct | Strain | Expression | | Remarks 1 | Remarks 2 | HA Assay |
|---|---|---|---|---|---|---|
| | | Gla1/A | HA | | | |
| Phex1-ssGlaA-GlaA-Kex2-NC-8xG-T4 foldon-Tcbh1 | D389 | +++++ | + | Only Gla-HA fusion visible | | - |
| Phex1-ssGlaA-GlaA-Kex2-NC-TMD-Tcbh1 | D389 | +++++ | - | | Intra-cell. not checked | |
| Phex1-ssGlaA-GlaA-Kex2-5xG-NC-8xG-T4 foldon-Tcbh1 | D389 | +++++ | + | Only Gla-HA fusion visible | | - |
| Phex1-ssGlaA-GlaA-Kex2-5xG-NC-TMD-Tcbh1 | D389 | +++++ | - | | Intra-cell. not checked | |
| Phex1-ssGlaA-GlaA-Kex2-5xG-NC-Tcbh1 | D389 | +++++ | +/- | Only Gla-HA fusion visible | | - |
| Phex1-ssCbh-NC-8xG-T4 foldon-Tcbh1 | D389 | | +++ | | Extra- and intra-cellular expression | - |
| Phex1-ssCbh-NC-TMD-Tcbh1 | D389 | | +++++ | | Intra-cellular expression | +++++ |
| Phex1-ssCbh-NC-TMD-Tcbh1 | D382 | | ++++ | Much more HA0 processing than D389 | Intra-cellular expression | +++ |
| Phex1-ssCbh-NC-Tcbh1 | D389 | | ++++ | Not stable, only HA1 visible | | - |
| Phex1-ssGlaA-GlaA-Kex2-5xG-NC HA1-Tcbh1 | D389 | +++++ | + | Only Gla-HA fusion visible | | - |
| Phex1 (RI-)-ssGlaA-GlaA-Kex2-NC-Tcbh1 | D389 | +++++ | + | Only Gla-HA fusion visible | | - |

Figure 2A

| Construct | Strain | Expression Gla1/A | Expression HA | Remarks 1 | Remarks 2 | HA Assay |
|---|---|---|---|---|---|---|
| *Phex1*-ssGlaA-GlaA-Kex2-FL-8xG-T4 foldon-*Tcbh1* | D389 | +++++ | - | | | |
| *Phex1*-ssGlaA-GlaA-Kex2-FL-8xG-T4 foldon-*Tcbh1* | D382 | +++++ | - | | | |
| *Phex1*-ssGlaA-GlaA-Kex2-FL-TMD-*Tcbh1* | D389 | +++++ | - | | Intra-cell. not checked | |
| *Phex1*-ssGlaA-GlaA-Kex2-FL-TMD-*Tcbh1* | D382 | +++++ | | | Intra-cell. not checked | |
| *Phex1*-ssGlaA-GlaA-Kex2-5xG-FL-8xG-T4 foldon-*Tcbh1* | D389 | +++++ | | | | |
| *Phex1*-ssGlaA-GlaA-Kex2-5xG-FL-8xG-T4 foldon-*Tcbh1* | D382 | +++++ | | | | |
| *Phex1*-ssGlaA-GlaA-Kex2-5xG-FL-TMD-*Tcbh1* | D389 | +++++ | | | Intra-cell. not checked | |
| *Phex1*-ssGlaA-GlaA-Kex2-5xG-FL-TMD-*Tcbh1* | D382 | +++++ | | | Intra-cell. not checked | |
| *Phex1*-ssGlaA-GlaA-Kex2-5xG-FL-*Tcbh1* | D389 | +++++ | - | | | |
| *Phex1*-ssCbh-FL-*Tcbh1* | D389 | | - | | | |
| *Phex1*-ssCbh-FL-8xG-T4 foldon-*Tcbh1* | D389 | | +++++ | | Extra- and intra-cellular expression | - |
| *Phex1*-ssGlaA-GlaA-Kex2-5xG-FL (wt)-*Tcbh1* | D389 | +++++ | - | | | |

Figure 2B

Fragment 2 (5589 bps)

| Construct | Strain | Expression Gla1/A | Expression HA | Remarks 1 | Remarks 2 | HA Assay |
|---|---|---|---|---|---|---|
| Phex1-ssCbh-NC-T4 foldon-Tcbh1 | D389 | | +++ | | Intra-cellular expression | - |
| Phex1-ssCbh-NC-GCN4-Tcbh1 | D389 | | ++++ | | Intra-cellular expression | - |
| Phex1-ssCbh-FL-TMD-Tcbh1 | D389 | | ++++ | | Intra-cellular expression | ++++ |
| Phex1-ssCbh-FL-TMD-Tcbh1 | D270 | | + | | | |
| Phex1-ssCbh-NC-GGS1x-T4 foldon-Tcbh1 | D389 | | +++++ | | Extra- and intra-cellular expression | - |
| Phex1-ssCbh-NC-GGS2x-T4 foldon-Tcbh1 | D389 | | +++ | Less stable than GGS1x | Extra- and intra-cellular expression | - |
| Phex1-ssCbh-FL-TMDnc-Tcbh1 | D389 | | ++ | | Intra-cellular expression | +++ |
| Phex1-ssCbh-CA-TMD-Tcbh1 | D389 | | + | | | + |
| Phex1-ssCbh-PR8-TMD-Tcbh1 | D389 | | + | | | + |
| Phex1-ssCbh-Tex-TMD-Tcbh1 | D389 | | ++++ | | Intra-cellular expression | +++ |

Figure 3

| Construct | Strain | Expression NA | Remarks 1 | Remarks 2 |
|---|---|---|---|---|
| Phex1-NA NC full length-Tcbh1 | D389 | ++ | | Extra- and intra-cellular expression |
| Phex1-NA NC full length-Tcbh1 | D382 | ++ | | Intra-cellular expression |
| Phex1-ssCbh-NA NC VSAP-Tcbh1 | D389 | ++ | | Extra- and intra-cellular expression |
| Phex1-ssCbh-NA NC VSAP-Tcbh1 | D382 | ++ | | Extra- cellular expression |

Figure 4

Strains:

| D240 | HC strain | UV18-100f Δalp1 Δpyr5 |
|---|---|---|
| D270 | HC strain | UV18-100f Δalp1 Δpep4 Δalp2Δpyr5 |
| D389 | LC strain | W1L#100l Δchi1 Δalp1 Δalp2 Δpyr5 |
| D382 | LC strain | W1L#100l Δchi1 Δalp1 Δpyr5 |

Promoters:

| Chi1 | Chitinase 1 |
|---|---|
| Cbh1 | Cellobiohydrolase 1 |
| Hex1 | Woronin body |
| Hex1 (RI-) | Internal EcoRI site mutated |

Elements:

| kex2 | Kex2 protease site |
|---|---|
| sscbh1 | cellobiohydrolase ER signal seq. |
| Gla1 | Glucoamylase 1 (C1) |
| GlaA | Glucoamylase A (Aspergillus) |
| Flag | Flag-tag sequence |
| Eg2 | Endoglucanase 2 |
| T4 Foldon | T4 Foldon of bacteriophage |
| GCN4 | GCN4 leucine zipper (yeast) |
| VSAP | Human vasodilator stimulated phosphoprotein |

# PRODUCTION OF FLU VACCINE IN *MYCELIOPHTHORA THERMOPHILA*

FIELD OF THE INVENTION

The present invention relates to the production of recombinant influenza virus surface proteins in the fungus *Myceliophthora thermophila*. The recombinant proteins are for use in influenza vaccine compositions.

BACKGROUND OF THE INVENTION

Influenza virus is a lipid-enveloped virus with a negative-sense, single-stranded, segmented RNA genome. The envelope of the virion contains two types of surface glycoproteins, hemagglutinin and neuraminidase, which play essential roles in viral infection. The hemagglutinin (HA) mediates attachment of the virus to its host cells and viral entry by membrane fusion. The neuraminidase (NA) is an enzyme which plays important roles in the release of new progenies and the prevention of their aggregation.

Influenza viruses are classified into types A, B and C based on differences in their nucleoproteins and matrix proteins. Each type is further classified into subtypes according to combinations of HA and NA present on their surface. For influenza A viruses, 16 subtypes of HA and 9 subtypes of NA have been identified, of which three HA subtypes (H1, H2 and H3) and two NA subtypes (N1 and N2) are commonly found in humans. For influenza B viruses, only one subtype of HA and one subtype of NA are recognized.

The World Health Organization guidelines for the nomenclature of influenza virus strains are as follows: first, the type of virus is designated (A, B, or C), then the host (if non-human), place of isolation, isolation number, and year of isolation, separated by slashes. For influenza A, the HA and NA subtypes are noted in parentheses. For example, a strain often included in influenza vaccines is: A/New Caledonia/20/1999 (H1N1).

Vaccination of high-risk persons each year before the influenza season is the most effective measure for reducing the impact of influenza. The most common influenza vaccine is composed of inactivated virus particles produced using fertilized chicken eggs. Prior to each influenza season, a special committee selects three virus strains which are thought to represent the most likely viruses to strike in the coming flu season. Samples of the selected viruses are provided to manufacturers as seed virus stocks which possess the desired antigenic characteristics. The seed viruses are injected into fertilized chicken eggs. These eggs are incubated while the influenza viruses multiply. After a suitable period of time the eggs are opened and the egg white is harvested. This sample contains the viruses. The viruses are purified from the egg material and inactivated. Individual virus stocks are then combined to create the common trivalent influenza vaccine.

The production of the vaccine in eggs is associated with a number of drawbacks. First, a huge number of eggs is required, as high as 1-2 eggs/dose. In addition, the production is time consuming, expensive and lacks flexibility, for example if changes in the vaccine composition are needed during the flu season. Also, production in eggs results in varying viral yields and is also associated with allergic reactions to egg protein.

To avoid the use of eggs, alternative methods for producing influenza viruses have been proposed. These include production of virus particles by propagating the virus in mammalian cell cultures, for example in MDCK cells (Novartis) or PERC.6 cells (Crucell). In addition, production of recombinant hemagglutinin and/or neuraminidase proteins has been suggested, for example in insect cells using a baculovirus expression vector (Flublok®, Protein Sciences Corp.), in plant cells (Medicago Inc.), in bacterial systems (VaxInnate) and in fungi such as *Neurospora crassa* (Intrexon/Neugenesis) and *Pichia pastoris* (see for example, Murugan et al., 2013, *Journal of Virological Methods*, 187:20-25). However, hitherto described methods are relatively expensive and/or their yield is relatively low.

U.S. Pat. No. 8,163,533 discloses methods and compositions for rapidly producing multivalent recombinant vaccines using filamentous fungal heterokaryons. Filamentous fungal heterokaryons are generated from combinations of two or more parent strains into which recombinant DNA molecules encoding variants of antigens derived from pathogenic organisms have been introduced. The resulting vaccines are multivalent.

WO 2014/151488 discloses methods of improving the stability and maintaining the potency of recombinant hemagglutinin formulations, in particular, recombinant influenza hemagglutinin (rHA). In particular, it was shown that the stability of rHA formulations may be significantly improved by mutating cysteine residues or by formulating with a reducing agent and sodium citrate.

*Myceliophthora thermophila* strain C1, previously named *Chrysosporium lucknowense* strain C1, is a filamentous thermophilic fungus discovered in the early 1990's. The wild type C1 naturally produces high levels of cellulases, which made it attractive for production of these enzymes on a commercial scale. Over the years expression systems and several improved strains of C1 have been developed for producing additional enzymes and other industrial proteins in C1. For example, improved C1 strains characterized by cellulase production at higher levels compared to the wild type C1 isolate have been developed, denoted "High Cellulase" or "HC". In addition, C1 strains which produce low levels of cellulases have also been developed, denoted "Low Cellulase" or "LC", enabling the commercial production of purer enzymes.

Wild type C1 was deposited in accordance with the Budapest Treaty with the number VKM F-3500 D, deposit date Aug. 29, 1996. HC and LC strains have also been deposited, for example: strain UV13-6, deposit no. VKM F-3632 D, strain NG7C-19, deposit no. VKM F-3633 D, strain UV18-25, deposit no. VKM F-3631 D. Additional improved C1 strains that have been deposited include (i) HC strain UV18-100f (Δalp1Δpyr5)—deposit no. CBS141147; (ii) HC strain UV18-100f (Δalp1Δpep4Δalp2Δpyr5,Δprt1) deposit no. CBS141143; (iii) LC strain W1L #100I (Δchi1Δalp1Δalp2Δpyr5)—deposit no. CBS141153; and (iv) LC strain W1L #100I (Δchi1Δalp1Δpyr5)—deposit no. CBS141149.

U.S. Pat. Nos. 8,268,585 and 8,871,493 disclose a transformation system in the field of filamentous fungal hosts for expressing and secreting heterologous proteins or polypeptides. Also disclosed is a process for producing large amounts of polypeptide or protein in an economical manner. The system comprises a transformed or transfected fungal strain of the genus *Chrysosporium*, more particularly of *Chrysosporium lucknowense* and mutants or derivatives thereof. Also disclosed are transformants containing *Chrysosporium* coding sequences, as well expression-regulating sequences of *Chrysosporium* genes.

U.S. Pat. No. 9,175,296 discloses a fungal host strain of *Chrysosporium lucknowense*. Also disclosed is a method for homologous and/or heterologous production of a pure protein with a purity of higher than 75%, a method for production of artificial protein mixes and a method for simplified screening of strains functionally expressing a desired enzyme. U.S. Pat. No. 9,175,296 further discloses an isolated promoter sequence suitable for the transcriptional control of gene expression in *Chrysosporium lucknowense* and a method for isolating a fungal host strain of *Chrysosporium lucknowense* wherein the protease secretion is less than 20% of the protease secretion of *Chrysosporium lucknowense* strain UV 18-25.

There is a need for improved methods for producing influenza vaccine compositions, which are cost effective and which provide high yields of effective immunogenic proteins in a time-constrained manner that meets the production requirements of a seasonal influenza vaccine.

SUMMARY OF THE INVENTION

The present invention provides according to some aspects *Myceliophthora thermophila* strain C1 genetically modified to produce the influenza virus surface proteins hemagglutinin and neuraminidase.

As disclosed herein, the influenza virus surface proteins are produced as full length membrane-bound proteins, containing both their ectodomain and transmembrane domain. It was surprisingly found that the full-length membrane-bound form produced by C1 is functional and immunogenic, while modified secreted forms are inactive. The membrane-bound form was particularly effective and elicited an immune response at relatively low concentrations, as exemplified in a mouse model. Advantageously, C1 could produce the membrane-bound form at high yields, suitable for commercial-scale production.

The present invention therefore provides an efficient system for producing effective immunogenic influenza virus proteins at high yields, for use in influenza vaccine compositions.

According to one aspect, the present invention provides a *Myceliophthora thermophila* C1 genetically-modified to produce an influenza virus surface protein, comprising an expression construct comprising a nucleic acid sequence encoding the influenza virus surface protein operably linked to at least one C1 regulatory sequence, wherein the influenza virus surface protein comprises its ectodomain and transmembrane domain and is expressed in the C1 as a membrane-bound protein.

In some embodiments, the influenza virus surface protein is hemagglutinin (HA). According to these embodiments, the expression construct further comprises a nucleic acid sequence encoding a C1 signal peptide linked in-frame to the nucleic acid sequence encoding the HA.

In some embodiments, the HA subtype is selected from the group consisting of influenza A-H1, H2, H3, H4, H5, H6, H7, H8, H9, H10, H11, H12, H13, H14, H15 and H16; and influenza B subtype.

In some particular embodiments, the HA subtype is a subtype infecting humans selected from influenza A subtypes H1, H2 and H3; and influenza B subtype. Each possibility represents a separate embodiment of the present invention.

In some embodiments, the HA is from an influenza virus strain selected from the group consisting of A/New Caledonia/20/99 (H1N1), A/California/04/2009 (H1N1), A/Uruguay/716/07 (H3N2) (A/Brisbane/10/07-like), B/Florida/04/2006: B Yamagata lineage, A/Puerto Rico/08/1934 (H1N1), and A/Texas/50/2012 (H3N2).

In some embodiments, the at least one C1 regulatory sequence comprises a C1 promoter. In some embodiments, the C1 promoter is selected from the group consisting of: hex1 (Woronin body), cbh1 (cellobiohydrolase 1) and chi1 (chitinase 1) promoters. Each possibility represents a separate embodiment of the present invention. In some particular embodiments, the C1 promoter is hex1 promoter.

In some embodiments, the C1 signal peptide is a signal peptide derived from a protein selected from the group consisting of Cbh1 (Cellobiohydrolase 1, C1), Gla1 (Glucoamylase 1, C1) and GlaA (Glucoamylase A, *Aspergillus*). Each possibility represents a separate embodiment of the present invention. In some particular embodiments, the C1 signal peptide is derived from Cbh1.

In some embodiments, the expression construct comprises: hex1 promoter operably linked to a nucleic acid sequence encoding a Cbh1 signal peptide fused to HA. According to these embodiments, the HA is from an influenza virus strain selected from the group consisting of A/New Caledonia/20/99 (H1N1), A/California/04/2009 (H1N1), B/Florida/04/2006: B Yamagata lineage, A/Puerto Rico/08/1934 (H1N1), and A/Texas/50/2012 (H3N2).

In some embodiments, the influenza virus surface protein is a neuraminidase (NA).

In some embodiments, the NA subtype is selected from the group consisting of influenza A-N1, N2, N3, N4, N5, N6, N7, N8 and N9; and influenza B subtype.

In some particular embodiments, the NA subtype is a subtype infecting humans selected from influenza A subtypes N1 and N2; and influenza B subtype. Each possibility represents a separate embodiment of the present invention.

In some embodiments, the expression construct comprises: hex1 promoter operably linked to a nucleic acid sequence encoding NA. According to these embodiments, the NA is from the influenza virus strain A/New Caledonia/20/99 (H1N1).

In some embodiments, the C1 strain is selected from the group consisting of: W1L #100I (prt-Δalp1Δchi1Δalp2Δpyr5) deposit no. CBS141153, UV18-100f (prt-Δalp1, Δpyr5) deposit no. CBS141147, W1L #100I (prt-Δalp1Δchi1Δpyr5) deposit no. CBS141149, and UV18-100f (prt-Δalp1Δpep4Δalp2,Δprt1Δpyr5) deposit no. CBS141143. In some particular embodiments, the C1 strain is W1L #100I (prt-Δalp1Δchi1Δalp2Δpyr5) deposit no. CBS141153. In additional particular embodiments, the C1 strain is UV18-100f (prt-Δalp1, Δpyr5) deposit no. CBS141147.

In some embodiments, the C1 strain is a strain mutated to delete one or more genes encoding an endogenous protease. In some embodiments, the C1 strain is a strain mutated to delete a gene encoding an endogenous chitinase.

According to a further aspect, the present invention provides a method for producing an influenza virus surface protein, the method comprising culturing the genetically-modified *Myceliophthora thermophila* C1 of the present invention under conditions suitable for expressing the influenza virus surface protein; and recovering the influenza virus surface protein.

In some embodiments, recovering the influenza virus surface protein comprises extraction from mycelia.

In some embodiments, the yield of the recovered protein is at least 80%. According to certain exemplary embodiments, the yield is 80%.

According to another aspect, there is provided herein an expression construct for expressing a membrane bound influenza virus surface protein in *Myceliophthora thermophila* C1, the expression construct comprising at least one C1 regulatory sequence operably linked to a nucleic acid sequence encoding an influenza virus surface protein, wherein the influenza virus surface protein comprises its ectodomain and transmembrane domain.

According to yet another aspect, there is provided herein a substantially pure, recombinant influenza virus surface protein produced by the modified *Myceliophthora thermophila* C1 of the present invention, wherein the influenza virus surface protein is purified to 95% purity or greater and is active and immunogenic, and induces a protective immune response when used as a vaccine.

Further provided herein is an influenza vaccine composition comprising an influenza virus surface protein produced the modified *Myceliophthora thermophila* C1 of the present invention.

These and further aspects and features of the present invention will become apparent from the detailed description, examples and claims which follow.

BRIEF DESCRIPTION OF THE FIGURES

FIGS. 1A-1B. Expression constructs designed and tested. Hemagglutinin (HA), first series. P=promoter, ss=signal sequence, T=terminator. The HA type included in each construct is marked in boldface.

FIGS. 2A-2B. Expression constructs designed and tested. Hemagglutinin (HA), second series. P=promoter, ss=signal sequence, T=terminator. The HA type included in each construct is marked in boldface.

FIG. 3. Expression constructs designed and tested. Hemagglutinin (HA), third series. P=promoter, ss=signal sequence, T=terminator. The HA type included in each construct is marked in boldface.

FIG. 4. Expression constructs designed and tested, neuraminidase (NA). P=promoter, ss=signal sequence, T=terminator. The NA included in each construct is marked in boldface.

FIG. 5. List of abbreviations.

FIGS. 10A-10B. Antibody responses elicited against A/New Caledonia/20/99 (H1N1) produced in C1 on Day 27 (FIG. 10A) and D49 (FIG. 10B) following injection to mice.

DETAILED DESCRIPTION OF THE INVENTION

Figure 2C:
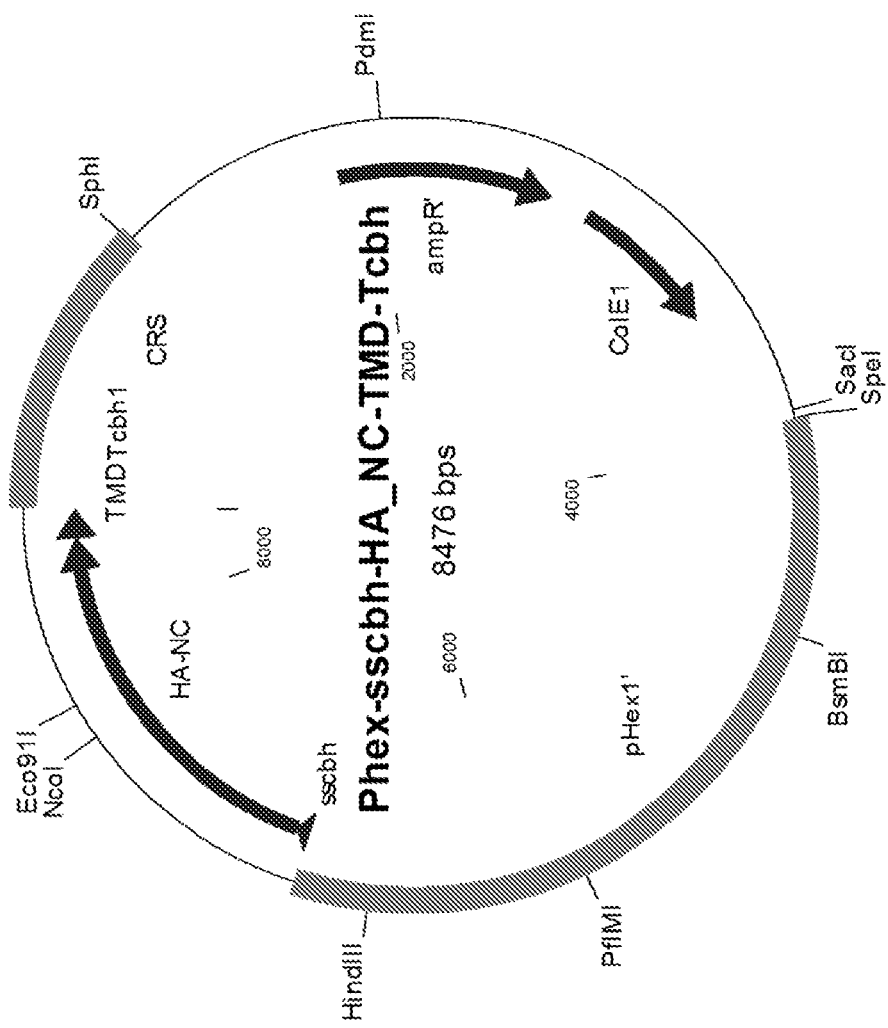
FIG. 2C. Illustration of an expression vector containing the construct Phex1-ssCbh-NC-TMD-Tcbh1.

The present invention is directed to recombinant expression of influenza virus surface proteins in the fungus *Myceliophthora thermophila*, particularly in the strain C1. The present invention provides according to some embodiments genetically modified C1 cells expressing influenza virus surface proteins, and methods for producing an influenza vaccine composition using the same.

It is now disclosed that influenza antigens produced in C1 generate an equal, or even better, immune response in mice than the industry standard antigens.

As used herein "C1" or "*Myceliophthora thermophila* C1" refers to *Myceliophthora thermophila* strain C1, previously named *Chrysosporium lucknowense* strain C1 deposited in accordance with the Budapest Treaty with the number VKM F-3500 D, deposit date Aug. 29, 1996. The terms also encompass genetically modified sub-strains thereof which have been mutated, for example, to delete one or more endogenous genes. For example, the C1 strain (sub-strain) may be a strain mutated to delete one or more genes encoding an endogenous protease and/or one or more genes encoding an endogenous chitinase. For example, C1 strains which are encompassed by the present invention include W1L #100I (prt-Δalp1Δchi1Δalp2Δpyr5) deposit no. CBS141153, UV18-100f (prt-Δalp1, Δpyr5) deposit no. CBS141147, W1L #100I (prt-Δalp1Δchi1Δpyr5) deposit no. CBS141149, and UV18-100f (prt-Δalp1Δpep4Δalp2, Δprt1Δpyr5) deposit no. CBS141143.

It is noted that a recent paper (Marin-Felix et al., 2015, *Mycologica*, 3:619-63) proposed the splitting of the *Myceliophthora* genus based on several criteria such as temperature growth, sexual morph in culture and conidia properties. According to the proposed criteria C1 belongs to the genus *Thermothelomyces* species heterothallical thermophila. Thus, according to the Marin-Felix paper, C1 updated name is *Thermothelomyces thermophila* strain C1.

Expression Constructs

The terms "expression construct", "DNA construct" or "expression cassette" are used herein interchangeably and refer to an artificially assembled or isolated nucleic acid molecule which includes a nucleic acid sequence encoding a protein of interest and which is assembled such that the protein of interest is expressed in a target host cell. An expression construct typically comprises appropriate regulatory sequences operably linked to the nucleic acid sequence encoding the protein of interest. An expression construct may further include a nucleic acid sequence encoding a selection marker.

The terms "nucleic acid sequence", "nucleotide sequence" and "polynucleotide" are used herein to refer to polymers of deoxyribonucleotides (DNA), ribonucleotides (RNA), and modified forms thereof in the form of a separate fragment or as a component of a larger construct. A nucleic acid sequence may be a coding sequence, i.e., a sequence that encodes for an end product in the cell, such as a protein. A nucleic acid sequence may also be a regulatory sequence, such as, for example, a promoter.

The terms "peptide", "polypeptide" and "protein" are used herein to refer to a polymer of amino acid residues. The term "peptide" typically indicates an amino acid sequence consisting of 2 to 50 amino acids, while "protein" indicates an amino acid sequence consisting of more than 50 amino acid residues.

A sequence (such as, nucleic acid sequence and amino acid sequence) that is "homologous" to a reference sequence refers herein to percent identity between the sequences, where the percent identity is at least 70%, preferably at least 80%, at least 85%, at least 90%, at least 95%, at least 98% or at least 99%. Each possibility represents a separate embodiment of the present invention. Homologous nucleic acid sequences include variations related to codon usage and degeneration of the genetic code.

Sequence identity may be determined using a nucleotide/amino acid sequence comparison algorithms, as known in the art.

The term "regulatory sequences" refer to DNA sequences which control the expression (transcription) of coding sequences, such as promoters and terminators.

The term "promoter" is directed to a regulatory DNA sequence which controls or directs the transcription of another DNA sequence in vivo or in vitro. Usually, the promoter is located in the 5' region (that is, precedes, located upstream) of the transcribed sequence. Promoters may be derived in their entirety from a native source, or be composed of different elements derived from different promoters found in nature, or even comprise synthetic nucleotide segments. Promoters can be constitutive (i.e. promoter activation is not regulated by an inducing agent and hence rate of transcription is constant), or inducible (i.e., promoter activation is regulated by an inducing agent). In most cases the exact boundaries of regulatory sequences have not been completely defined, and in some cases cannot be completely defined, and thus DNA sequences of some variation may have identical promoter activity.

The term "terminator" is directed to another regulatory DNA sequence which regulates transcription termination. A terminator sequence is operably linked to the 3' terminus of the nucleic acid sequence to be transcribed.

The terms "C1 promoter" and "C1 terminator" indicate promoter and terminator sequences suitable for use in C1, i.e., capable of directing gene expression in C1. According to some embodiments, the C1 promoter/terminator is derived from an endogenous gene of *Myceliophthora thermophila* C1. For example, in some embodiments, the C1 promoter is hex1 (Woronin body) promoter. An exemplary hex1 promoter sequence is set forth as SEQ ID NO: 1. In additional embodiments, the C1 promoter is chi1 (chitinase 1) promoter. An exemplary chi1 promoter sequence is set forth as SEQ ID NO: 2.

According to some embodiments the C1 promoter/terminator is derived from a gene exogenous to *Myceliophthora thermophila* C1. For example, bgl promoter may be used.

The term "operably linked" means that a selected nucleic acid sequence is in proximity with a regulatory element (promoter or terminator) to allow the regulatory element to regulate expression of the selected nucleic acid sequence.

The term "signal peptide" or "signal sequence" are used herein interchangeably and refer to a short peptide (usually 5-30 amino acids long) typically present at the N-terminus of a newly synthesized polypeptide chain that directs the protein to the secretory pathway in the host cell. The signal peptide is typically subsequently removed. A "C1 signal peptide" indicates a signal peptide suitable for use with C1, i.e., capable of directing proteins expressed in C1 into the secretory pathway of C1. According to some embodiments, the C1 signal peptide is derived from an endogenous gene of *Myceliophthora thermophila* C1. For example, in some embodiments, the C1 signal peptide is a signal peptide derived from Gla1 (Glucoamylase 1, C1). An exemplary sequence encoding Gla1 signal peptide is set forth in positions 1-20 of SEQ ID NO: 23. In additional embodiments, the C1 signal peptide is a signal peptide derived from Cbh1 (Cellobiohydrolase 1, C1). An exemplary sequence encoding Cbh1 signal peptide is set forth as SEQ ID NO: 3.

According to some embodiments the C1 signal peptide is derived from a gene exogenous to *Myceliophthora thermophila* C1. For example, in some embodiments, the C1 signal peptide is derived from GlaA (Glucoamylase A, *Aspergillus*). An exemplary sequence encoding GlaA signal peptide is set forth in positions 1-18 of SEQ ID NO: 24.

As used herein, the term "in frame", when referring to one or more nucleic acid sequences, indicates that these sequences are linked such that their correct reading frame is preserved.

Expression constructs according to some embodiments of the present invention comprise a C1 promoter sequence and a C1 terminator sequence operably linked to a nucleic acid sequence encoding a C1 signal peptide and an influenza virus surface protein fused in-frame.

In some embodiments, the expression construct does not contain a nucleic acid sequence encoding a carrier protein fused to the influenza virus surface protein and facilitating secretion thereof.

A particular expression construct may be assembled by a variety of different methods, including conventional molecular biological methods such as polymerase chain reaction (PCR), restriction endonuclease digestion, in vitro and in vivo assembly methods, as well as gene synthesis methods, or a combination thereof.

Influenza Virus Surface Proteins

Hemagglutinin, abbreviated "HA", is a type I membrane glycoprotein that mediates attachment of the virus to its host cells via sialic acid-containing receptors on the host cells. The HA molecule is present in the virus as a homotrimer. Each monomer generally comprises two domains, termed HA1 and HA2, where the HA2 domain comprises a transmembrane region, which connects the HA protein to the viral membrane, and a small cytoplasmic tail. The monomer is synthesized as a 75 kDa precursor protein, termed HA0, which assembles at the virus's surface into a trimeric protein. A signal peptide directs the HA0 into the host cell's secretory pathway and is not present in the mature protein. In order to be active, the HA0 precursor must be cleaved by cellular proteases of the host. After cleavage, two subunits corresponding to the HA1 and HA2 domains are generated, linked by a disulfide bond (and anchored to the virus's surface).

Unless defined otherwise, the term "hemagglutinin" or "HA" as used herein refers to influenza virus hemagglutinin, particularly to the full-length protein containing the ectodomain that extends outside the virus particle, the transmembrane domain and the cytoplasmic tail. The term encompasses the HA0 uncleaved form as well as the mature HA1+HA2 form.

The subtype of the HA of the present invention may be influenza A subtype H1, H2, H3, H4, H5, H6, H7, H8, H9, H10, H11, H12, H13, H14, H15 or H16. The HA subtype may also be influenza B subtype. In particular embodiments, the HA subtype is a subtype infecting humans. In some embodiments, the HA subtype is selected from influenza A subtypes H1, H2 and H3. In additional particular embodiments, the HA subtype is influenza B subtype.

Neuraminidase, abbreviated "NA", is a type II membrane-bound enzyme that mediates the release of new viral progenies from a host cell. It is present on the viral surface as a tetramer of four identical monomers, each generally comprising a cytoplasmic domain, a transmembrane domain, a stalk domain, and a globular head domain that carries the enzymatically active site. Unless defined otherwise, the term "neuraminidase" or "NA" as used herein refers to the full length protein.

The subtype of the NA of the present invention may be influenza A subtype N1, N2, N3, N4, N5, N6, N7, N8 or N9, or influenza B subtype. In particular embodiments, the NA subtype is a subtype infecting humans. In some embodiments, the NA subtype is selected from influenza A subtypes N1 and N2. In additional particular embodiments, the NA subtype is influenza B subtype.

Nucleotide and protein sequences of HA and NA from various influenza virus strains are publicly available, for example, at the database of the National Center for Biotechnology Information (NCBI). Exemplary sequences for HA and NA genes/proteins include those from influenza strains A/New Caledonia /20/99 (H1N1), A/California/04/2009 (H1 N1), A/Uruguay/716/07 (H3N2) (A/Brisbane/10/07-like), B/Florida/04/2006: B Yamagata lineage, A/Puerto Rico/08/ 1934 (H1N1), and A/Texas/50/2012 (H3N2). Each possibility represents a separate embodiment of the present invention.

Genetically-modified variants of HA and NA may also be engineered into C1 according to the present invention, such as variants denoted "universal" HA and NA. Universal HA and NA are cross-reactive antigens that stimulate protection against multiple influenza strains, as described, for example, in Carter et al. (2016) *Design and Characterization of a Computationally Optimized Broadly Reactive Hemagglutinin Vaccine for H1N1 Influenza Viruses*, J Virol. 90(9). 4720-34.

The influenza virus surface proteins are cloned and expressed according to the present invention as membrane-bound proteins comprising their ectodomain and transmembrane domain. The cloned HA/NA genes of the present invention are typically modified by replacement of the natural signal peptide with a C1 signal peptide.

In some embodiments, the HA is from the influenza virus strain A/New Caledonia/20/99 (H1N1) ("HA New Caledonia"). The amino acid sequence of HA New Caledonia with its transmembrane domain, without the natural signal peptide, is set forth as SEQ ID NO: 4. A nucleotide sequence encoding the HA New Caledonia with its transmembrane domain, without the natural signal peptide, is set forth as SEQ ID NO: 5.

In some embodiments, the HA is from the influenza virus strain A/Texas/50/2012 (H3N2) ("HA Texas"). The amino acid sequence of HA Texas with its transmembrane domain, without the natural signal peptide, is set forth as SEQ ID NO: 6. A nucleotide sequence encoding the HA Texas with its transmembrane domain, without the natural signal peptide, is set forth as SEQ ID NO: 7.

In some embodiments, the HA is from the influenza virus strain A/Puerto Rico/08/1934 (H1N1) ("HA Puerto Rico"). The amino acid sequence of HA Puerto Rico with its transmembrane domain, without the natural signal peptide, is set forth as SEQ ID NO: 8. A nucleotide sequence encoding the HA Puerto Rico with its transmembrane domain, without the natural signal peptide, is set forth as SEQ ID NO: 9.

In some embodiments, the HA is from the influenza virus strain B/Florida/04/2006: B Yamagata lineage ("HA Florida"). The amino acid sequence of HA Florida with its transmembrane domain, without the natural signal peptide, is set forth as SEQ ID NO: 10. A nucleotide sequence encoding the HA Florida with its transmembrane domain, without the natural signal peptide, is set forth as SEQ ID NO: 11.

In some embodiments, the HA is from the influenza virus strain A/California/04/2009 (H1N1) ("HA California"). The amino acid sequence of HA California with its transmembrane domain, without the natural signal peptide, is set forth as SEQ ID NO: 12. A nucleotide sequence encoding the HA California with its transmembrane domain, without the natural signal peptide, is set forth as SEQ ID NO: 13.

In some embodiments, the NA is from the influenza virus strain A/New Caledonia/20/99 (H1N1) ("NA New Caledonia"). The amino acid sequence of NA New Caledonia, full length, is set forth as SEQ ID NO: 14. A nucleotide sequence encoding the NA New Caledonia, full length, is set forth as SEQ ID NO: 15.

For expression in C1, the cloned HA/NA genes are preferably codon optimized for C1 expression, meaning that the cloned genes are designed based on the amino acid sequence of an influenza virus surface protein of interest, employing the codon usage of C1.

According to certain exemplary embodiments, the genes are cloned under a C1 promoter and a C1 terminator.

An exemplary expression construct encoding HA New Caledonia with its transmembrane domain under hex1 promoter and cbh1 terminator, with a Cbh signal sequence, is set forth as SEQ ID NO: 16. The sequence encoding the HA corresponds to positions 2920-4563 of SEQ ID NO: 16. This segment may be replaced by a nucleotide sequence encoding a different HA protein or an NA protein, to obtain an expression construct encoding a different HA protein or an NA protein.

An exemplary expression vector comprising the expression construct set forth as SEQ ID NO: 16 is set forth as SEQ ID NO: 17 and illustrated in FIG. 2C.

Genetically-Engineered C1

C1 cells genetically engineered to produce influenza virus surface proteins according to the present invention are generated by introducing into C1 cells, particularly into the nucleus of C1 cells, an expression construct comprising a nucleic acid encoding an influenza virus surface protein, as described above. In particular, the genetic modification according to the present invention means incorporation of the expression construct to the host genome.

In some embodiments, C1 is genetically-engineered to produce a single influenza virus protein. In other embodiments, C1 is genetically-engineered to produce a plurality of different influenza virus proteins. A "plurality" indicates at least two.

Introduction of an expression construct into C1 cells, i.e., transformation of C1, can be performed by methods known in the art for transforming filamentous fungi. For example, transformation can be performed using the protoplast transformation method as known in the art and also described in the Examples section below.

To facilitate easy selection of transformed cells, a selection marker may be transformed into the C1 cells. A "selection marker" indicates a polynucleotide encoding a gene product conferring a specific type of phenotype that is not present in non-transformed cells, such as an antibiotic resistance (resistance markers), ability to utilize a certain resource (utilization/auxotrophic markers) or expression of a reporter protein that can be detected, e.g. by spectral measurements. Auxotrophic markers are typically preferred as a means of selection in the food or pharmaceutical industry. The selection marker can be on a separate polynucleotide co-transformed with the expression construct, or on the same polynucleotide of the expression construct.

Following transformation, positive transformants are selected by culturing the C1 cells on e.g., selective media according to the chosen selection marker.

Expression of the protein of interest can be detected using standard methods. The detection may be performed by detecting the protein itself, e.g., by various types of staining or by an immunological method, or by detecting its activity, e.g., by a hemagglutination assay. Prior to detection, the protein may be separated using a variety of techniques, such as SDS-PAGE. Exemplary procedures are described in the Examples section below.

Best producers are selected and applied in fermentations to produce high amount of the desired gene product.

Production of Proteins

To produce the protein, the genetically modified C1 cells are cultured under conditions that permit the expression of the nucleic acid encoding the influenza virus surface protein. Exemplary culturing conditions for shake-flask and stirred-tank fermentations are detailed in the Examples section below.

Vaccine Compositions

A vaccine or an immunogenic composition according to the present invention comprises an influenza virus surface protein produced as described above and a pharmaceutically acceptable carrier.

The term "immunogenicity" or "immunogenic" relates to the ability of a substance to stimulate or elicit an immune response. Immunogenicity is measured, for example, by determining the presence of antibodies specific for the substance after challenging an immunologically competent organism with the substance. The presence of antibodies specific to the substance and their quantity is detected by methods known in the art, for example using an ELISA assay.

In some embodiments, the vaccine is formulated in an immunizing dosage form including purified HA proteins derived from three strains of influenza virus recommended by the FDA for a particular influenza season. Functional immunity can be measured using assays that quantify antibodies that bind to influenza hemagglutinin, that block the ability of influenza virus to agglutinate red blood cells, or that neutralize the influenza virus. Protective immune responses with recombinant HA vaccines can also be measured in animals that are susceptible to influenza infection or in human challenge studies.

The vaccines of the present invention comprise recombinant HA and/or NA proteins, and optionally, an adjuvant. As exemplified hereinbelow, it was surprisingly found that a recombinant HA protein produced in C1 according to the present invention elicited a humoral response in mice even when administered without an adjuvant.

The vaccine can be formulated for administration in one of many different modes, including via intramuscular, intranasal, intradermal, oral, intraperitoneal, subcutaneous or transdermal mode of administration In some embodiments, the vaccine is formulated for parenteral administration. In some particular embodiments, the vaccine is formulated for intramuscular administration. In other particular embodiments, the vaccine is formulated for intradermal administration.

In additional particular embodiments, the vaccine is formulated for mucosal delivery, in particular intranasal delivery.

The vaccine composition can contain a variety of excipients, including stabilizers, buffers, or preservatives.

According to some embodiments, the vaccine compositions according to the present invention do not contain an adjuvant.

In some applications a pharmaceutically acceptable adjuvant may be included in the vaccine formulation. The choice of the adjuvant is determined in part by the mode of administration of the vaccine.

Non-limiting examples of intranasal adjuvants include chitosan powder, PLA and PLG microspheres, QS-21, calcium phosphate nanoparticles (CAP) and mCTA/LTB (mutant cholera toxin E112K with pentameric B subunit of heat labile enterotoxin).

Examples of adjuvants for other modes of administration include inorganic adjuvants in gel form (aluminium hydroxide/aluminium phosphate), calcium phosphate, bacterial adjuvants such as monophosphoryl lipid A and muramyl peptides, particulate adjuvants such as ISCOMS ("immunostimulatory complexes"), liposomes and biodegradable microspheres, adjuvants based on oil emulsions and emulsifiers such as IFA ("Incomplete Freund's adjuvant"), SAF ("Syntex Adjuvant Formulation"), saponins (such as QS-21), squalene/squalane, synthetic adjuvants such as non-ionic block copolymers, muramyl peptide analogs, synthetic lipid A, synthetic polynucleotides and polycationic adjuvants.

Adjuvants are utilized in an adjuvant amount, which can vary with the adjuvant, host animal and immunogen. Typical amounts can vary from about 1 microgram to about 1 mg per immunization. Those skilled in the art know that appropriate concentrations or amounts can be readily determined.

List of Sequences

| Element | SEQ ID NO: | Remarks |
|---|---|---|
| Phex1 (promoter) | 1 | |
| Pchi1 (promoter) | 2 | |
| ssCbh (signal sequence Cbh), nucleotide sequence | 3 | |
| HA New Caledonia with TMD, without ss, amino acid sequence | 4 | TMD corresponds to positions 512-548 of SEQ ID NO: 4. |
| HA New Caledonia with TMD, without ss, nucleotide sequence | 5 | Sequence encoding TMD corresponds to positions 1533-1644 of SEQ ID NO: 5. 'Stop' codon is omitted. |
| HA Texas with TMD, without ss, amino acid sequence | 6 | |
| HA Texas with TMD, without ss, nucleotide sequence | 7 | 'Stop' codon is omitted. |
| HA Puerto Rico with TMD, without ss, amino acid sequence | 8 | |
| HA Puerto Rico with TMD, without ss, nucleotide sequence | 9 | |
| HA Florida with TMD, without ss, amino acid sequence | 10 | TMD corresponds to positions 538-569 of SEQ ID NO: 10. |
| HA Florida with TMD, without ss, nucleotide sequence | 11 | Sequence encoding TMD corresponds to positions 1612-1707 of SEQ ID NO: [—]. 'Stop' codon is omitted. |
| HA California with TMD, without ss, amino acid sequence | 12 | |

| Element | SEQ ID NO: | Remarks |
|---|---|---|
| HA California with TMD, without ss, nucleotide sequence | 13 | |
| Neuraminidase (NA) New Caledonia full length amino acid sequence | 14 | |
| Neuraminidase (NA) New Caledonia full length nucleotide sequence | 15 | 'Stop' codon omitted |
| Phex1-ssCbh-NC-TMD-Tcbh1 | 16 | Construct used for transformation |
| Phex1-ssCbh-NC-TMD-Tcbh1 - complete vector sequence | 17 | |
| Phex1-ssCbh-NC-8G-T4 foldon amino acid sequence without ss | 18 | |
| Phex1-ssCbh-NC-8G-T4 foldon nucleotide sequence including ss | 19 | |
| Phex1-ssCbh-FL-8G-T4 foldon amino acid sequence without ss | 20 | |
| Phex1-ssCbh-FL-8G-T4 foldon nucleotide sequence including ss | 21 | |
| Phex1-ssCbh-NA NC VSAP-Tcbh1 amino acid sequence | 22 | Signal sequence corresponds to positions 1-17 of SEQ ID NO: 22; VSAP domain (tetramerization domain) corresponds to positions 18-59 of SEQ ID NO: 22; and NA ecto-domain corresponds to positions 62-449 of SEQ ID NO: 22. |
| Gla1 from C1, including ss, amino acid sequence | 23 | Signal sequence corresponds to positions 1-20 of SEQ ID NO: 23 |
| GlaA from *Aspergillus niger* including ss amino acid sequence | 24 | Signal sequence corresponds to positions 1-18 of SEQ ID NO: 24 |
| GlaA from *Aspergillus niger* including ss nucleotide sequence | 25 | Sequence encoding the signal sequence corresponds to positions 1-54 of SEQ ID NO: 25. 'Stop' codon is omitted. Codon usage should be taken into consideration when cloning for expression in C1. |
| EG2 from C1, including ss, amino acid sequence | 26 | Signal sequence corresponds to positions 1-16 of SEQ ID NO: 26 |
| EG2 from C1, including ss, nucleotide sequence | 27 | Sequence encoding the signal sequence corresponds to positions 1-48 of SEQ ID NO: 27. 'Stop' codon is omitted. Codon usage should be taken into consideration when cloning for expression in C1. |
| GCN4 leucine zipper amino acid sequence | 28 | The leucine zipper corresponds to positions 252-254, 259-261, 266-268 and 273-275 of SEQ ID NO: 28. |
| T4 Foldon amino acid sequence | 29 | |
| T4 Foldon nucleotide sequence | 30 | |
| KEX2 cleavage site amino acid sequence | 31 | |
| FLAG-tag amino acid sequence | 32 | |

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Expression of Hemagglutinin (HA) and Neuraminidase (NA) in *Myceliophthora thermophila* (C1)

Several series of expression constructs were designed for expression of recombinant HA proteins of various influenza virus strains in C1. A list of HA proteins tested in the study is detailed in Table 1 below. The expression constructs are detailed in FIGS. 1-4 (FIGS. 1-3—constructs with HA; FIG. 4—constructs with NA. P=promoter, ss=signal sequence, T=terminator). The HA type or NA included in each construct is marked in boldface. A list of abbreviations used to describe the various elements in the constructs is provided in FIG. 5. Production of the constructs is described in detail below under "Materials and Methods".

TABLE 1

HA proteins/viral strains

| Abbreviation | Viral strain |
|---|---|
| NC | A/H1N1 A/New Caledonia/20/99 |
| CA | A/H1N1 A/California/04/2009 |
| UR | A/H3N2 A/Uruguay/716/07 (A/Brisbane/10/07-like) |
| FL | B/Florida/04/2006: B Yamagata lineage |
| PR | A/H1N1 A Puerto Rico/08/1934 |
| Tex | A/H3N2 A/Texas/50/2012 |

Initially, HAs were expressed under cbh1 (cellobiohydrolase 1) or chi1 (chitinase 1) promoter, fused to the well-secreted *A. niger* glucoamylase A (GlaA) as a carrier to facilitate secretion of the HAs into the extracellular medium. The HA genes were fused to the part of the glaA gene that encodes the catalytic domain of GlaA. A KEX2 cleavage site (VISKR) was designed in between the glaA and HA gene to obtain a separate HA protein after cleavage of the site in the Golgi apparatus. The constructs further included a C-terminal FLAG tag for detection and purification purposes. In this initial series of expression constructs, the HAs were expressed without their transmembrane domain (TMD) and cytoplasmic tail.

In a modified version of the expression constructs, the hex1 (hexagonal peroxisome, Woronin body) promoter was tested, which is considered an early constitutive promoter, induced earlier compared to the other two promoters.

For HA New Caledonia, additional construct variants were made, as follows:

Construct with cbh1 or chi1 promoter, without GlaA carrier protein, but with cbh1 signal sequence for targeting to the ER.
Construct with chi1 promoter and Gla1 (C1 Glucoamylase 1) as a carrier protein.
Construct with EG2 (Endoglucanase 2) as a carrier protein.
Construct with hex1 promoter, GlaA carrier protein and without a FLAG tag.

C1 host strains for expressing the constructs were selected based on a proteolytic stability assay. Briefly, HAs produced with a baculovirus expression system (Protein Sciences Corporation, Meriden USA) were tested for proteolytic stability in end-of-fermentation (EOF) culture medium of several candidate C1 host strains (see Table 2 below). Less HA degradation was observed in the presence of the culture filtrates of the strains D240 (a high-cellulase (HC) strain) and D389 (a low-cellulase (LC) strain) compared to the other strains that were tested. D240 and D389 were therefore selected as host strains for producing the recombinant HAs. In later experiments, D382 was also tested for recombinant expression of HA.

Transformation was carried out as described below under "Material and Methods".

Following transformation, transformants were collected and cultivated in 96-well plates. The medium was screened for expression of glucoamylase (if applicable) and hemagglutinin. Positive transformants were further cultivated in shake flasks and expression of HA was evaluated using blotting techniques and an HA activity assay. The results are summarized in FIGS. 1A-B.

Analysis of the obtained transformants revealed that recombinant HA_NC was better expressed in C1 when the FLAG-tag sequence was omitted. Without this tag high molecular weight species containing HA (130-160 kDa) were detected in the extracellular medium of shake flask cultivations, as shown on Western blot with a monoclonal antibody against HA_NC. Based on the signal strength this represents approximately 30 mg/L in the culture medium if extrapolated to a large-scale fermentation, reaching a total extracellular protein level of 10 g/L. The expression level of HA_NC was higher in the LC strain than in the HC strain. In addition, high levels of HA were found intracellularly and/or cell-wall-associated, which is estimated to represent at least as much as what is found in the medium.

Highest expression was obtained with transformants containing a construct with the hex1 promoter.

Figure 2D:
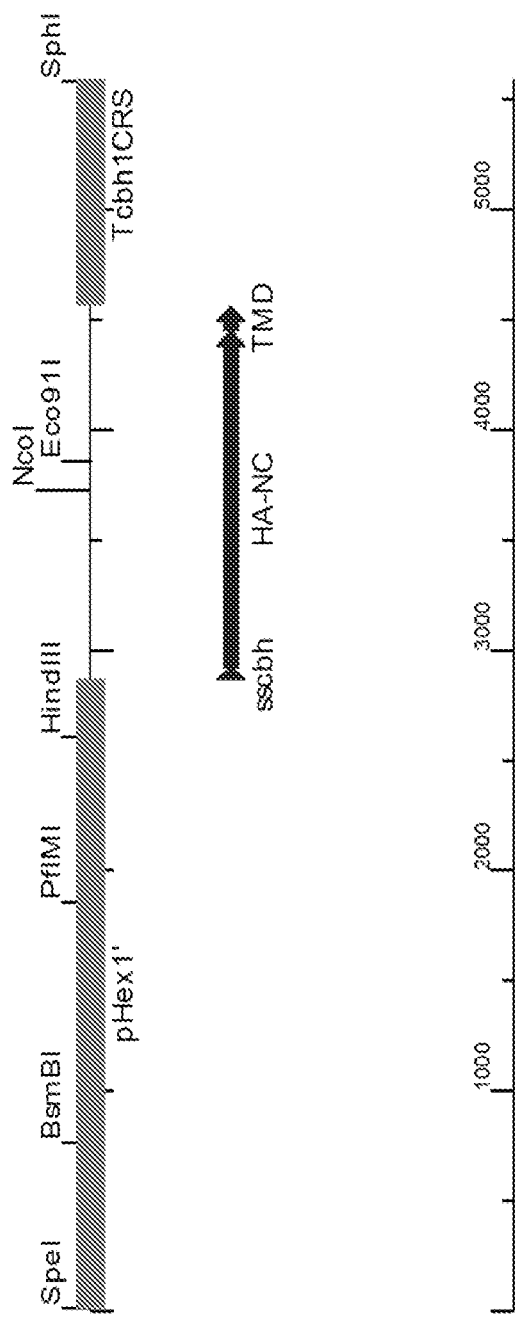
FIG. 2D. Illustration of the fragment used for transformation.
Figure 6:
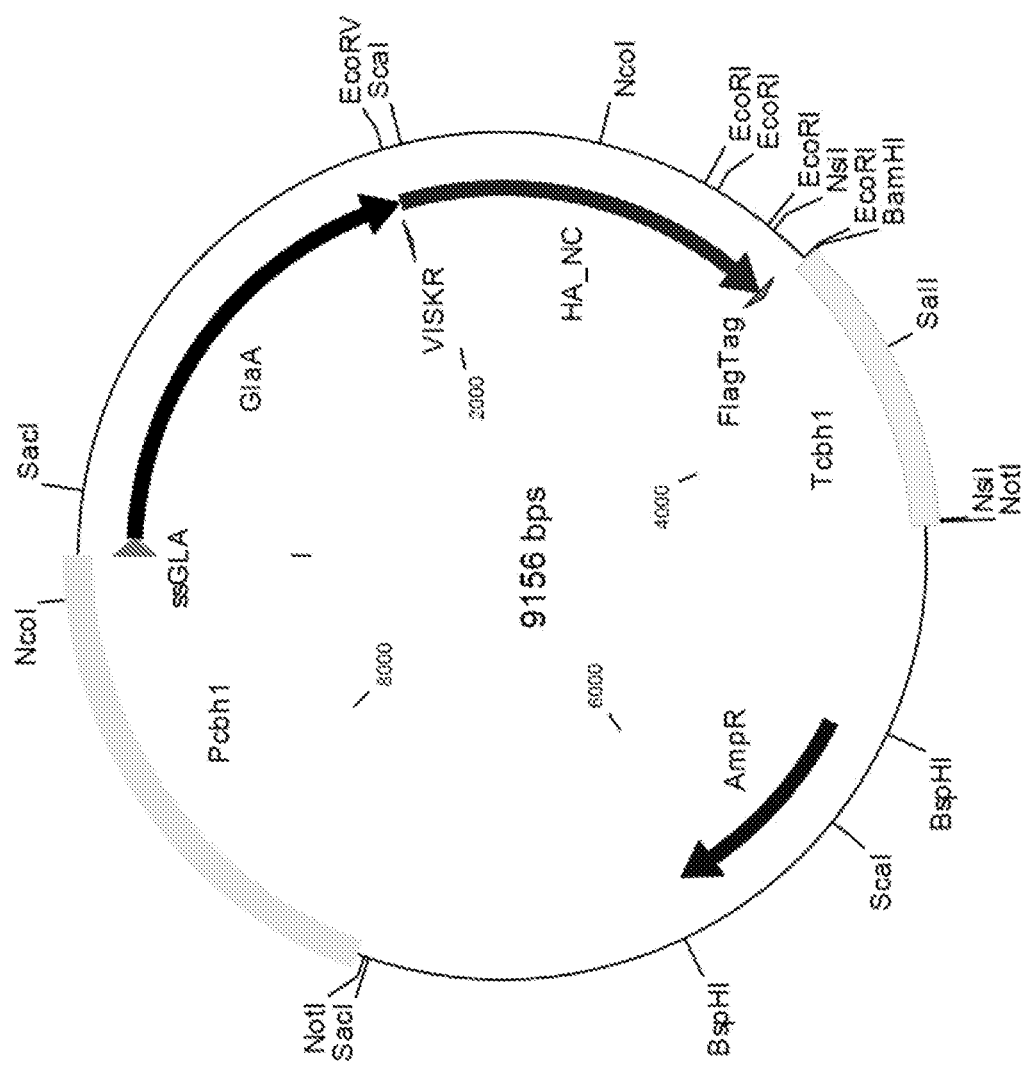
FIG. 6. Exemplary expression vector for heterologous protein production in C1.

A second series of expression constructs were designed, in which the presence of the native transmembrane domain (TMD) of HA or a recombinant C-terminal trimerization domain from T4 bacteriophage fibritin (T4 foldon domain) was tested. The T4 foldon domain was added to facilitate stability of the HA upon extracellular secretion. A linker of eight Gly residues ("8×G") was cloned between the HA and T4 foldon domain. The TMD was added to test its effect on expression levels and activity of the obtained HA (an HA construct containing the TMD was not expected to be secreted, but rather found intracellularly or cell-wall associated). In addition, a modified KEX2 proteolytic site containing a stretch of five Gly residues ("5×G") between HA and GlaA carrier was tested in order to test whether such modified linker would result in obtaining higher levels of separate HA protein. The promoter used for this series was hex1, based on the stronger expression obtained using this promoter in the previous series. The various constructs in the series are detailed in FIGS. 2A-2B. FIG. 2C illustrates an expression vector containing the construct Phex1-ssCbh-NC-TMD-Tcbh1 (sequence of the expression vector is set forth as SEQ ID NO: 17). FIG. 2D illustrates the fragment used for transformation.

As seen with the first series, better expression was achieved without the carrier GlaA. When the carrier was present, only Gla-HA fusion proteins were visible, even when the modified proteolytic site between the two moieties was used. The presence of a C-terminal T4-foldon domain had a positive effect on the levels of HA detected extracellularly, however the resulting HA seemed to be inactive (negative results in the hemagglutination assay). To further evaluate the activity of HA fused to a T4 foldon domain, HA expressed from the construct Phex1-ssCbh-NC-8×G-T4 foldon-Tcbh1 was purified and tested in an immunogenicity assay in mice (see Example 2 below). No functional immunogenicity was observed.

The natural transmembrane domain of HA had a positive effect on expression levels (intracellular or cell wall-associated). In addition, the resulting protein was highly active in the HA activity assay. To further evaluate the activity of HA with its TMD, HA expressed from the construct Phex1-ssCbh-NC-TMD-Tcbh1 was purified and tested in an immunogenicity assay in mice (see Example 2 below). Functional immunogenicity was observed, which was particularly effective, as will be described in more detail below.

A third series of expression constructs were designed, in which HAs of different types, including types that were not tested until now, were expressed under the hex1 promoter with cbh signal sequence, no carrier, and with T4 foldon domain or TMD at the C-terminus. In this series the T4 foldon domain was cloned without the Gly linker or with modified linkers between the HA and the T4 foldon domain. In addition, two variants of neuraminidase (NA) were also tested. The various constructs in the series are detailed in FIGS. 3-4.

C1 was able to produce HAs of different types. It was demonstrated that between 50-100 mg of proteins per liter of each of the HA type could be produced by C1 strains. In one or more cases expression levels of ~300 mg per liter were achieved.

As seen with the second series, the presence of a C-terminal T4-foldon domain had a positive effect on the levels of HA detected extracellularly, however the resulting HA seemed to be inactive (negative results in the hemagglutination assay), even with no linker or with modified linkers between the HA and T4 foldon. The natural transmembrane domain of HA again showed a positive effect on expression levels (intracellular or cell wall-associated). In addition, the resulting proteins were highly active in the HA activity assay. Both type A and type B influenza proteins were successfully expressed and found to be biologically active.

With respect to NA, it was found that it is well expressed in C1 and can be detected both extra- and intra-cellularly.

Materials and Methods

HA Protein Standards

HA protein standards were obtained from Protein Sciences Corporation (Meriden, USA). These proteins were produced in insect cells using the baculovirus expression vector system and purified to >90% purity under conditions that preserve the biological activity and tertiary structure. The protein standards were stored at 4° C. as recommended by the manufacturer. In addition, a batch of egg-derived HA from A/H1N1 A/New Caledonia/20/99 (NC) was ordered from the National Institute for Biological Standards and Control (NIBSC). This sample was aliquoted and stored at −20° C. as recommended by the manufacturer.

C1 Strains

Candidate C1 production hosts tested in the study are indicated in Table 2. HC refers to a C1 High-Cellulase strain and LC to a C1 Low-Cellulase strain. Prt- refers to protease deficient, Δalp1 refers to gene disruption of the major secreted protease, Δalp2 refers to gene disruption of a highly expressed vacuolar protease and Δchi1 refers to gene disruption of the highly expressed extracellular C1 chitinase in C1. All strains are Δpyr5

TABLE 2

C1 host strains

| C1 host strain | Deposit info. | Code |
|---|---|---|
| HC prt- | | D202 |
| HC prt-Δalp1 | "UV18-100f" deposit no. CBS141147 | D240 |
| HC prt-Δalp1Δpep4 | | D249 |
| HC prt-Δalp1Δpep4Δalp2, Δprt1 | "UV18-100f" deposit no. CBS141143 | D270 |
| LC prt-Δalp1 | | D326 |
| LC prt-Δalp1Δchi1 | "W1L#100I" deposit no. CBS141149 | D382 |
| LC prt-Δalp1Δchi1Δalp2 | "W1L#100I" deposit no. CBS141153 | D389 |

Construction of Expression Vectors

The expression vector used herein for heterologous protein production in C1, pP-ssglaA-glaA-HA-FLAG-tag, is shown in FIG. 6. This expression vector makes use of the well-secreted *A. niger* glucoamylase A protein as a carrier, facilitating the secretion of a heterologous protein into the extracellular medium. The HA genes were fused to the part of the glaA gene that encodes the catalytic domain of glucoamylase A of *A. niger*. A FLAG-tag sequence was fused C-terminally and incorporated for detection and purification purposes. The FLAG-tag is a short, hydrophilic 8-amino acid peptide with the sequence Asp-Tyr-Lys-Asp-Asp-Asp-Asp-Lys (DYKDDDDK, SEQ ID NO: 32).

Generation of Constructs of the First Series

For HC transformation experiments the following basic cloning vector was used:

pVJ1 (Pcbh1_glaA_kex2_GeneX_Tcbh1) digested with EcoRV-EcoRI.

EcoRV is located in the kex2-site and EcoRI is located immediately after the stop codon of GeneX.

This vector was used to ligate the following synthetic gene fragments, codon-optimized for C1 based on 43 well expressed genes, secreted into to the culture medium (all synthetic fragments were sub-cloned by GeneArt® in a pMK or pMS shuttle vector):

HA_NC_FLAG-tag×EcoRV-EcoRI (1577 bp)
HA_UR_FLAG-tag×EcoRV-EcoRI (1586 bp)
HA_FL_FLAG-tag×EcoRV-EcoRI (1655 bp)
HA_NC×EcoRV-EcoRI (1553 bp)

For LC transformation experiments the following basic cloning vector was used:

pVJ6 (Pchi1_glaA_kex2_Gene-of interest_Tcbh1) digested with EcoRV-EcoRI.

EcoRV is located in the kex2 site and EcoRI is located immediately after the stop codon of the gene of interest.

This vector was used to ligate the following synthetic gene fragments: (all synthetic fragments were sub-cloned by GeneArt® in a pMK or pMS shuttle vector).

HA_NC_FLAG-tag×EcoRV-EcoRI (1577 bp)
HA_UR_FLAG-tag×EcoRV-EcoRI (1586 bp)
HA_FL_FLAG-tag×EcoRV-EcoRI 1655 bp)
HA_NC×EcoRV-EcoRI (1553 bp)

For HA New Caledonia, additional construct variants were made, as follows:

* Vector with cbh1 promoter or chi1 promoter, without GlaA carrier protein, but with cbh1 signal sequence for targeting to the ER. This vector was generated as follows:

Cloning vector pCBHProm was digested with SacI-BspHI and the 1819 bp fragment, containing the cbh1 promoter, was isolated.

Cloning vector pVJ1 was digested with SacI-EcoRI and the 3896 bp fragment, containing the cbh1 terminator and pUC backbone, was isolated.

These two fragments were ligated in a three way ligation with the synthetic fragment digested with PciI-EcoRI (1617 bp) containing the sscbh1-HA_NC_FLAG-tag.

Cloning vector pPchi1-linker-Tcbh1 was digested with NcoI-BspHI and the 5758 bp fragment, containing the cbh1 promoter-cbh1 terminator and pUC backbone, was isolated. The vector was used in a ligation with the synthetic fragment digested with PciI-EcoRI (1617 bp) containing the sscbh1-HA_NC_FLAG-tag.

* Vector with chi1 promoter and Gla1 (C1 homologue) as a carrier protein, generated as follows:

Cloning vector pPch1-Gla1-XynB was digested with BsrGI-EcoRI and the 6609 bp fragment, containing the chi1 promoter, part of the Gla1 carrier protein, and cbh1 terminator, was isolated.

Cloning vector pPch1-Gla1-XynB was digested with BsrGI-MabI and the 783 bp fragment, containing part of the Gla1 carrier protein, was isolated.

These two fragments were ligated in a three way ligation with the synthetic fragment digested with MabI-EcoRI (1723 bp) containing the part of Gla1, a KEX2 site, and HA_NC_FLAG-tag.

* Vector with EG2 as a carrier protein, generated as follows:

Cloning vector pPcbh1_EG2_Tcbh1 was digested with SacI-PciI and the 3031 bp fragment, containing the cbh1 promoter and part of the EG2 carrier protein, was isolated.

Cloning vector pVJ1 was digested with SacI-EcoRI and the 3896 bp fragment, containing the cbh1 terminator and pUC backbone, was isolated.

These two fragments were ligated in a three way ligation with the synthetic fragment digested with PciI-EcoRI (1669 bp) containing the part of EG2, a KEX2 site, and HA_NC_FLAG-tag.

* Vector with 'early constitutive' promoter hex1, GlaA carrier protein and HA_NC without FLAG-tag, generated as follows:

Cloning vector pTcV1011 digested with SacI-EcoRV and the 1643 bp fragment, containing the hex1 promoter, GlaA carrier protein, and part of the KEX2 site, was isolated.

Cloning vector pVJ1 was digested with SacI-EcoRI and the 3896 bp fragment, containing the cbh1 terminator and pUC backbone, was isolated.

These two fragments were ligated in a three way ligation with the synthetic fragment digested with EcoRV-EcoRI (1553 bp) containing the sscbh1-HA_NC.

All vectors were generated in XL1-blue (Stratagene). From all vectors cloning junctions were verified by sequence analysis.

Generation of Constructs of the Third Series

The HA or NA expression cassettes were excised from their vectors using NotI. The pyr5 selection marker was excised from its vector (DNL35) using BglII. Both fragments were separated from plasmid backbone and purified from gel using the Wizard® SV Gel and PCR Clean up System (Promega). C1 hosts D389 and D382 were co-transformed with a single HA or NA expression cassette and the pyr5 marker.

Transformation and Microtiterplate (MTP) Cultivations

The expression vectors were digested with NotI to generate a foreign-DNA free expression cassette. These expression cassettes were co-transformed with the pyr5 marker in pyr5-deficient C1 strains.

Purification streaks of 96 transformants of each strain were made on minimal medium plates containing sucrose and incubated for 4 days at 35° C. Pure colonies were transferred to a 96-well plate containing Caylase medium (mother plate) and incubated at 35° C. After 3 days 3 µl of culture per well was transferred to new 96 well plates (daughter plates) containing production medium (($NH_4$)$_2SO_4$, 35 mM, NaCl, 7 mM, $KH_2PO_4$, 55 mM, Glucose, 0.5%, $MgSO_4$, 2 mM, trace element solution, casamino acids, 0.1%, biotin, 4 µg/L, penicillin 20 g/L, streptomycin 50 g/L, 10 mM. pH set to 5.5 with 10 M KOH) and plates were incubated for 72-96 hours. Supernatants were subsequently assayed for the required target expression or enzyme activity. For some constructs, the daughter plate medium used was either production medium or adapted inoculum medium (aIM), the growth temperatures were 35°, 30° C. or a combination of 35° C. followed by 30° C., and daughter plates were incubated for 48 and 72 (aIM) hrs.

In case of TMD-containing antigens, 100 µl of each culture (well) was transferred from the daughter plate wells to the wells of a 96-wells PCR plate. This was centrifuged for 15 minutes at 4000 rpm. The culture liquid was removed and 100 µl of extraction buffer (50 mM Tris-Cl pH 7.5, 1 mM EDTA, 1% SDS, 0.2% CHAPS) was added per well. This was mixed well and incubated for 5 minutes at 96° C. The plate was subsequently centrifuged for 15 minutes at 4000 rpm and the supernatants transferred to a new 96-wells plate. Twenty µL of this supernatant was used to spot onto PVDF membranes. Spot blots were subsequently blocked with BSA and screened using appropriate antibody. HRP conjugated secondary antibody substrate SuperSignal™ West Dura extended Duration Substrate (34075; ThermoFisher Scientific) was used to visualize bound antibody. Images were made using the Bio-Rad ChemiDoc. Selected transformant culture samples, either microtiter plate or shake flask derived, were further studied using SDS-PAGE and western blotting analyses according to standard techniques. The western blots were screened using the same antibody in a similar way as conducted for the spot blots.

Shake Flask Cultivation Conditions

Shake flask cultivation experiments were carried out in 300 ml flasks containing 50 ml medium. LC and HC were standard cultivated in production medium as described above, containing ammonium as nitrogen source and 0.5% glucose. Both strains were also tested in minimal medium (MM) and complete medium (CM)) containing besides 1% glucose, nitrate as nitrogen source, 0.1% casamino acids (in case of CM), 0.5% YE (in case of CM) (and vitamins). Cultivation was carried out at 250 rpm (1 inch/orbit) and 35° C.

Spotblot Analysis

Most of the transformants obtained were screened by spotblot analysis. After microtitre plate culture, plates were harvested by centrifugation and supernatants were transferred to new 96-well plates. For LC strains 25 µl of supernatant was used and for HC strains 12.5 µl was used. Samples were denatured at 96° C. for 5 min. cooled on ice and transferred to PVDF membrane. Spotblots were stained with mAb αGlaA or mAb αHA_NC (AbCam ab66189).

SDS-PAGE and Western Analysis

SDS-PAGE and Western blotting was carried out according to standard procedures. Development of Western blots with alkaline phosphatase was carried out with NBT and BCIP as substrates. Development of Western blots with Horse radish peroxidase was carried out with ECL detection reagents according to supplier (Invitrogen: Novex®ECL #WP20005). The following protocol was used for stripping of the developed Western blots (Mild stripping procedure according to AbCam):

Fresh stripping buffer was prepared (1 L: 15 g glycine, 1 g SDS, 10 ml Tween20, adjust pH to 2.2) and the membrane incubated in the stripping buffer for 10 min at RT (shaking). The buffer was discarded and the procedure repeated with fresh stripping buffer. Next, the membrane was washed twice with PBS and twice with TBS-Tween20.

2D Gel Electrophoresis

Prior to 2D SDS-PAGE, samples were 10-20× concentrated using Amicon Ultra 0.5 ml 10K centrifugal filters, subsequently samples were desalted using BioRad micro Biospin 6 chromatography columns, and protein concentration was determined using BCA assay (Pierce). Protein samples were purified using BioRad ReadyPrep 2D cleanup kit according to supplier. After purification, protein pellets (~200 µg) were rehydrated in 200 µl 2-D rehydratation buffer 1 (BioRad) containing: 7M Urea, 2M Thiourea, 4% CHAPS, 50 mM DTT, 0.2% Bio-Lyte 3/10 ampholyte (20%), and 0.002% Bromophenol Blue. Rehydrated protein samples were loaded on BioRad Ready Strip IPG strips (11 cm pH 4-7) and incubated O/N at RT. After complete rehydratation of IPG strips, the strips were focused according to the supplier (BioRad). The second dimension was run on SDS-PAGE Criterion TGX 4-15% gradients gels (Bio-Rad). Gels were either used for Coomassie Brilliant Blue staining or protein was transferred to PVDF.

Hemagglutination Assay

Normally, influenza virus particles have HA on their surface that binds to sialic acid receptors on cells. The virus binds to erythrocytes (red blood cells), causing the formation of a lattice. This property is called hemagglutination. If functional HA is present in a sample containing red blood cells, the lattice is formed which is visible as "staying in solution" instead of precipitation of the red blood cells to the bottom of the vessel.

For rapid detection of HA secretion into the culture medium, cultures were tested for hemagglutinin activity by adding (filtered) fungal culture supernatant, serial diluted [in 1×PBS (without Ca$^{2+}$ and Mg$^{2+}$) 50 µl final amount] in V bottom 96-well plates, to an equal amount (50 µl) of washed 0.5% chicken red blood cells in 1× PBS (without Ca$^{2+}$ and Mg$^{2+}$). Plates were then incubated at RT for 1 h. Samples were compared to a known amount of a purified HA standard (Protein Sciences Corp. or NIBSC).

EG2 Activity Assay

EG2 activity was measured by an azo-CMCase assay (MegaZyme), according to the manufacturer's instructions.

BCA Assay

The protein content was quantified by a BCA assay (Pierce), according to according to the manufacturer's instructions.

Purification of Secreted HA

Following shake flask culture the fermentation broth was centrifuged and the supernatant collected. A 35 ml sample of the supernatant was concentrated using Millipore Amicon Ultra filter (with a cut off of 10 kDa) to a total volume of 300 µl (>100× concentrated). Prior to loading on a column, the sample was cleared by centrifugation (1 min at 14000 rpm). Gel filtration was performed in PBS and a 100 µl sample was loaded onto a 24-ml Superdex 200 column. Sample was processed with flow rate of 1 ml/min, and fractions of 0.5 ml were collected (ÄKTA Explorer system 1). Fractions were analyzed on Western blot with a monoclonal antibody against HA_NC.

Purification of TMD-Containing HA

Figure 7:
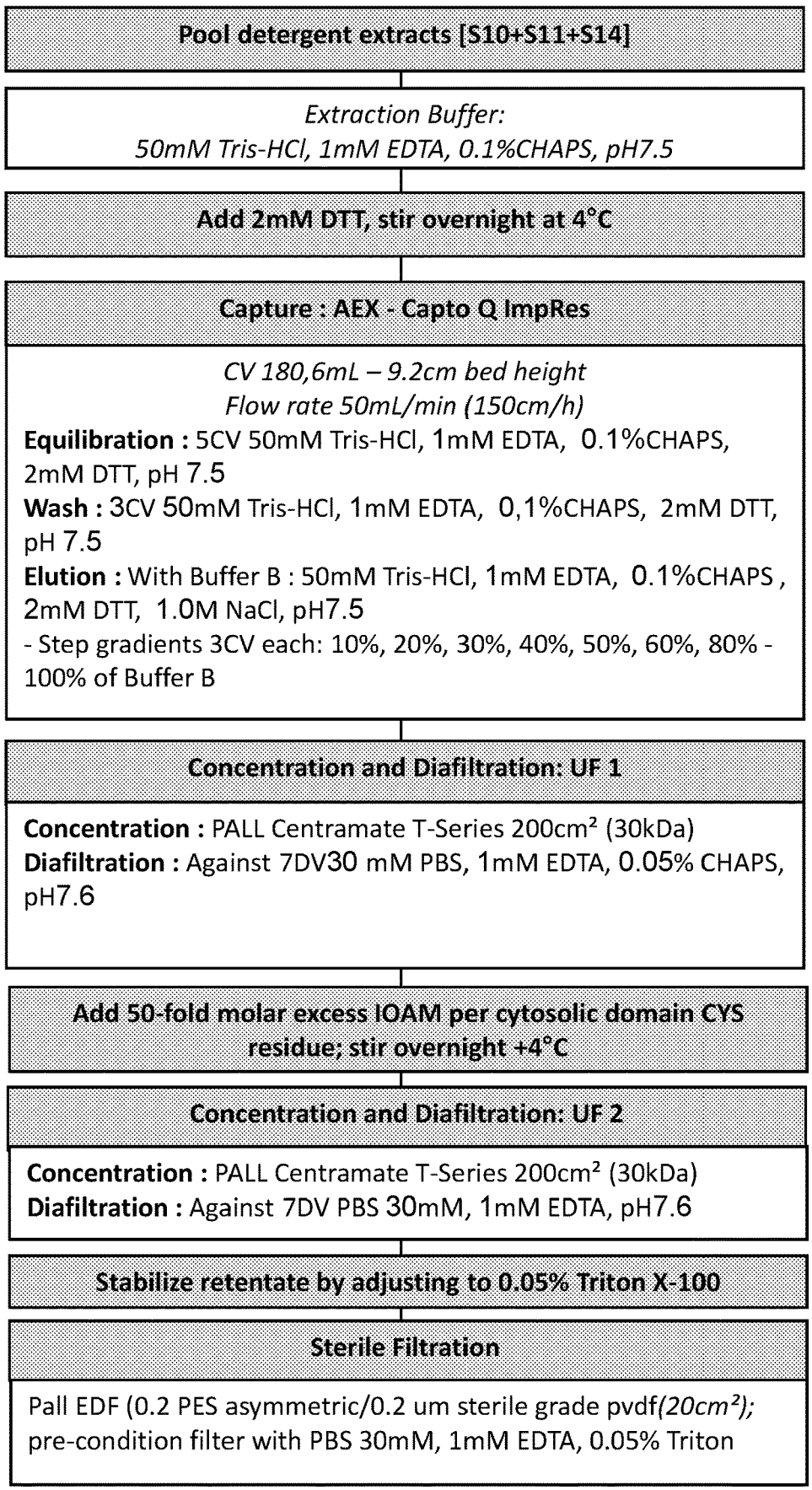
FIG. 7. Purification procedure of TMD-containing HA.

TMD-containing HAs were extracted from mycelium fragments using an extraction buffer and subsequently purified using AEX-Capto Q ImpRes. See FIG. 7 for the purification procedure.

Deglycosylation Experiments

Both extracellular and intracellular fractions were used in deglycosylation experiments. EndoH (Endo-β-Nacetylglucosaminidase; Roche 11 088 726 001) deglycosylation was performed under conditions as recommended by the supplier. Therefore, reactions were performed O/N at 37° C. in a buffer containing: 20 mM NaOAc pH 5.5, 0.5 mM PMSF (phenylmethylsulfonylfluoride), 0.1 M β-mercaptoethanol and 0.02% SDS. Prior to adding 10 mU EndoH the protein samples were denatured for 10 min at 96° C. Samples were analyzed by SDS-PAGE and Western blotting and stained with the mAb against HA_NC (AbCam ab66189). PNGaseF (Peptide N-glycosidase F from *Elizabethkingia miricola*; Sigma-Aldrich G5166) deglycosylation was performed under similar conditions as EndoH deglycosylation with the only difference that Triton X-100 is added to a final concentration of 0.1%. After denaturation of protein samples 5 U of PNGaseF was added and samples were incubated O/N at 37° C. Samples were analyzed by SDS-PAGE and Western blotting and stained with the mAb against HA_NC (AbCam ab66189).

In Vitro KEX2 Processing

Both extracellular and intracellular fractions were used in a KEX2 processing experiments. Samples were tested both in native- and denatured form. KEX2 protease protein derived from *Saccharomyces cerevisiae*, produced in High-5 insect cells (AbCam; ab96554). KEX2 protein cleavage was performed under the following conditions: Fractions were incubated in 50 mM Tris/HCl pH=7.5, 5 mM CaCl$_2$ 0.5 mM PMSF and 0.1% Triton X-100. Protein samples were either incubated in native or denatured form with 80 mU KEX2 for 4 hrs at 37° C. Samples were analyzed by SDS-PAGE and Western blotting and stained with the mAb against HA_NC (AbCam ab66189) and the monoclonal against GlaA.

Trypsin Digestions

Partial trypsin digestions were performed at RT in 50 mM NaOAc pH=5.5 buffer. Extracellular sample was mixed with assay buffer and trypsin [TPCK trypsin (Pierce); stock solution is 50 mg/ml (aliquots are stored at −70° C.). Working solution is 50 ng/µl]. Samples were taken at t=0, t=2', t=5', t=10', t=15', t=20', t=30', t=45', and t=60'. Digests were stopped by adding 6× SDS-PAGE loading buffer and denatured at 96° C. for 5 min Samples were analyzed by SDS-PAGE and Western blotting and stained with the mAb against HA_NC (AbCam ab66189) and the monoclonal against GlaA.

Fungal Mycelium Extracts

Figure 8:
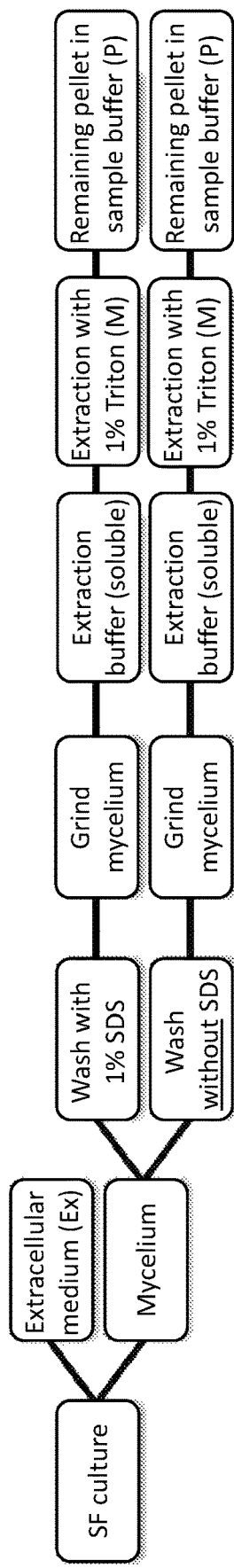
FIG. 8. Flowchart of fractionation study to distinguish between HA localized intracellularly or cell-wall attached.

The fractionation study used to distinguish between HA localized intracellularly or cell-wall attached was carried out as schematically shown in FIG. 8. Briefly, extracellular medium (Ex) from shake flask cultures was collected (the amount measured) and the mycelium harvested. Mycelium was washed with cold fresh production medium, weighed and divided into equal portions in wash buffer with or without SDS. This wash step was carried out for 1 hr at RT and wash medium was analyzed on SDS-PAGE. Grinded mycelium was resuspended in the same g/volume ratio extraction buffer as in the original shake flask culture, left in a tube for 10 minute on a rotating platform at RT and subsequently the tube was centrifuged for 5 minutes at 14000 rpm. The supernatant was analyzed on SDS-PAGE. The remaining pellet was resuspended again in the same volume of extraction buffer, now with Triton-X100 added to solubilize the membranes. After removal of the supernatant by centrifugation the final cell pellet was resuspended in SDS-PAGE sample buffer.

Preparation of Fungal Protoplasts

C1 LC cultures were grown for 2 days in Complete medium as described above. Protoplasts were generated and purified. An extra wash step was performed to reduce the risk of cell wall fragments contaminating the protoplasts.

Example 2

Immunogenicity of HA Produced in *Myceliophthora Thermophila* (C1)

Figure 9:
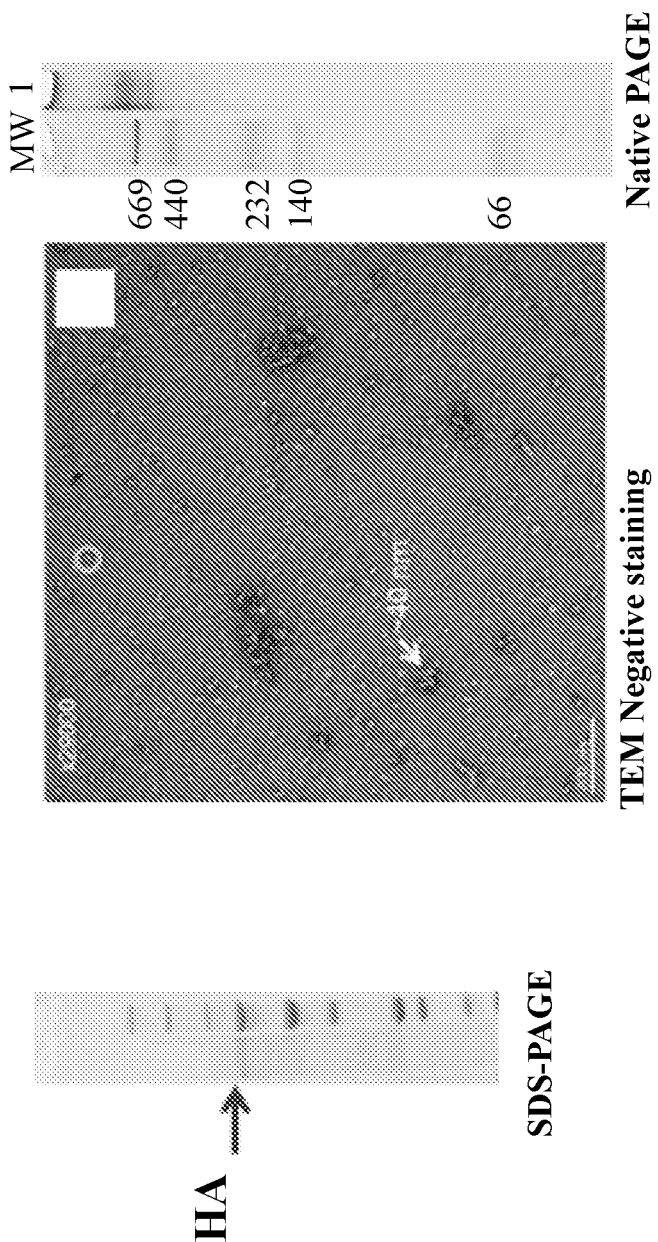
FIG. 9. Biochemical evaluation of rHA-TMD.

Animal tests were carried out to test immunogenicity of a full length recombinant hemagglutinin protein from the A/NewCaledonia/20/99 (H1N1) influenza strain possessing the transmembrane domain (rHA-TMD) produced in C1. Biochemical evaluation of rHA-TMD is shown in FIG. 9, showing SDS-PAGE, native PAGE and analysis of oligomeric state using TEM Negative staining. The magnification in the TEM image is x29000. Scale bar=200 nm. The white arrow points to a ~40 nm oligomer. The white circle marks a ~15 nm oligomer.

A preceding immunogenicity study was conducted with a secreted form of rHA from the same viral strain produced in C1. The transmembrane domain of this rHA is truncated and it contains additional domains not found in a native HA (an 8-Gly domain and a T4 foldon domain). The rHA-8Gly-T4 construct did not induce functional antibody responses. It was then proposed that a construct with the transmembrane domain (rHA-TMD) could induce a better immunogenicity.

To this end, eight groups of 8 Balb/C ByJ mice received two intramuscular (IM) injections, given four weeks apart, of 3-fold escalating dosages—ranging from 1 to 30 µg—of rHA-TMD produced in C1. As negative control, 5 mice were immunized with PBS according to the same immunization schedule. Blood samples were collected on Day 27 and Day 49 for antibody response analysis by hemagglutination inhibition (HI) assay.

As will be described in more detail below, the results showed that as early as following a single injection in mice of full length rHA prepared in C1, specific functional antibody responses were induced that were further enhanced following the second injection.

Materials and Methods

Tested Compositions

Table 3 lists the compositions that were tested in the study. Protein contents quantified by Bradford technique was used for injection dose preparation. All compositions were stored at +5° C.±3° C. until use.

TABLE 3

Tested compositions

| Composition | Description | Concentration/Purity | Endotoxin Content* (EU/mL) | Purity |
|---|---|---|---|---|
| rHA-TMD C1 | Recombinant HA from A/New Caledonia/20/99 (H1N1) with transmembrane domain produced in C1 | BCA (BRD sp): 791 μg/mL<br>μBradford (ARD sp): 627 μg/mL<br>Purity: 80% | 12 | ≥96% |
| PBS (Eurobio) | | N/A | | |

*Endosafe testing at sp

Animal Information
Animal species: mice
Status: SPF
Strain: Balb/c ByJ mouse
Supplier: Charles River

Age: 9 weeks on DO

Sex: Female
Weight: 20-22 g
Individual identification by coloration
Care and maintenance: daily
Housing
Location: 4 animals/cage for all groups/cage in an air-conditioned building complying with L2 biosafety requirements.
Nb of animals/cage: 4
Diet: granulated food (M20, SDS, DIETEX France, St Gratien, France)
Water: Tap water, ad libitum, via an automatic watering system
Quarantine: N/A
Acclimation: Mice assigned for the study were acclimated to their designed housing for 5 days before immunization.
Group Definition
The group definition is summarized in the Table 4.

TABLE 4

Groups

| | Test composition | | Injections at W 0 and W 4 | |
|---|---|---|---|---|
| Group | Name | Quantity | Route | Volume injected (100 μL/injection) |
| A (8 mice) | rHA-TMD C1 | 1 μg | IM | 2 × 50 μL |
| B (8 mice) | rHA-TMD C1 | 3.33 μg | IM | 2 × 50 μL |
| C (8 mice) | rHA-TMD C1 | 10 μg | IM | 2 × 50 μL |
| D (8 mice) | rHA-TMD C1 | 30 μg | IM | 2 × 50 μL |
| M (5 mice) | PBS | — | IM | 2 × 50 μL |

Study Schedule

The study schedule is detailed in the Table 5.

TABLE 5

Study schedule

| Day | Group number | Number of animals | Interventions | Specific characteristics |
|---|---|---|---|---|
| D(−1) | A to M | 88 | Weighing and shaving | N/A |
| D 0 | A to M | 88 | Prime IM vaccination | Immunization with rHAs |
| D 27 | A to M | 88 | Weighing, blood sampling | Blood sampling at submandibular vein |
| D 28 | A to M | 88 | Boost IM vaccination | Immunization with rHAs |
| D 49 | A to M | 88 | Blood samplings and animal sacrifice | Final bleeding by exsanguination<br>Animal sacrifice by cervical dislocation |

Clinical Monitoring

Animals were observed daily on working days (from Monday to Friday) following the immunizations and weighted on days −1 and 27.

Biological Sampling

Blood samples were taken under isoflurane anesthesia from the retro-orbital sinus (ROS) or submandibular vein at D27 and after exsanguination by carotid section at D49 from all the animals. At D49, the anesthesia was performed by Imalgène (1.6 mg of Ketamine) and Rompun (0.32 mg of Xylazine) administrated under a volume of 2004, by intraperitoneal route.

For humoral response assays, at D27, 200 μL of blood were collected in vials containing clot activator and serum separator (BD Microtainer SST ref 365951). After two hours at +37° C., the blood was centrifuged at 10,000 rpm for 5 minutes and sera were stored at −20° C. until analysis.

At D49: 1 mL of blood was collected in vials containing clot activator and serum separator (BD Vacutainer SST II Advance ref 367957). After 2 days at +5° C., the blood was centrifuged at 2000 g during 20 minutes and serum was stored at −20° C. until analysis.

Hemagglutination Inhibition (HI) Assay

The assay is based on the ability of influenza virus to agglutinate red blood cells. A serum containing functional antibodies against HA inhibits the hemagglutination activity. In the assay, sera from influenza-immunized animals are titrated with influenza virus in order to characterize the concentration of functional anti-HA antibodies.

Reagents:

96-well V-bottom plates, (NUNC)

RDE (Receptor Destroying Enzyme): Neuraminidase from Vibrio cholerae Type III at 10 mU/mL (Sigma)

PBS without Ca++ and Mg++ (Gibco)

TPCK trypsin (Thermo Scientific)

Chicken red blood cells ("cRBCs"): 10% in PBS for serum treatment, 0.5% in PBS for HI assays (Sanofi Pasteur)

Influenza strain A/New Caledonia/20/99, clarified allantoic fluid 1900 Hemagglutination Unit (HAU)/50 μL The titration is performed as follows: Serial dilutions (2 fold) of the virus were performed in PBS in order to calibrate the viral suspension and obtain a concentration of 4 HAU/50 μL. Calibrated virus (50 μL) was then added to a V-shaped 96 well plate on 50 μL of serum serial dilutions (2 fold) in PBS starting from 1/10, and incubated one hour at room temperature. Chicken red blood cells (0.5% in PBS) (50 μL) were then added to each well and inhibition of hemagglutination (red point) or hemagglutination (pink network) was visually read after one hour at room temperature.

In order to eliminate serum non-specific inhibitors directed against the HA, each serum was treated prior to the HI assay with a receptor-destroying enzyme (RDE), chicken red blood cells and TPCK trypsin. Briefly, 10 mU/mL of RDE was added to each serum (5 volume of RDE for 1 volume of serum). The mix was then incubated 18 h at +37° C., followed by 1 h inactivation at +56° C. To cool, the mixture "serum-RDE" was placed between 30 min to 4 hours at +4° C. The "serum-RDE" mixture was then absorbed on 10% cRBCs in PBS for 30 min (5 volumes of cRBCs for 1 volume of serum), at room temperature, and then centrifuged at +5° C., 10 min at 700 g. The supernatant was collected and the trypsin treatment was carried out by mixing 10 volumes of RDE-RBC-heat inactivated serum (dilution serum 1:10) with 1 volume of 0.4% trypsin (w/v in saline) at +56° C. for 30 min. The HI was then performed and the final serum dilution still considered at 1:10.

Serial dilutions (2 fold) of the virus were performed in PBS in order to calibrate the viral suspension and obtain a concentration of 4 HAU/50 μL. Calibrated virus (50 μL) was then added to a V-shaped 96 well plate on 50 μL of serum serial dilutions (2 fold) in PBS starting from 1/10, and incubated one hour at room temperature. Chicken red blood cells (0.5% in PBS) (50 μL) were then added to each well and inhibition of hemagglutination (red point) or hemagglutination (pink network) was visually read after one hour at room temperature.

The HI titer value is the inverse of the last dilution of serum that completely inhibited hemagglutination. A value of 5, corresponding to half of the initial dilution (1/10), was arbitrarily given to all sera determined negative in order to perform statistical analysis.

The absence of non-specific agglutinins was controlled for each serum (4 serial dilutions of each serum and cRBCs without virus). A control of the cRBCs (only cRBCs and PBS) and a control of the presence of 4 HAU of the working dilution of virus were performed on each plate.

Observations and Deviations

At D28, the day after blood sampling from the submandibular vein, a mouse from group A was found sick likely because it did not recover from this intervention and was thus euthanized.

Results

Clinical Monitoring

An increase of mean body weight was observed in all groups from D1 to D27.

Humoral Response

Figure 10A:
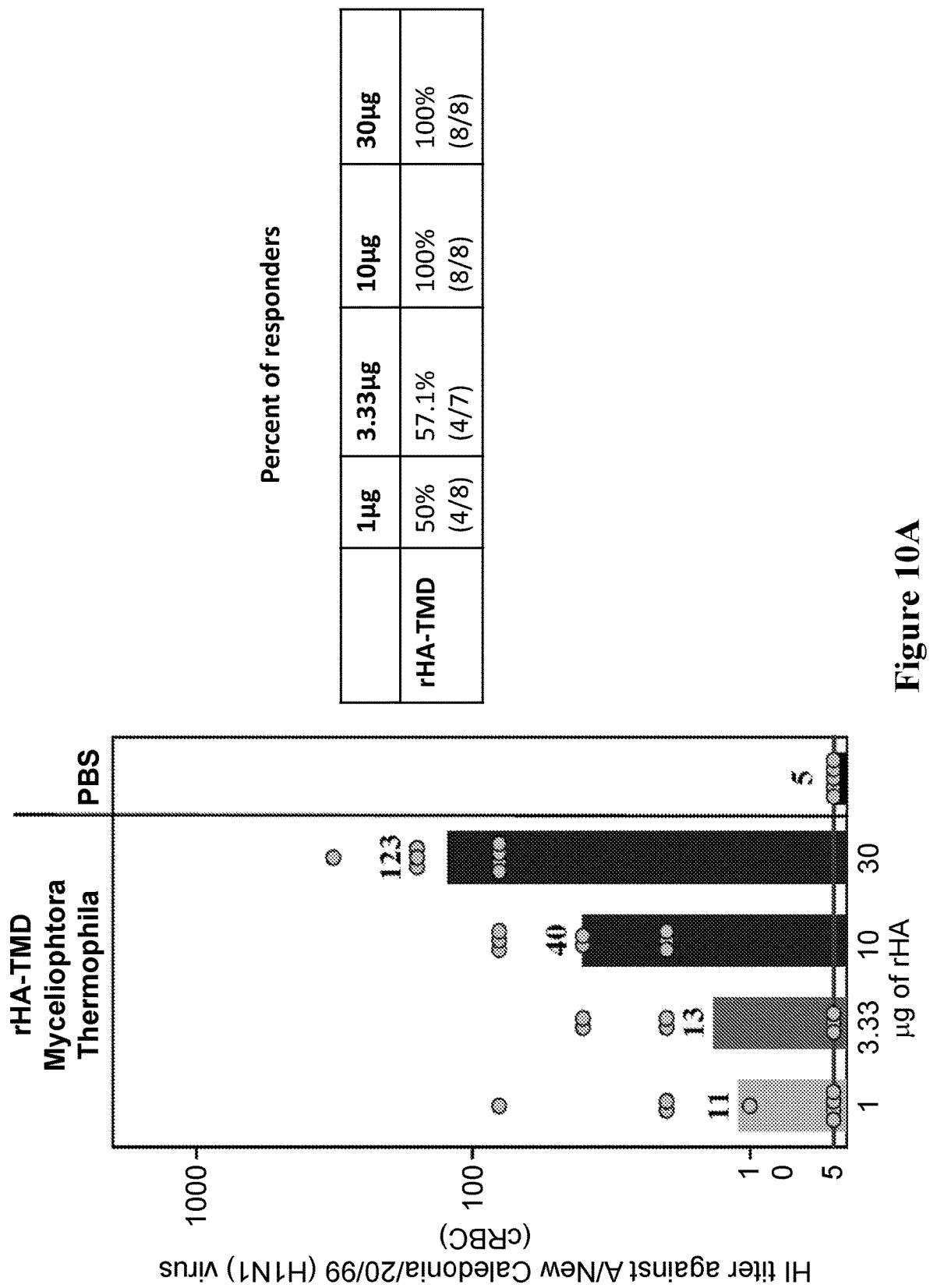
Figure 10B:
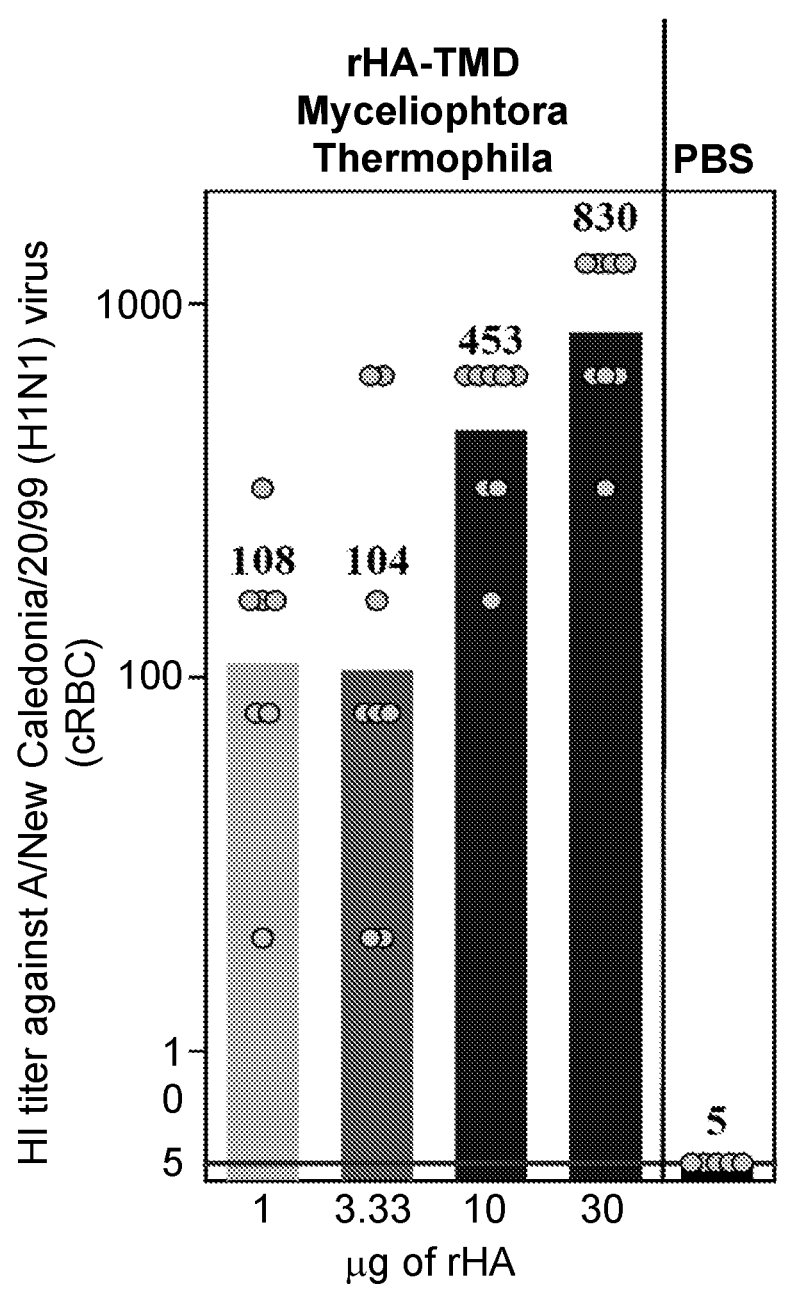
Figure 11:
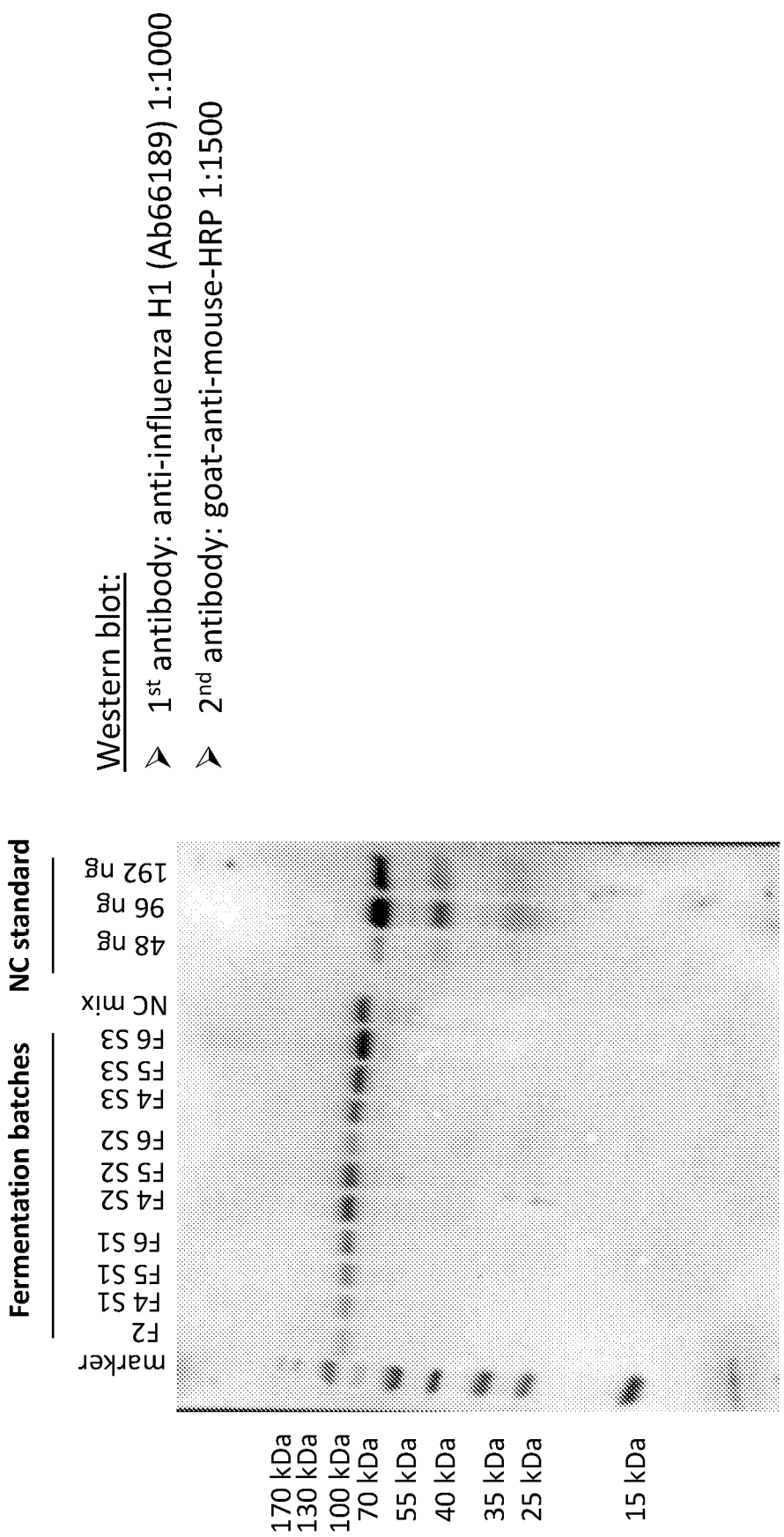
FIG. 11. Western blot analysis of HA production in C1 using stirred-tank fermentation.

The antibody responses elicited against A/New Caledonia/20/99 (H1N1) were measured in individual sera collected from all animals at D27 and D49 by HI assay. The results are presented in FIG. 10A-10B.

After the first injection of rHA, no or low HI responses were induced at the two lowest doses of C1-rHA, precluding statistical analysis. Still, the results strongly suggested that C1-rHA indeed induced antibody responses.

Following the booster injection, the responses were further enhanced. Significant dose-dependent HI effects were induced by C1-rHA with mean HI titers ranging from 108 to 830 for 1 and 30 μg dosages, respectively.

It is noted that the full length recombinant HA produced in C1 did not induce any negative clinical signs in the mice.

C1 can easily produce levels of 1 g/L of HAs and other antigens in 5 days fermentation therefore:

In seasonal influenza vaccine–total doses distributed=146 M/year

Each 0.5 mL dose is formulated to contain: 15 μg of HA for each strain.

Thus, 3×1000 L scale fermentation runs will be able to supply the annual global HA/strain needs against Influenza of 2,175 g.

Example 3

Stirred-Tank Fermentation of HA

Experiments were carried out to measure production levels of the rHA-TMD described above on a larger scale, in a stirred-tank fermenter with batch and fed-batch technologies. To this end, Minifors™ 3L bioreactors were used to culture C1 strain D389 expressing the rHA-TMD.

Table 6 summarizes the fermentations conditions of an initial set of experiments, carried out for 50 hrs. "Batch"—concentration of the indicated carbohydrate at the beginning of fermentation. "Fed-batch"—concentration of the carbohydrate in the feed. Fermentations were carried out at pH 7.5 with starting volume 1.5 liters.

TABLE 6

| | Fermentation conditions 50 hrs | | |
|---|---|---|---|
| Run # | Temp. (° C.) | Batch | Fed-batch |
| R465F2 | 25 | 4% xylose | none |
| R465F4 | 35 | 1% xylose | 47% xylose. |
| R465F5 | 35 | 1% glucose | 50% glucose. |
| R465F6 | 35 | 4.7% glucose | none |

Following fermentation, mycelia were collected and HA was extracted.

To evaluate mycelia concentration, the mycelial dry weight was measured. In brief, a certain amount of the fermentation broth was collected and washed a few times to remove media and media components, such as fermentation intermediates and secreted proteins. The resulting material was than dried for 24 h at 90° C. and weighted. All fermentation samples were found to contain about the same mycelium concentration.

Quantification of HA was carried out by comparing Western blot signals obtained for the extracted HA in comparison to HA standards of known amounts (FIG. 13).

The production level of the best batch was calculated to be approximately 375 mg/l which is 170 mg/l/day Table 7 summarizes the fermentations conditions and resulting HA production levels of a second set of experiments, carried out for 98-137 hrs. The table shows end-of-fermentation (EOF) results.

TABLE 7

Fermentation conditions and HA production level

| Run # | Time (h) | Temp (° C.) | C-source | Feed rate (%) | DM* (g/L) | HA (mg/L) | HA** (mg/g DM) | C-source (g/L) |
|---|---|---|---|---|---|---|---|---|
| R481F1 | 98 | 35 | glucose | 1 | 37.9 | 47.3 | 1.2 | 0.8 |
| R481F2 | 98 | 35 | xylose | 1 | 34.0 | 35.0 | 1.0 | 0.5 |
| R481F5 | 98 | 30 | xylose | 1 | 25.0 | 62.9 | 2.5 | 66.9 |
| R481F6 | 98 | 35-25 | glucose | 1 | 33.6 | 29.0 | 0.9 | 17.2 |
| R481F7 | 98 | 35-25 | xylose | 1 | 13.3 | 27.6 | 2.1 | 42.2 |
| R482F1 | 102 | 35 | glucose | 1 | 56.6 | 50.6 | 0.9 | 0.1 |
| R482F2 | 102 | 30 | glucose | 1 | 61.1 | 49.0 | 0.8 | 0.2 |
| R483F1 | 140 | 30 | glucose | 1 | 47.6 | 124 | 5.4 | 0.1 |
| R483F2 | 140 | 30 | xylose | 1 | 46.7 | 171.4 | 3.7 | 0.1 |
| R483F4 | 140 | 35-25 | glucose | 1 | 56.5 | 62.8 | 1.1 | 0.1 |
| R483F5 | 140 | 35-25 | xylose | 1 | 51.7 | 86.0 | 1.7 | 1.2 |
| R484F2 | 137 | 30 | glucose | 1 | 48.9 | 51.8 | 1.2 | 0.1 |
| R484F5 | 137 | 35 | glucose | 2 | 33.6 | 106.8 | 4.0 | 6.5 |
| R484F6 | 137 | 35 | xylose | 2 | 56.7 | 169.6 | 3.6 | 12.8 |
| R484F7 | 137 | 30 | glucose | 2 | 76.6 | 413.4 | 5.4 | 0.1 |

*Dry cell mass
**Estimated.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A *Myceliophthora thermophila* C1 genetically-modified to produce an influenza virus surface protein, comprising an expression construct comprising a nucleic acid sequence encoding the influenza virus surface protein operably linked to at least one C1 regulatory sequence, wherein the influenza virus surface protein comprises its ectodomain and transmembrane domain and is expressed in the C1 as a membrane-bound protein.

2. The genetically-modified *Myceliophthora thermophila* C1 of claim 1, wherein the influenza virus surface protein is hemagglutinin (HA).

3. The genetically-modified *Myceliophthora thermophila* C1 of claim 2, wherein the expression construct further comprises a nucleic acid sequence encoding a *Myceliophthora thermophila* C1 signal peptide linked in-frame to the nucleic acid sequence encoding the HA.

4. The genetically-modified *Myceliophthora thermophila* C1 of claim 2, wherein the HA subtype is selected from the group consisting of influenza A-H1, H2, H3, H4, H5, H6, H7, H8, H9, H10, H11, H12, H13, H14, H15 and H16; and influenza B subtype.

5. The genetically-modified *Myceliophthora thermophila* C1 of claim 2, wherein the HA subtype is a subtype infecting humans selected from influenza A subtypes H1, H2 and H3; and influenza B subtype.

6. The genetically-modified *Myceliophthora thermophila* C1 of claim 1, wherein the at least one *Myceliophthora thermophila* C1 regulatory sequence comprises a *Myceliophthora thermophila* C1 promoter.

7. The genetically-modified *Myceliophthora thermophila* C1 of claim 6, wherein the *Myceliophthora thermophila* C1 promoter is selected from the group consisting of: hex1, cbh1, chi1 and bgl promoters.

8. The genetically-modified *Myceliophthora thermophila* C1 of claim 3, wherein the *Myceliophthora thermophila* C1 signal peptide is a signal peptide derived from a protein selected from the group consisting of Gla1 and Cbh1.

9. The genetically-modified *Myceliophthora thermophila* C1 of claim 1, wherein the expression construct comprises: hex1 promoter operably linked to a nucleic acid sequence encoding a Cbh1 signal peptide fused to HA.

10. The genetically-modified *Myceliophthora thermophila* C1 of claim 1, wherein the influenza virus surface protein is a neuraminidase (NA).

11. The genetically-modified *Myceliophthora thermophila* C1 of claim 10, wherein the NA subtype is selected from the group consisting of influenza A-N1, N2, N3, N4, N5, N6, N7, N8 and N9; and influenza B subtype.

12. The genetically-modified *Myceliophthora thermophila* C1 of claim 10, wherein the NA subtype is a subtype infecting humans selected from influenza A subtypes N1 and N2; and influenza B subtype.

13. The genetically-modified *Myceliophthora thermophila* C1 of claim 10, wherein the expression construct comprises: hex1 promoter operably linked to a nucleic acid sequence encoding NA.

14. The genetically-modified *Myceliophthora thermophila* C1 of claim 1, wherein the *Myceliophthora thermophila* C1 strain is selected from the group consisting of: wild type C1 deposit no. VKM F-3500 D, UV13-6 deposit no. VKM F-3632 D, NG7C-19 deposit no. VKM F-3633 D, and UV18-25 deposit no. VKM F-3631.

15. A method for producing an influenza virus surface protein, the method comprising culturing the genetically-modified *Myceliophthora thermophila* C1 of claim 1 under conditions suitable for expressing the influenza virus surface protein; and recovering the influenza virus surface protein.

16. The method of claim 15, wherein recovering the influenza virus surface protein comprises extraction from mycelia.

17. An expression construct for expressing a membrane bound influenza virus surface protein in *Myceliophthora thermophila* C1, the expression construct comprising at least one *Myceliophthora thermophila* C1 regulatory sequence operably linked to a nucleic acid sequence encoding an influenza virus surface protein, wherein the influenza virus surface protein comprises its ectodomain and transmembrane domain.

18. The method of claim 15, wherein the recovered influenza virus surface protein is further purified.

19. The method of claim 18, wherein the purified virus surface protein is formulated as a vaccine.

20. The method of claim 19, wherein the vaccine does not contain an added adjuvant.

* * * * *

```
                         SEQUENCE LISTING

<160> NUMBER OF SEQ ID NOS: 32

<210> SEQ ID NO 1
<211> LENGTH: 2869
<212> TYPE: DNA
<213> ORGANISM: Artificial Sequence
<220> FEATURE:
<223> OTHER INFORMATION: Promoter

<400> SEQUENCE: 1
ggccgctcta gaactagtac ggcgtgcaag tagtgtcttt ctttgcactc ccgccgtccc      60
agaagacgcc gcaacaagct gagcttgctg gaagccgaac aaaggcgtta cagagcacaa     120
acatagtggc agtgtaggaa ctctaactgg gaccaaaact acgggcccgg cagaaacgtt     180
ccccgccccg aagcgaaggc gaacgtcgaa aagcaagacc gggaccgctc gtcccaggat     240
tagccacgaa gttccagacc aagtatagga gtaaacgctc gctcgtcaaa acaattgtca     300
ccaatcagca ccacatcggc acataacaac cggttgcgga actcgcatgt gaacaacaag     360
cggctccggg ggagtgatcg gctcgggcg atgaccggaa ctcttccgcg cagcaactcg     420
gcgtgttgtt gacggcagta ctccgtagtt gccatgacaa cagtcaatgg cgtgcttcac     480
aaggtggaga gccgagaaag cacctcggca tgtacgagta tgtagatagt gtatcaagca     540
ggaagatggg ggttacttta tctcaatcag atgcctgtaa gcgagagccg agagcctgcc     600
ctgttgttga cacaattctg gcctgataac gagtgacaag cgctgggacg gcggctgggg     660
tcttttgctc gcggcttcag ctcaattcca atcctgggcc ggtgccgaac ggcccaatcg     720
cgagcgccca cgaaatcgga ggtcgaggaa agaaggctgg gcgagacgcg gcgacaagct     780
gtggcaaaat ggccaattga ggttctgggt cggctggtga tcaaccatgc atttcccagc     840
ccgcagattc tctttctctc tcgtgcagca gcggcaccag cagcagcagc agccaggggt     900
ttgaccaacc tctccgccca gccaccgata gtaaagatgc tgcctgcgta ttctgggctg     960
caggagttcc aagatctttc ggtctggcca ccagctgtca cgtcaccctc cacctttgga    1020
cgacgttgct ggaaaattcg aagccttcac taagataact atgccgtagc acttgcagcc    1080
```

```
ccggaagctg caagttgatt cttggagggc tctctccacc accaatacgg gagatctggc    1140
cccgcacttg aggaggctgg agtctcggat cgcccacttc gcgtcgccct gggccctggg    1200
ccctggggtg atgggcccgt tgccgtggtg gatggcagga gcttttcagc tctcaatggg    1260
cgaatgctac tccgtaggtc ggagtggctg gaagcggcgg aacggacagg gggaggttgg    1320
ggaaaatgct ccgcaggaag agcagggagt ggggagctgc ggtcggccct gtggagcccg    1380
tgcagggcca gctaatccaa ttcgggccac aataaacaag agagggcccc acatcatgta    1440
aacagaggct cagaagctcc tgccacactg ggagggtttc gaagtctgac gactgccaat    1500
ggaccccagc catcgcgagc acacagcagt tcgcacgctc ccattgggtt cctcatcacg    1560
cagtcgctct ccccgccaac cagcgccagg tccgggaaca gcggcgcaaa tgcgtatttg    1620
agggcgcctc gctcgagcaa cctgtgcctg accttctcct cctccttctg caccttgcat    1680
ctcgtcgcgt ccactcgcag gcaaccacac atcctcctcc tctcccaaaa ccccccgct    1740 tttcttttcc cttgttggaa ttcgattgaa aagaagacg ggtccgtcta gagaccgcct    1800
tctcaccttt ctctcgactt cttttctagga aagaagcaa gagtcattct tcttgtccac    1860
cttctggttc acggaaggtc gaggagaaga ttgcctctgc ccccaaagtc gccaacctgg    1920
actttgaagc acgtgttccg gtcccttca gtgtcttccc gtcctcgtac agggagtccg    1980
agaccgccac ccaaacccac tcccacgaag aggttgagat caagctcccc cagctcgccg    2040
gacgggaagg tcaacactct tcattccaag cccaagcaca tcttcctccc agcggagagg    2100
gtcgcttcag agaagaagag gtccgcatca ctcgtcaaga ggaacatcac cgccgtcccg    2160
gcatccgtga agagttcgtt caccgcgagg agcgtcaccg gtaagtttag ttttttgtttt    2220 gattcaccac ccattgtctt ccccgccttt ttcttttcct tcccttgctc tcttgcccct    2280
gtctagtgta gggcattgcc aaggccatct tcacacacac acccccccc ccccccac      2340 cctcagctgg gggggggggt ggcctgggtt gaccaaggga cggtgaagac tactactact    2400
tgagccactc aaacccatgc atgacacagg gttttccttt ttcttttctc ttttcctta    2460 actaaccaac cactccaaca ttagccctca gtcaacctac tccgagtctc gcatcgagtt    2520
cgatactgag caccgcactc acaactccgt cattgacgtt gctgagagcg agtatcgtgc    2580
ccgtgtccag cccaactacc gcaaggaagc ttccgtagtc ggtaccaccg tcgacggatc    2640
ccgcttcagc cacagccgca aggccagcag caccacctcc acccacaccg acagtacac    2700 cgtcgatccc cctagccacc gccccgtcta caagaaggag tcggttgaag tcgccggtac    2760
cactgttgac ccccctgctc ctcgttcgac ctaccacgag caggtgaaca ttgttgaaga    2820
gaccgttgac gctcaccgtt acgctcctca acccaacaac aacaacacc                2869
```

<210> SEQ ID NO 2  
<211> LENGTH: 1162  
<212> TYPE: DNA  
<213> ORGANISM: Artificial Sequence  
<220> FEATURE:  
<223> OTHER INFORMATION: Promoter

<400> SEQUENCE: 2

```
gactagcagc acgcggcagg attcttcaaa attggctaaa acgcgttggc ggggtgctcc      60
aagctcgagt gtgatcgaat gggagcaaag catcgccgct tgagtcagcc cgggctcggc     120
cattgattgg gggtgcccat gtcagctcaa ggcagcaagc ggatagaagc gccgtgggaa     180
gactagcaac gcctgctctg ggcatggccg ctgaatgtct gctggttctc aacgacgcgg     240
ggaacttgtg caactggagc gaaatatcgg cttggcaggg gctccttcta ctttgggagg     300
```

```
agaactggca tcacccactc ggctctacgg cttgaagatg ccgtgtgtgg caaccaacag    360
gcactgaaaa ttcatgcagg cagaccccgt tctgggaagc aaaatgcagc agcgccttcc    420
ttggctctcg cgagctgtta gtagagcacg aacgaaactc gaccagtttg agggtctatc    480
acgctcccgt accgcaagaa ggatctcatg tagtaggact gagatgtttt ttttcttccc    540
ttcctacttt tttgtgcgct cttgaaggta ttaagaccat cacgatggga tacctacctc    600
ttcaaagcat acatggcacg gcaaccgacc ccccaaacgt taggtagcac gccagcgggc    660
ggatggccca tcgtggaatt cacggtctgg gcccgcggga ggattgcttg cacctgcgtg    720
ataatttcct gggacacccc cctgttcgcg gacagcgagc ccggatgtca acgacagcgg    780
acgcatcgtg gaagcgggtt gccgttctcc ctcccccccc cccccttttc tctccagggg    840
tggccctttt cccttctgag ctggcttggc taagttgggc ctcctcctat gaaaggctgc    900
cgttcccttt gcctccctag ggccgtcttc ttcccgccgc ctccctcttg gttcctgttc    960
aattcaacac cagacggcgt gctctccccg gccgttgcaa acgtcttgtt tgcgtccttt   1020
cgttgtgtgc ttctgccgtt gcagctcatc agtcgctcct ttactacggc ccggccatcc   1080
tcggccattc actcgttttc cgtgtgtgca gacgaacaaa cacatactca ccttgtattg   1140
ttaatatcac gtctcgtcca ta                                            1162
```

<210> SEQ ID NO 3
<211> LENGTH: 51
<212> TYPE: DNA
<213> ORGANISM: Artificial Sequence
<220> FEATURE:
<223> OTHER INFORMATION: Signal sequence

<400> SEQUENCE: 3

```
atgtacgcca agttcgcgac cctcgccgcc cttgtggctg gcgccgctgc t              51
```

<210> SEQ ID NO 4
<211> LENGTH: 548
<212> TYPE: PRT
<213> ORGANISM: Influenza virus

<400> SEQUENCE: 4

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Thr Pro Asn Pro Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Lys Ser Ser Phe Tyr
    130                 135                 140

Arg Asn Leu Leu Trp Leu Thr Gly Lys Asn Gly Leu Tyr Pro Asn Leu
```

```
145                 150                 155                 160
Ser Lys Ser Tyr Val Asn Asn Lys Glu Lys Glu Val Leu Val Leu Trp
                165                 170                 175

Gly Val His His Pro Asn Ile Gly Asn Gln Arg Ala Leu Tyr His
            180                 185                 190

Thr Glu Asn Ala Tyr Val Ser Val Ser Ser His Tyr Ser Arg Arg
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Trp Tyr Ala Phe Ala Leu
                245                 250                 255

Ser Arg Gly Phe Gly Ser Gly Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asn Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Val Lys Leu Glu Ser Met Gly Val Tyr Gln Ile
            500                 505                 510

Leu Ala Ile Tyr Ser Thr Val Ala Ser Ser Leu Val Leu Leu Val Ser
        515                 520                 525

Leu Gly Ala Ile Ser Phe Trp Met Cys Ser Asn Gly Ser Leu Gln Cys
    530                 535                 540

Arg Ile Cys Ile
545

<210> SEQ ID NO 5
```

<211> LENGTH: 1644
<212> TYPE: DNA
<213> ORGANISM: Artificial Sequence
<220> FEATURE:
<223> OTHER INFORMATION: Polynucleotide

<400> SEQUENCE: 5
gacaccatct gcatcggcta ccacgccaac aacagcaccg acaccgtcga cacggtcctc 60
gagaagaacg tcaccgtcac ccacagcgtc aacctgctcg aggacagcca caacggcaag 120
ctctgcctcc tcaagggcat cgcccccctc cagctcggca actgcagcgt cgccggctgg 180
atcctcggca accccgagtg cgagctgctc atcagcaagg agagctggtc gtacatcgtc 240
gagaccccca accccgagaa cggcacgtgc taccccggct acttcgccga ctacgaggag 300
ctgcgcgagc agctcagcag cgtcagctcg ttcgagcgct tcgagatctt ccccaaggag 360
agcagctggc ccaaccacac cgtcaccggc gtcagcgcca gctgctcgca caacggcaag 420
agcagcttct accgcaacct cctctggctc accggcaaga acggcctcta cccgaacctc 480
agcaagagct acgtcaacaa caaggagaag gaggtcctcg tcctctgggg cgtccaccac 540
ccccccaaca tcggcaacca gcgcgccctc taccacaccg agaacgccta cgtcagcgtc 600
gtcagcagcc actacagccg ccgcttcacc cccgagatcg ccaagcgccc caaggtccgc 660
gaccaggagg gccgcatcaa ctactactgg accctcctcg agcccggcga caccatcatc 720
ttcgaggcca acggcaacct gatcgccccc tggtacgcct tcgccctcag ccgcggcttc 780
ggcagcggca tcatcaccag caacgccccc atggacgagt gcgacgccaa gtgccagacc 840
ccccagggcg ccatcaacag cagcctcccg ttccagaacg tccaccccgt caccatcggc 900
gagtgcccca agtacgtccg cagcgccaag ctccgcatgg tcaccggcct ccgcaacatc 960
cccagcatcc agagccgcgg cctcttcggc gccatcgccg gcttcatcga gggcggctgg 1020
accggcatgg tcgacggctg gtacggctac caccaccaga acgagcaggg cagcggctac 1080
gccgccgacc agaagtcgac ccagaacgcc atcaacggca tcaccaacaa ggtcaacagc 1140
gtcatcgaga agatgaacac ccagttcacc gccgtcggca aggagttcaa caagctcgag 1200
cgccgcatgg agaacctcaa caagaaggtc gacgacggct tcctcgacat ctggacctac 1260
aacgccgagc tgctcgtcct cctcgagaac gagcgcaccc tcgacttcca cgacagcaac 1320
gtcaagaacc tgtacgagaa ggtcaagagc cagctcaaga acaacgccaa ggagatcggc 1380
aacggctgct tcgagttcta ccacaagtgc aacaacgagt gcatggagag cgtcaagaac 1440
ggcacctacg actaccccaa gtacagcgag gagagcaagc tcaaccgcga gaagatcgac 1500
ggcgtcaagc tcgagagcat gggcgtctac cagatcctcg ccatctacag caccgtcgcc 1560
agcagcctcg tcctcctggt cagcctcggc gccatctcgt tctggatgtg cagcaacggc 1620
agcctccagt gccgcatctg catc 1644

<210> SEQ ID NO 6
<211> LENGTH: 550
<212> TYPE: PRT
<213> ORGANISM: Influenza virus

<400> SEQUENCE: 6

Gln Lys Leu Pro Gly Asn Asp Asn Ser Thr Ala Thr Leu Cys Leu Gly
1 5 10 15

His His Ala Val Pro Asn Gly Thr Ile Val Lys Thr Ile Thr Asn Asp
20 25 30

Arg Ile Glu Val Thr Asn Ala Thr Glu Leu Val Gln Asn Ser Ser Ile

```
                35                  40                  45
Gly Glu Ile Cys Asp Ser Pro His Gln Ile Leu Asp Gly Glu Asn Cys
 50                  55                  60

Thr Leu Ile Asp Ala Leu Leu Gly Asp Pro Gln Cys Asp Gly Phe Gln
 65                  70                  75                  80

Asn Lys Lys Trp Asp Leu Phe Val Glu Arg Ser Lys Ala Tyr Ser Asn
                 85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Asn Asn Glu Ser Phe Asn Trp Asn
            115                 120                 125

Gly Val Thr Gln Asn Gly Thr Ser Ser Ala Cys Ile Arg Arg Ser Asn
        130                 135                 140

Asn Ser Phe Phe Ser Arg Leu Asn Trp Leu Thr His Leu Asn Phe Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Gly Thr Asp Lys Asp Gln Ile
            180                 185                 190

Phe Leu Tyr Ala Gln Pro Ser Gly Arg Ile Thr Val Ser Thr Lys Arg
        195                 200                 205

Ser Gln Gln Ala Val Ile Pro Asn Ile Gly Ser Arg Pro Arg Ile Arg
    210                 215                 220

Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Lys Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Ser Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460
```

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
        530                 535                 540

Arg Cys Asn Ile Cys Ile
545                 550

<210> SEQ ID NO 7
<211> LENGTH: 1650
<212> TYPE: DNA
<213> ORGANISM: Artificial Sequence
<220> FEATURE:
<223> OTHER INFORMATION: Polynucleotide

<400> SEQUENCE: 7
caaaaacttc ctggaaatga caatagcacg gcaacgctgt gccttgggca ccatgcagta      60
ccaaacggaa cgatagtgaa acaatcacg aatgaccgaa ttgaagttac taatgctact     120
gaactggttc agaattcctc aataggtgaa atatgcgaca gtcctcatca gatccttgat     180
ggagaaaact gcacactaat agatgctcta ttgggagacc ctcagtgtga tggcttccaa     240
aataagaaat gggaccttt tgttgaacga agcaaagcct acagcaactg ttaccctta     300 gatgtgccgg attatgcctc ccttaggtca ctagttgcct catccggcac actggagttt     360
aacaatgaaa gcttcaattg gaatggagtc actcaaaacg gaacaagttc tgcttgcata     420
aggagatcta ataatagttt ctttagtaga ttaaattggt tgacccactt aaacttcaaa     480
tacccagcat tgaacgtgac tatgccaaac aatgaacaat ttgacaaatt gtacatttgg     540
ggggttcacc acccgggtac ggacaaggac caaatcttcc tgtatgctca accatcagga     600
agaatcacag tatctaccaa agaagccaa caagctgtaa tcccgaatat cggatctaga     660
cccagaataa ggaatatccc tagcagaata agcatctatt ggacaatagt aaaaccggga     720
gacatacttt tgattaacag cacagggaat ctaattgctc ctaggggtta cttcaaaata     780
cgaagtggga aaagctcaat aatgagatca gatgcaccca ttggcaaatg caagtctgaa     840
tgcatcactc caaatggaag cattcccaat gacaaaccat tccaaaatgt aaacaggatc     900
acatacgggg cctgtcccag atatgttaag caaagcactc tgaaattggc aacaggaatg     960
cggaatgtac cagagaaaca aactagaggc atatttggcg caatagcggg tttcatagaa    1020
aatggttggg agggaatggt ggatggttgg tacggtttca ggcatcaaaa ttctgaggga    1080
agaggacaag cagcagatct caaaagcact caagcagcaa tcgatcaaat caatgggaag    1140
ctgaatcgat tgatcgggaa accaacgag aaattccatc agattgaaaa agaattctca    1200
gaagtagaag ggagaattca ggaccttgag aaatatgttg aggacactaa aatagatctc    1260
tggtcataca acgcggagct tcttgttgcc ctggagaacc aacatacaat tgatctaact    1320
gactcagaaa tgaacaaact gtttgaaaaa acaagaagc aactgaggga aaatgctgag    1380
gatatgggca atggttgttt caaaatatac cacaaatgtg acaatgcctg cataggatca    1440
atcagaaatg gaacttatga ccacgatgta tacagagatg aagcattaaa caaccggttc    1500

```
cagatcaagg gagttgagct gaagtcaggg tacaaagatt ggatcctatg gatttccttt   1560
gccatatcat gtttttgct ttgtgttgct ttgttggggt tcatcatgtg ggcctgccaa   1620
aagggcaaca ttaggtgcaa catttgcatt                                    1650

<210> SEQ ID NO 8
<211> LENGTH: 548
<212> TYPE: PRT
<213> ORGANISM: Influenza virus

<400> SEQUENCE: 8

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Asn Thr
        115                 120                 125

Asn Gly Val Thr Ala Ala Cys Ser His Glu Gly Lys Ser Ser Phe Tyr
    130                 135                 140

Arg Asn Leu Leu Trp Leu Thr Glu Lys Glu Gly Ser Tyr Pro Lys Leu
145                 150                 155                 160

Lys Asn Ser Tyr Val Asn Lys Lys Gly Lys Glu Val Leu Val Leu Trp
                165                 170                 175

Gly Ile His His Pro Pro Asn Ser Lys Glu Gln Gln Asn Leu Tyr Gln
            180                 185                 190

Asn Glu Asn Ala Tyr Val Ser Val Val Thr Ser Asn Tyr Asn Arg Arg
        195                 200                 205

Phe Thr Pro Glu Ile Ala Glu Arg Pro Lys Val Arg Asp Gln Ala Gly
    210                 215                 220

Arg Met Asn Tyr Tyr Trp Thr Leu Leu Lys Pro Gly Asp Thr Ile Ile
225                 230                 235                 240

Phe Glu Ala Asn Gly Asn Leu Ile Ala Pro Met Tyr Ala Phe Ala Leu
                245                 250                 255

Ser Arg Gly Phe Gly Ser Gly Ile Ile Thr Ser Asn Ala Ser Met His
            260                 265                 270

Glu Cys Asn Thr Lys Cys Gln Thr Pro Leu Gly Ala Ile Asn Ser Ser
        275                 280                 285

Leu Pro Tyr Gln Asn Ile His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Ile Asp Gly Trp Tyr Gly Tyr His His
            340                 345                 350
```

| | | | | | | | | | | | | |
|---|---|---|---|---|---|---|---|---|---|---|---|---|
|Gln|Asn|Glu|Gln|Gly|Ser|Gly|Tyr|Ala|Ala|Asp|Gln|Lys|Ser|Thr|Gln|
| | |355| | | |360| | | |365| | |

Gln Asn Glu Gln Gly Ser Gly Tyr Ala Ala Asp Gln Lys Ser Thr Gln
          355                    360                  365

Asn Ala Ile Asn Gly Ile Thr Asn Lys Val Asn Thr Val Ile Glu Lys
   370                    375                    380

Met Asn Ile Gln Phe Thr Ala Val Gly Lys Glu Phe Asn Lys Leu Glu
385                    390                    395                400

Lys Arg Met Glu Asn Leu Asn Lys Lys Val Asp Asp Gly Phe Leu Asp
            405                    410                415

Ile Trp Thr Tyr Asn Ala Glu Leu Leu Val Leu Leu Glu Asn Glu Arg
        420                    425                430

Thr Leu Asp Phe His Asp Ser Asn Val Lys Asn Leu Tyr Glu Lys Val
            435                    440                445

Lys Ser Gln Leu Lys Asn Asn Ala Lys Glu Ile Gly Asn Gly Cys Phe
   450                    455                    460

Glu Phe Tyr His Lys Cys Asp Asn Glu Cys Met Glu Ser Val Arg Asn
465                    470                    475                480

Gly Thr Tyr Asp Tyr Pro Lys Tyr Ser Glu Glu Ser Lys Leu Asn Arg
                  485                    490                495

Glu Lys Val Asp Gly Val Lys Leu Glu Ser Met Gly Ile Tyr Gln Ile
            500                    505                510

Leu Ala Ile Tyr Ser Thr Val Ala Ser Ser Leu Val Leu Leu Val Ser
        515                    520                525

Leu Gly Ala Ile Ser Phe Trp Met Cys Ser Asn Gly Ser Leu Gln Cys
            530                    535                540

Arg Ile Cys Ile
545

<210> SEQ ID NO 9
<211> LENGTH: 1647
<212> TYPE: DNA
<213> ORGANISM: Artificial Sequence
<220> FEATURE:
<223> OTHER INFORMATION: Polynucleotide

<400> SEQUENCE: 9

```
gacacaatat gtataggcta ccatgcgaac aattcaaccg acactgttga cacagtactc      60
gagaagaatg tgacagtgac acactctgtt aacctgctcg aagacagcca acggaaaa      120 ctatgtagat taaaggaat agccccacta caattgggga atgtaacat cgccggatgg       180 ctcttgggaa acccagaatg cgaccccactg cttccagtga gatcatggtc ctacattgta    240
gaaacaccaa actctgagaa tggaatatgt tatccaggag atttcatcga ctatgaggag     300
ctgagggagc aattgagctc agtgtcatca ttcgaaagat cgaaatatt tcccaaagaa     360 agctcatggc ccaaccacaa cacaaacgga gtaacggcag catgctccca tgaggggaaa     420
agcagttttt acagaaattt gctatggctg acggagaagg agggctcata cccaaagctg    480
aaaaattctt atgtgaacaa aaagggaaa gaagtccttg tactgtgggg tattcatcac      540
ccgcctaaca gtaaggaaca acagaatctc tatcagaatg aaaatgctta tgtctctgta    600
gtgacttcaa attataacag agatttacc ccggaaatag cagaaagacc aaagtaaga     660 gatcaagctg ggaggatgaa ctattactgg accttgctaa acccggaga cacaataata     720 tttgaggcaa atggaaatct aatagcacca atgtatgctt cgcactgag tagaggcttt     780 gggtccggca tcatcacctc aaacgcatca atgcatgagt gtaacacgaa gtgtcaaaca     840
cccctgggag ctataaacag cagtctccct taccagaata tacccagt cacaatagga      900
```

-continued

```
gagtgcccaa aatacgtcag gagtgccaaa ttgaggatgg ttacaggact aaggaacatt    960
ccgtccattc aatccagagg tctatttgga gccattgccg gttttattga aggggatgg    1020 actggaatga tagatggatg gtatggttat catcatcaga atgaacaggg atcaggctat   1080
gcagcggatc aaaaaagcac acaaaatgcc attaacggga ttacaaacaa ggtgaacact   1140
gttatcgaga aaatgaacat tcaattcaca gctgtgggta agaattcaa caaattagaa    1200 aaaaggatgg aaaatttaaa taaaaaagtt gatgatggat ttctggacat ttggacatat   1260
aatgcagaat tgttagttct actggaaaat gaaaggactc tggatttcca tgactcaaat   1320
gtgaagaatc tgtatgagaa agtaaaaagc caattaaaga ataatgccaa agaaatcgga   1380
aatggatgtt ttgagttcta ccacaagtgt gacaatgaat gcatggaaag tgtaagaaat   1440
gggacttatg attatcccaa atattcgaaa gagtcaaagt tgaacaggga aaagtagat    1500 ggagtgaaat tggaatcaat ggggatctat cagattctgg cgatctactc aactgtcgcc   1560
agttcactgg tgcttttggt ctccctgggg gcaatcagtt tctggatgtg ttctaatgga   1620
tctttgcagt gcagaatatg catctga                                      1647
```

<210> SEQ ID NO 10
<211> LENGTH: 569
<212> TYPE: PRT
<213> ORGANISM: Influenza virus

<400> SEQUENCE: 10

```
Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Gly Ser Cys Pro
    130                 135                 140

Asn Ala Thr Ser Lys Ser Gly Phe Phe Ala Thr Met Ala Trp Ala Val
145                 150                 155                 160

Pro Lys Asp Asn Asn Lys Asn Ala Thr Asn Pro Leu Thr Val Glu Val
                165                 170                 175

Pro Tyr Ile Cys Thr Glu Gly Glu Asp Gln Ile Thr Val Trp Gly Phe
            180                 185                 190

His Ser Asp Asp Lys Thr Gln Met Lys Asn Leu Tyr Gly Asp Ser Asn
        195                 200                 205

Pro Gln Lys Phe Thr Ser Ser Ala Asn Gly Val Thr Thr His Tyr Val
    210                 215                 220

Ser Gln Ile Gly Ser Phe Pro Asp Gln Thr Glu Asp Gly Gly Leu Pro
225                 230                 235                 240
```

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Lys Tyr Gly Gly Leu Asn Lys
    290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg Gly Phe Phe Gly Ala Ile
            340                 345                 350

Ala Gly Phe Leu Glu Gly Gly Trp Glu Gly Met Ile Ala Gly Trp His
        355                 360                 365

Gly Tyr Thr Ser His Gly Ala His Gly Val Ala Val Ala Ala Asp Leu
    370                 375                 380

Lys Ser Thr Gln Glu Ala Ile Asn Lys Ile Thr Lys Asn Leu Asn Ser
385                 390                 395                 400

Leu Ser Glu Leu Glu Val Lys Asn Leu Gln Arg Leu Ser Gly Ala Met
                405                 410                 415

Asp Glu Leu His Asn Glu Ile Leu Glu Leu Asp Glu Lys Val Asp Asp
            420                 425                 430

Leu Arg Ala Asp Thr Ile Ser Ser Gln Ile Glu Leu Ala Val Leu Leu
        435                 440                 445

Ser Asn Glu Gly Ile Ile Asn Ser Glu Asp Glu His Leu Leu Ala Leu
450                 455                 460

Glu Arg Lys Leu Lys Lys Met Leu Gly Pro Ser Ala Val Glu Ile Gly
465                 470                 475                 480

Asn Gly Cys Phe Glu Thr Lys His Lys Cys Asn Gln Thr Cys Leu Asp
                485                 490                 495

Arg Ile Ala Ala Gly Thr Phe Asn Ala Gly Glu Phe Ser Leu Pro Thr
            500                 505                 510

Phe Asp Ser Leu Asn Ile Thr Ala Ala Ser Leu Asn Asp Asp Gly Leu
        515                 520                 525

Asp Asn His Thr Ile Leu Leu Tyr Tyr Ser Thr Ala Ala Ser Ser Leu
    530                 535                 540

Ala Val Thr Leu Met Leu Ala Ile Phe Ile Val Tyr Met Val Ser Arg
545                 550                 555                 560

Asp Asn Val Ser Cys Ser Ile Cys Leu
                565

<210> SEQ ID NO 11
<211> LENGTH: 1707
<212> TYPE: DNA
<213> ORGANISM: Artificial Sequence
<220> FEATURE:
<223> OTHER INFORMATION: Polynucleotide

<400> SEQUENCE: 11
gatcgaatct gcactggaat aacatcttca aactcacctc atgtggtcaa acagccact      60 caaggggagg tcaatgtgac tggtgtgata ccactaacaa caacaccaac aaaatcttat     120
tttgcaaatc tcaaaggaac aaggaccaga gggaaactat gcccagactg tctcaactgc    180

```
acagatctgg atgtggcttt gggcagacca atgtgtgtgg ggaccacacc ttcggcgaaa    240
gcttcaatac tccacgaagt caaacctgtt acatccgggt gctttcctat aatgcacgac    300
agaacaaaaa tcaggcaact acccaatctt ctcagaggat atgaaaatat caggctatca    360
acccaaaacg tcatcgatgc ggaaaaggca ccaggaggac cctacagact tggaacctca    420
ggatcttgcc ctaacgctac cagtaagagc ggattttcg caacaatggc ttgggctgtc     480
ccaaaggaca caacaaaaa tgcaacgaac ccactaacag tagaagtacc atacatttgt     540
acagaagggg aagaccaaat cactgttgg gggttccatt cagatgacaa acccaaatg      600 aagaacctct atggagactc aaatcctcaa aagttcacct catctgctaa tggagtaacc    660
acacactatg tttctcagat tggcagcttc ccagatcaaa cagaagacgg aggactacca    720
caaagcggca ggattgttgt tgattacatg atgcaaaaac ctgggaaaac aggaacaatt    780
gtctaccaaa gaggtgtttt gttgcctcaa aaggtgtggt gcgcgagtgg caggagcaaa    840
gtaataaaag ggtccttgcc tttaattggt gaagcagatt gccttcatga aaaatacggt    900
ggattaaaca aaagcaagcc ttactacaca ggagaacatg caaaagccat ggaaattgc     960 ccaatatggg tgaaaacacc tttgaagctt gccaatggaa ccaaatatag acctcctgca   1020
aaactattaa aggaaggggg tttcttcgga gctattgctg gtttcctaga aggaggatgg   1080
gaaggaatga ttgcaggctg gcacggatac acatctcacg gagcacatgg agtggcagtg   1140
gcggcggacc ttaagagtac gcaagaagct ataaacaaga taacaaaaaa tctcaattct   1200
ttgagtgagc tagaagtaaa gaatcttcaa agactaagtg gtgccatgga tgaactccac   1260
aacgaaatac tcgagctgga tgagaaagtg gatgatctca gagctgacac tataagctcg   1320
caaatagaac ttgcagtctt gctttccaac gaaggaataa taaacagtga agatgagcat   1380
ctattggcac ttgagagaaa actaagaaa atgctgggtc cctctgctgt agagatagga   1440
aatggatgct tcgaaaccaa acacaagtgc aaccagacct gcttagacag gatagctgct   1500 ggcacctta tgcaggaga atttctctc cccactttg attcactgaa cattactgct         1560
gcatctttaa atgatgatgg attggataac catactatac tgctctatta ctcaactgct   1620
gcttctagtt tggctgtaac attgatgcta gctattttta ttgtttatat ggtctccaga   1680
gacaacgttt catgctccat ctgtcta                                        1707
```

<210> SEQ ID NO 12
<211> LENGTH: 549
<212> TYPE: PRT
<213> ORGANISM: Influenza virus

<400> SEQUENCE: 12

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

-continued

Asp Tyr Glu Glu Leu Arg Glu Gln Leu Ser Ser Val Ser Ser Phe Glu
                100                 105                 110

Arg Phe Glu Ile Phe Pro Lys Thr Ser Ser Trp Pro Asn His Asp Ser
            115                 120                 125

Asn Lys Gly Val Thr Ala Ala Cys Pro His Ala Gly Ala Lys Ser Phe
        130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
        210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
        290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Glu Ile Thr Asn Lys Val Asn Ser Val Ile Glu
        370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Ser Gln Leu Lys Asn Asn Ala Lys Glu Ile Gly Asn Gly Cys
        450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Glu Ile Asp Gly Val Lys Leu Glu Ser Thr Arg Ile Tyr Gln
            500                 505                 510

Ile Leu Ala Ile Tyr Ser Thr Val Ala Ser Ser Leu Val Leu Val Val 515                 520                 525
    Ser Leu Gly Ala Ile Ser Phe Trp Met Cys Ser Asn Gly Ser Leu Gln
              530                 535                 540
    Cys Arg Ile Cys Ile
    545

<210> SEQ ID NO 13
<211> LENGTH: 1590
<212> TYPE: DNA
<213> ORGANISM: Artificial Sequence
<220> FEATURE:
<223> OTHER INFORMATION: Polynucleotide

<400> SEQUENCE: 13
gacacattat gtataggtta tcatgcgaac aattcaacag acactgtaga cacagtacta      60
gaaaagaatc taagaggggt agccccattg catttgggta aatgtaacat tgctggctgg     120
atcctgggaa atccagagtg tgaatcactc tccacagcaa gctcatggtc ctacattgtg     180
gaaacaccta gttcagacaa tggaacgtgt acccaggag atttcatcga ttatgaggag      240
ctaagagagc aattgagctc agtgtcatca tttgaaaggt ttgagatatt ccccaagaca     300
agttcatggc ccaatcatga ctcgaacaaa ggtgtaacgg cagcatgtcc tcatgctgga     360
gcaaaaagct tctacaaaaa tttaatatgg ctagttaaaa aaggaaattc atacccaaag     420
ctcagcaaat cctacattaa tgataaaggg aagaagtcc tcgtgctatg ggcattcac      480
catccatcta ctagtgctga ccaacaaagt ctctatcaga atgcagatgc atatgttttt     540
gtggggtcat caagatacag caagaagttc aagccggaaa tagcaataag acccaaagtg     600
agggatcaag aagggagaat gaactattac tggacactag tagagccggg agacaaaata     660
acattcgaag caactggaaa tctagtggta ccgagatatg cattcgcaat ggaaagaaat     720
gctggatctg gtattatcat ttcagataca ccagtccacg attgcaatac aacttgtcaa     780
acacccaagg gtgctataaa caccagcctc ccatttcaga atatacatcc gatcacaatt     840
ggaaaatgtc caaaatatgt aaaaagcaca aaattgagac tggccacagg attgaggaat     900
atcccgtcta ttcaatctag aggcctattt ggggccattg ccggtttcat gaagggggg      960
tggacaggga tggtagatgg atggtacggt tatcaccatc aaaatgagca ggggtcagga    1020
tatgcagccg acctgaagag cacacagaat gccattgacg agattactaa caaagtaaat    1080
tctgttattg aaaagatgaa tacacagttc acagcagtag gtaaagagtt caaccacctg    1140
gaaaaaagaa tagagaattt aaataaaaaa gttgatgatg gtttcctgga catttggact    1200
tacaatgccg aactgttggt tctattggaa aatgaaagaa ctttggacta ccacgattca    1260
aatgtgaaga acttatatga aaaggtaaga agccagctaa aaacaatgc caaggaaatt    1320
ggaaacggct gctttgaatt ttaccacaaa tgcgataaca cgtgcatgga aagtgtcaaa    1380
aatgggactt atgactaccc aaaatactca gaggaagcaa aattaaacag agaagaaata    1440
gatggggtaa agctggaatc aacaaggatt taccagattt ggcgatcta ttcaactgtc    1500
gccagttcat tggtactggt agtctccctg ggggcaatca gtttctggat gtgctctaat    1560
gggtctctac agtgtagaat atgtattaa                                       1590

<210> SEQ ID NO 14
<211> LENGTH: 470
<212> TYPE: PRT
<213> ORGANISM: Influenza virus

<400> SEQUENCE: 14

```
Met Asn Pro Asn Gln Lys Ile Ile Thr Ile Gly Ser Ile Ser Ile Ala
1               5                   10                  15
Ile Gly Ile Ile Ser Leu Met Leu Gln Ile Gly Asn Ile Ile Ser Ile
            20                  25                  30
Trp Ala Ser His Ser Ile Gln Thr Gly Ser Gln Asn His Thr Gly Val
        35                  40                  45
Cys Asn Gln Arg Ile Ile Thr Tyr Glu Asn Ser Thr Trp Val Asn His
    50                  55                  60
Thr Tyr Val Asn Ile Asn Asn Thr Asn Val Val Ala Gly Lys Asp Lys
65                  70                  75                  80
Thr Ser Val Thr Leu Ala Gly Asn Ser Ser Leu Cys Ser Ile Ser Gly
                85                  90                  95
Trp Ala Ile Tyr Thr Lys Asp Asn Ser Ile Arg Ile Gly Ser Lys Gly
                100                 105                 110
Asp Val Phe Val Ile Arg Glu Pro Phe Ile Ser Cys Ser His Leu Glu
            115                 120                 125
Cys Arg Thr Phe Phe Leu Thr Gln Gly Ala Leu Leu Asn Asp Lys His
    130                 135                 140
Ser Asn Gly Thr Val Lys Asp Arg Ser Pro Tyr Arg Ala Leu Met Ser
145                 150                 155                 160
Cys Pro Leu Gly Glu Ala Pro Ser Pro Tyr Asn Ser Lys Phe Glu Ser
                165                 170                 175
Val Ala Trp Ser Ala Ser Ala Cys His Asp Gly Met Gly Trp Leu Thr
                180                 185                 190
Ile Gly Ile Ser Gly Pro Asp Asn Gly Ala Val Ala Val Leu Lys Tyr
                195                 200                 205
Asn Gly Ile Ile Thr Glu Thr Ile Lys Ser Trp Lys Lys Arg Ile Leu
                210                 215                 220
Arg Thr Gln Glu Ser Glu Cys Val Cys Val Asn Gly Ser Cys Phe Thr
225                 230                 235                 240
Ile Met Thr Asp Gly Pro Ser Asn Gly Ala Ala Ser Tyr Lys Ile Phe
                245                 250                 255
Lys Ile Glu Lys Gly Lys Val Thr Lys Ser Ile Glu Leu Asn Ala Pro
                260                 265                 270
Asn Phe His Tyr Glu Glu Cys Ser Cys Tyr Pro Asp Thr Gly Thr Val
                275                 280                 285
Met Cys Val Cys Arg Asp Asn Trp His Gly Ser Asn Arg Pro Trp Val
    290                 295                 300
Ser Phe Asn Gln Asn Leu Asp Tyr Gln Ile Gly Tyr Ile Cys Ser Gly
305                 310                 315                 320
Val Phe Gly Asp Asn Pro Arg Pro Lys Asp Gly Glu Gly Ser Cys Asn
                325                 330                 335
Pro Val Thr Val Asp Gly Ala Asp Gly Val Lys Gly Phe Ser Tyr Lys
                340                 345                 350
Tyr Gly Asn Gly Val Trp Ile Gly Arg Thr Lys Ser Asn Arg Leu Arg
                355                 360                 365
Lys Gly Phe Glu Met Ile Trp Asp Pro Asn Gly Trp Thr Asp Thr Asp
    370                 375                 380
Ser Asp Phe Ser Val Lys Gln Asp Val Val Ala Ile Thr Asp Trp Ser
385                 390                 395                 400
Gly Tyr Ser Gly Ser Phe Val Gln His Pro Glu Leu Thr Gly Leu Asp
                405                 410                 415
```

```
Cys Ile Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465             470

<210> SEQ ID NO 15
<211> LENGTH: 1410
<212> TYPE: DNA
<213> ORGANISM: Artificial Sequence
<220> FEATURE:
<223> OTHER INFORMATION: Polynucleotide

<400> SEQUENCE: 15
atgaatccaa atcaaaaaat aataaccatt ggatcaatca gtatagcaat cggaataatt      60
agtctaatgt tgcaaatagg aaatattatt tcaatatggg ctagtcactc aatccaaact     120
ggaagtcaaa accacactgg agtatgcaac caaagaatca tcacatatga aaacagcacc     180
tgggtgaatc acacatatgt taatattaac aacactaatg ttgttgctgg aaaggacaaa     240
acttcagtga cattggccgg caattcatct ctttgttcta tcagtggatg gctatatac      300 acaaaagaca cagcataag aattggctcc aaggagatg ttttgtcat aagagaacct        360 ttcatatcat gttctcactt ggaatgcaga acctttttc tgacccaagg tgctctatta     420
aatgacaaac attcaaatgg gaccgttaag gacagaagtc cttatagggc cttaatgagc    480
tgtcctctag gtgaagctcc gtccccatac aattcaaagt ttgaatcagt tgcatggtca    540
gcaagcgcat gccatgatgg catgggctgg ttaacaatcg gaatttctgg tccagacaat    600
ggagctgtgg ctgtactaaa atacaacggc ataataactg aaaccataaa agttggaaaa    660 agcgaatat taagaacaca agagtctgaa tgtgtctgtg tgaacgggtc atgtttcacc     720
ataatgaccg atggcccgag taatgggcc gcctcgtaca aaatcttcaa gatcgaaaag    780
gggaaggtta ctaaatcaat agagttgaat gcacccaatt ttcattatga ggaatgttcc   840
tgttacccag acactggcac agtgatgtgt gtatgcaggg acaactggca tggttcaaat    900
cgaccttggg tgtcttttaa tcaaaacctg gattatcaaa taggatacat ctgcagtggg    960
gtgttcggtg acaatccgcg tcccaaagat ggagagggca gctgtaatcc agtgactgtt   1020
gatggagcag acgagtaaa ggggttttca tacaaatatg gtaatggtgt ttggataggaa   1080 aggactaaaa gtaacagact agaaagggg tttgagatga tttgggatcc taatggatgg    1140
acagataccg acagtgattt ctcagtgaaa caggatgttg tggcaataac tgattggtca    1200
gggtacagcg gaagtttcgt tcaacatcct gagttaacag gattggactg tataagacct    1260
tgcttctggg ttgagttagt cagaggactg cctagagaaa atacaacaat ctggactagt    1320
gggagcagca tttcttttg tggcgtaaat agtgatactg caaactggtc ttggccagac    1380
ggtgctgagt tgccgttcac cattgacaag                                     1410

<210> SEQ ID NO 16
<211> LENGTH: 5589
<212> TYPE: DNA
<213> ORGANISM: Artificial Sequence
<220> FEATURE:
<223> OTHER INFORMATION: Polynucleotide
<220> FEATURE:
<221> NAME/KEY: misc_feature
```

<222> LOCATION: (4774)..(4774)
<223> OTHER INFORMATION: n is a, c, g, or t

<400> SEQUENCE: 16

```
ggccgctcta gaactagtac ggcgtgcaag tagtgtcttt ctttgcactc ccgccgtccc        60
agaagacgcc gcaacaagct gagcttgctg gaagccgaac aaaggcgtta cagagcacaa       120
acatagtggc agtgtaggaa ctctaactgg gaccaaaact acgggcccgg cagaaacgtt       180
ccccgccccg aagcgaaggc gaacgtcgaa agcaagacc gggaccgctc gtcccaggat        240
tagccacgaa gttccagacc aagtatagga gtaaacgctc gctcgtcaaa acaattgtca       300
ccaatcagca ccacatcggc acataacaac cggttgcgga actcgcatgt gaacaacaag       360
cggctccggg ggagtgatcg gctcgggcgg atgacccgga ctcttccgcg cagcaactcg       420
gcgtgttgtt gacggcagta ctccgtagtt gccatgacaa cagtcaatgg cgtgcttcac       480
aaggtggaga gccgagaaag cacctcggca tgtacgagta tgtagatagt gtatcaagca       540
ggaagatggg ggttacttta tctcaatcag atgcctgtaa gcgagagccg agagcctgcc       600
ctgttgttga cacaattctg gcctgatacg agtgacaagc gctgggacgg cggctggggt       660
cttttgctcg cggcttcagc tcaattccaa tcctgggccg gtgccgaacg gcccaatcgc       720
gagcgcccac gaaatcggag gtcgaggaaa gaaggctggg cgagacgcgg cgacaagctg       780
tggcaaaatg gccaattgag gttctgggtc ggctggtgat caaccatgca tttcccagcc       840
cgcagattct ctttctctct cgtgcagcag cggcaccagc agcagcagca gccaggggtt       900
tgaccaacct ctccgcccag ccaccgatag taaagatgct gcctgcgtat tctgggctgc       960
aggagttcca agatctttcg gtctggccac cagctgtcac gtcaccctcc acctttggac      1020
gacgttgctg gaaaattcga agccttcact aagataacta tgcctagca cttgcagccc       1080
cggaagctgc aagttgattc ttggagggct ctctccacca ccaatacggg agatctggcc      1140
ccgcacttga ggaggctgga gtctcggatc gcccacttcg cgtcgccctg ggccctgggc      1200
cctggggtga tgggcccgtt gccgtggtgg atggcaggag cttttcagct ctcaatgggc      1260
gaatgctact ccgtaggtcg gagtggctgg aagcggcgga acggacaggg ggaggttggg      1320
gaaaatgctc cgcaggaaga gcaggagtg gggagctgcg gtcggccctg tggagcccgt       1380
gcagggccag ctaatccaat tcgggccaca ataaacaaga gagggcccca catcatgtaa      1440
acagaggctc agaagctcct gccacactgg gagggtttcg aagtctgacg actgccaatg      1500
gaccccagcc atcgcgagca cacagcagtt cgcacgctcc cattgggttc ctcatcacgc      1560
agtcgctctc cccgccaacc agcgccaggt ccgggaacag cggcgcaaat gcgtatttga      1620
gggcgcctcg ctcgagcaac ctgtgcctga ccttctcctc ctccttctgc accttgcatc      1680
tcgtcgcgtc cactcgcagg caaccacaca tcctcctcct ctcccaaaac ccccccgctt     1740
tttctttccc ttgttggaat tcgattgaaa agaagacgg gtccgtctag accgccttt        1800
ctcacctttc tctcgacttc tttctaggaa agaagcaag agtcattctt cttgtccacc      1860
ttctggttca cggaaggtcg aggagaagat tgcctctgcc cccaaagtcg ccaacctgga      1920
ctttgaagca cgtgttccgg tccctttcag tgtcttcccg tcctcgtaca gggagtccga     1980
gaccgccacc caaacccact cccacgaaga ggttgagatc aagctccccc agctcgccgg     2040
acgggaaggt caacactctt cattccaagc ccaagcacat cttcctccca gcggagaggg    2100
tcgcttcaga gaagaagagg tccgcatcac tcgtcaagag gaacatcacc gccgtcccgg    2160
catccgtgaa gagttcgttc accgcgagga gcgtcaccgg taagtttagt ttttgttttg    2220
```

```
attcaccacc cattgtcttc cccgcctttt tcttttcctt cccttgctct cttgcccctg    2280
tctagtgtag ggcattgcca aggccatctt cacacacaca caccccccc ccccccacc     2340 ctcagctggg gggggggtg gcctgggttg accaagggac ggtgaagact actactactt    2400
gagccactca aacccatgca tgacacaggg ttttccttt tcttttctct tttcctttaa    2460
ctaaccaacc actccaacat tagccctcag tcaacctact ccgagtctcg catcgagttc   2520
gatactgagc accgcactca caactccgtc attgacgttg ctgagagcga gtatcgtgcc   2580
cgtgtccagc ccaactaccg caaggaagct tccgtagtcg gtaccaccgt cgacggatcc   2640
cgcttcagcc acagccgcaa ggccagcagc accacctcca cccacaccga cgagtacacc   2700
gtcgatcccc ctagccaccg ccccgtctac aagaaggagt cggttgaagt cgccggtacc   2760
actgttgacc cccctgctcc tcgttcgacc taccacgagc aggtgaacat tgttgaagag   2820
accgttgacg ctcaccgtta cgctcctcaa cccaacaaca caacaccat gtacgccaag    2880 ttcgcgaccc tcgccgccct tgtggctggc gccgctgctg acaccatctg catcggctac   2940
cacgccaaca acagcaccga caccgtcgac acggtcctcg agaagaacgt caccgtcacc   3000
cacagcgtca acctgctcga ggacagccac aacggcaagc tctgcctcct caagggcatc   3060 gccccctcc agctcggcaa ctgcagcgtc gccggctgga tcctcggcaa ccccgagtgc   3120
gagctgctca tcagcaagga gagctggtcg tacatcgtcg agaccccaa ccccgagaac    3180 ggcacgtgct acccccggcta cttcgccgac tacgaggagc tgcgcgagca gctcagcagc   3240
gtcagctcgt tcgagcgctt cgagatcttc cccaaggaga gcagctggcc caaccacacc    3300
gtcaccggcg tcagcgccag ctgctcgcac aacggcaaga gcagcttcta ccgcaacctc   3360
ctctggctca ccggcaagaa cggcctctac ccgaacctca gcaagagcta cgtcaacaac   3420
aaggagaagg aggtcctcgt cctctggggc gtccaccacc ccccaacat cggcaaccag    3480 cgcgccctct accacaccga gaacgcctac gtcagcgtcg tcagcagcca ctacagccgc   3540
cgcttcaccc ccgagatcgc caagcgcccc aaggtccgcg accaggaggg ccgcatcaac   3600
tactactgga ccctcctcga gcccggcgac accatcatct tcgaggccaa cggcaacctg   3660 atcgcccct ggtacgcctt cgccctcagc cgcggcttcg gcagcggcat catcaccagc    3720
aacgccccca tggacgagtg cgacgccaag tgccagaccc ccagggcgc catcaacagc    3780 agcctcccgt tccagaacgt ccaccccgtc accatcggcg agtgcccaa gtacgtccgc    3840 agcgccaagc tccgcatggt caccggcctc cgcaacatcc ccagcatcca gagccgcggc   3900
ctcttcggcg ccatcgccgg cttcatcgag ggcggctgga ccggcatggt cgacggctgg   3960
tacggctacc accaccagaa cgagcagggc agcggctacg ccgccgacca gaagtcgacc   4020
cagaacgcca tcaacggcat caccaacaag gtcaacagcg tcatcgagaa gatgaacacc    4080
cagttcaccg ccgtcggcaa ggagttcaac aagctcgagc gccgcatgga gaacctcaac   4140
aagaaggtcg acgacggctt cctcgacatc tggacctaca acgccgagct gctcgtcctc   4200
ctcgagaacg agcgcaccct cgacttccac gacagcaacg tcaagaacct gtacgagaag   4260
gtcaagagcc agctcaagaa caacgccaag gagatcggca acggctgctt cgagttctac   4320
cacaagtgca caacgagtg catggagagc gtcaagaacg gcacctacga ctaccccaag    4380
tacagcgagg agagcaagct caaccgcgag aagatcgacg gcgtcaagct cgagagcatg   4440
ggcgtctacc agatcctcgc catctacagc accgtcgcca gcagcctcgt cctcctggtc   4500
agcctcggcg ccatctcgtt ctggatgtgc agcaacggca gcctccagtg ccgcatctgc   4560
atctgagaat tcggatccta agtaagtaaa cgaacctctc tgaaggaggt tctgagacac   4620
```

```
gcgcgattct tctgtatata gttttatttt tcactctgga gtgcttcgct ccaccagtac    4680 ataaacctt  tttttcacgt aacaaaatgg cttcttttca gaccatgtga accatcttga    4740
tgccttgacc tcttcagttc tcactttaac gtanttcgcg ttagtctgta tgtcccagtt    4800
gcatgtagtt gagataaata cccctggaag tgggtctggg cctttgtggg acggagccct    4860
ctttctgtgg tctggagagc ccgctctcta ccgcctacct tcttaccaca gtacactact    4920
cacacattgc tgaactgacc catcataccg tactttatcc tgttaattcg tggtgctgtc    4980
gactattcta tttgctcaaa tggagagcac attcatcggc gcagggatac acggtttatg    5040
gaccccaaga gtgtaaggac tattattagt aatattatat gcctctaggc gccttaactt    5100
caacaggcga gcactactaa tcaacttttg gtagacccaa ttacaaacga ccatacgtgc    5160
cggaaatttt gggattccgt ccgctctccc caaccaagct agaagaggca acgaacagcc    5220
aatcccggtg ctaattaaat tatatggttc atttttttta aaaaatttt tcttcccat     5280 tttcctctcg ctttttcttt tcgcatcgta gttgatcaaa gtccaagtca agcgagctat    5340
ttgtgctata gctcggtggc tataatcagt acagcttaga gaggctgtaa aggtatgata    5400
ccacagcagt attcgcgcta taagcggcac tcctagacta attgttacgg tctacagaag    5460
taggtaataa aagcgttaat tgttctaaat actagaggca cttagagaag ctatctaaat    5520
atatattgac cctagcttat tatccctatt agtaagttag ttagctctaa cctatagata    5580
gatgcatgc                                                            5589
```

<210> SEQ ID NO 17
<211> LENGTH: 5589
<212> TYPE: DNA
<213> ORGANISM: Artificial Sequence
<220> FEATURE:
<223> OTHER INFORMATION: Vector
<220> FEATURE:
<221> NAME/KEY: misc_feature
<222> LOCATION: (4774)..(4774)
<223> OTHER INFORMATION: n is a, c, g, or t

<400> SEQUENCE: 17

```
ggccgctcta gaactagtac ggcgtgcaag tagtgtcttt ctttgcactc ccgccgtccc     60
agaagacgcc gcaacaagct gagcttgctg gaagccgaac aaaggcgtta cagagcacaa    120
acatagtggc agtgtaggaa ctctaactgg gaccaaaact acgggcccgg cagaaacgtt    180
ccccgccccg aagcgaaggc gaacgtcgaa aagcaagacc gggaccgctc gtcccaggat    240
tagccacgaa gttccagacc aagtatagga gtaaacgctc gctcgtcaaa caattgtca    300 ccaatcagca ccacatcggc acataacaac cggttgcgga actcgcatgt gaacaacaag    360
cggctccggg ggagtgatcg gctcgggcgg atgacccgga ctcttccgcg cagcaactcg    420
gcgtgttgtt gacggcagta ctccgtagtt gccatgacaa cagtcaatgg cgtgcttcac    480
aaggtggaga gccgagaaag cacctcggca tgtacgagta tgtagatagt gtatcaagca    540
ggaagatggg ggttacttta tctcaatcag atgcctgtaa gcgagagccg agagcctgcc    600
ctgttgttga cacaattctg gcctgatacg agtgacaagc gctgggacgg cggctggggt    660
cttttgctcg cggcttcagc tcaattccaa tcctgggccg gtgccgaacg gcccaatcgc    720
gagcgcccac gaaatcggag gtcgaggaaa aaggctgggc gagacgcgg cgacaagctg    780 tggcaaaatg gccaattgag gttctgggtc ggctggtgat caaccatgca tttcccagcc    840
cgcagattct cttctctctct cgtgcagcag cggcaccagc agcagcagca gccagggggtt    900
```

```
tgaccaacct ctccgcccag ccaccgatag taaagatgct gcctgcgtat tctgggctgc    960
aggagttcca agatctttcg gtctggccac cagctgtcac gtcaccctcc acctttggac   1020
gacgttgctg gaaaattcga agccttcact aagataacta tgccgtagca cttgcagccc   1080
cggaagctgc aagttgattc ttggagggct ctctccacca ccaatacggg agatctggcc   1140
ccgcacttga ggaggctgga gtctcggatc gcccacttcg cgtcgccctg ggccctgggc   1200
cctggggtga tgggcccgtt gccgtggtgg atggcaggag cttttcagct ctcaatgggc   1260
gaatgctact ccgtaggtcg gagtggctgg aagcggcgga acggacaggg ggaggttggg   1320
gaaaatgctc cgcaggaaga gcagggagtg gggagctgcg gtcggccctg tggagcccgt   1380
gcagggccag ctaatccaat cgggccacaa ataaacaaga gagggcccca catcatgtaa   1440
acagaggctc agaagctcct gccacactgg gagggtttcg aagtctgacg actgccaatg   1500
gaccccagcc atcgcgagca cacagcagtt cgcacgctcc cattgggttc ctcatcacgc   1560
agtcgctctc cccgccaacc agcgccaggt ccgggaacag cggcgcaaat gcgtatttga   1620
gggcgcctcg ctcgagcaac ctgtgcctga ccttctcctc ctccttctgc accttgcatc   1680
tcgtcgcgtc cactcgcagg caaccacaca tcctcctcct ctcccaaaac cccccgctt    1740
tttctttccc ttgttggaat tcgattgaaa aagaagacgg gtccgtctag agaccgcctt   1800
ctcacctttc tctcgacttc tttctaggaa aagaagcaag agtcattctt cttgtccacc   1860
ttctggttca cggaaggtcg aggagaagat tgcctctgcc cccaaagtcg ccaacctgga   1920
ctttgaagca cgtgttccgg tccctttcag tgtcttcccg tcctcgtaca gggagtccga   1980
gaccgccacc caaacccact cccacgaaga ggttgagatc aagctccccc agctcgccgg   2040
acgggaaggt caacactctt cattccaagc ccaagcacat cttcctccca gcggagaggg   2100
tcgcttcaga gaagaagagg tccgcatcac tcgtcaagag gaacatcacc gccgtcccgg   2160
catccgtgaa gagttcgttc accgcgagga gcgtcaccgg taagtttagt ttttgttttg   2220
attcaccacc cattgtcttc cccgcctttt tcttttttctt cccttgctct cttgcccctg   2280
tctagtgtag ggcattgcca aggccatctt cacacacaca cacccccccc cccccccacc   2340
ctcagctggg ggggggggtg gcctgggttg accaagggac ggtgaagact actactactt   2400
gagccactca aacccatgca tgacacaggg ttttccttt tctttctct tttcctttaa    2460
ctaaccaacc actccaacat tagccctcag tcaacctact ccgagtctcg catcgagttc   2520
gatactgagc accgcactca caactccgtc attgacgttg ctgagagcga gtatcgtgcc   2580
cgtgtccagc ccaactaccg caaggaagct tccgtagtcg gtaccaccgt cgacggatcc   2640
cgcttcagcc acagccgcaa ggccagcagc accacctcca cccacaccga cgagtacacc   2700
gtcgatcccc ctagccaccg ccccgtctac aagaaggagt cggttgaagt cgccggtacc   2760
actgttgacc cccctgctcc tcgttcgacc taccacgagc aggtgaacat tgttgaagag   2820
accgttgacg ctcaccgtta cgctcctcaa cccaacaaca caacaccat gtacgccaag    2880
ttcgcgaccc tcgccgccct tgtggctggc gccgctgctg acaccatctg catcggctac   2940
cacgccaaca cagcaccga caccgtcgac acggtcctcg agaagaacgt caccgtcacc   3000
cacagcgtca acctgctcga ggacagccac aacggcaagc tctgcctcct caagggcatc   3060
gccccctcc agctcggcaa ctgcagcgtc gccggctgga tcctcggcaa ccccgagtgc   3120
gagctgctca tcagcaagga gagctggtcg tacatcgtcg agaccccaa ccccgagaac    3180
ggcacgtgct accccggcta cttcgccgac tacgaggagc tgcgcgagca gctcagcagc   3240
gtcagctcgt tcgagcgctt cgagatcttc cccaaggaga gcagctggcc caaccacacc   3300
```

-continued

```
gtcaccggcg tcagcgccag ctgctcgcac aacggcaaga gcagcttcta ccgcaacctc    3360
ctctggctca ccggcaagaa cggcctctac ccgaacctca gcaagagcta cgtcaacaac    3420
aaggagaagg aggtcctcgt cctctggggc gtccaccacc cccccaacat cggcaaccag    3480
cgcgccctct accacaccga gaacgcctac gtcagcgtcg tcagcagcca ctacagccgc    3540
cgcttcaccc ccgagatcgc caagcgcccc aaggtccgcg accaggaggg ccgcatcaac    3600
tactactgga ccctcctcga gcccggcgac accatcatct tcgaggccaa cggcaacctg    3660 atcgcccccct ggtacgcctt cgccctcagc cgcggcttcg gcagcggcat catcaccagc    3720
aacgccccca tggacgagtg cgacgccaag tgccagaccc ccagggcgc catcaacagc    3780 agcctcccgt tccagaacgt ccaccccgtc accatcggcg agtgccccaa gtacgtccgc    3840
agcgccaagc tccgcatggt caccggcctc cgcaacatcc ccagcatcca gagccgcggc    3900
ctcttcggcg ccatcgccgg cttcatcgag ggcggctgga ccggcatggt cgacggctgg    3960
tacggctacc accaccagaa cgagcagggc agcggctacg ccgccgacca gaagtcgacc    4020
cagaacgcca tcaacggcat caccaacaag gtcaacagcg tcatcgagaa gatgaacacc    4080
cagttcaccg ccgtcggcaa ggagttcaac aagctcgagc gccgcatgga gaacctcaac    4140
aagaaggtcg acgacggctt cctcgacatc tggacctaca acgccgagct gctcgtcctc    4200
ctcgagaacg agcgcaccct cgacttccac gacagcaacg tcaagaacct gtacgagaag    4260
gtcaagagcc agctcaagaa caacgccaag gagatcggca cggctgctt cgagttctac    4320 cacaagtgca acaacgagtg catggagagc gtcaagaacg gcacctacga ctaccccaag    4380
tacagcgagg agagcaagct caaccgcgag aagatcgacg gcgtcaagct cgagagcatg    4440
ggcgtctacc agatcctcgc catctacagc ccgtcgcca gcagcctcgt cctcctggtc    4500
agcctcggcg ccatctcgtt ctggatgtgc agcaacggca gcctccagtg ccgcatctgc    4560
atctgagaat tcggatccta agtaagtaaa cgaacctctc tgaaggaggt tctgagacac    4620
gcgcgattct tctgtatata gttttatttt tcactctgga gtgcttcgct ccaccagtac    4680 ataaacctt ttttttcacgt aacaaaatgg cttcttttca gaccatgtga accatcttga    4740
tgccttgacc tcttcagttc tcactttaac gtanttcgcg ttagtctgta tgtcccagtt    4800
gcatgtagtt gagataaata cccctggaag tgggtctggg cctttgtggg acggagccct    4860
ctttctgtgg tctggagagc ccgctctcta ccgcctacct tcttaccaca gtacactact    4920
cacacattgc tgaactgacc catcataccg tactttatcc tgttaattcg tggtgctgtc    4980
gactattcta tttgctcaaa tggagagcac attcatcggc gcagggatac acggtttatg    5040 gacccccaaga gtgtaaggac tattattagt aatattatat gcctctaggc gccttaactt    5100
caacaggcga gcactactaa tcaacttttg gtagacccaa ttacaaacga ccatcgtgc    5160 cggaaattt gggattccgt ccgctctccc caaccaagct agaagaggca acgaacagcc    5220
aatcccggtg ctaattaaat tatatggttc attttttta aaaaatttt ttcttcccat    5280 tttcctctcg cttttctttt tcgcatcgta gttgatcaaa gtccaagtca agcgagctat    5340
ttgtgctata gctcggtggc tataatcagt acagcttaga gaggctgtaa aggtatgata    5400
ccacagcagt attcgcgcta taagcggcac tcctagacta attgttacgg tctacagaag    5460
taggtaataa aagcgttaat tgttctaaat actagaggca cttagagaag ctatctaaat    5520
atatattgac cctagcttat tatccctatt agtaagttag ttagctctaa cctatagata    5580
gatgcatgc                                                            5589
```

<210> SEQ ID NO 18
<211> LENGTH: 545
<212> TYPE: PRT
<213> ORGANISM: Artificial Sequence
<220> FEATURE:
<223> OTHER INFORMATION: Polypeptide

<400> SEQUENCE: 18

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Thr Pro Asn Pro Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Lys Ser Ser Phe Tyr
    130                 135                 140

Arg Asn Leu Leu Trp Leu Thr Gly Lys Asn Gly Leu Tyr Pro Asn Leu
145                 150                 155                 160

Ser Lys Ser Tyr Val Asn Asn Lys Glu Lys Glu Val Leu Val Leu Trp
                165                 170                 175

Gly Val His His Pro Pro Asn Ile Gly Asn Gln Arg Ala Leu Tyr His
            180                 185                 190

Thr Glu Asn Ala Tyr Val Ser Val Val Ser Ser His Tyr Ser Arg Arg
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Trp Tyr Ala Phe Ala Leu
                245                 250                 255

Ser Arg Gly Phe Gly Ser Gly Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365
```

```
Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asn Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Val Lys Leu Glu Ser Met Gly Val Tyr Gln Gly
            500                 505                 510

Gly Gly Gly Gly Gly Gly Gly Tyr Ile Pro Glu Ala Pro Arg Asp Gly
        515                 520                 525

Gln Ala Tyr Val Arg Lys Asp Gly Glu Trp Val Leu Leu Ser Thr Phe
    530                 535                 540

Leu
545

<210> SEQ ID NO 19
<211> LENGTH: 1690
<212> TYPE: DNA
<213> ORGANISM: Artificial Sequence
<220> FEATURE:
<223> OTHER INFORMATION: Polynucleotide

<400> SEQUENCE: 19
atgtacgcca agttcgcgac cctcgccgcc cttgtggctg gcgccgctgc tgacaccatc      60
tgcatcggct accacgccaa caacagcacc gacaccgtcg acaccgtcct cgagaagaac     120
gtcaccgtca cccacagcgt caacctgctc gaggacagcc acaacggcaa gctctgcctc     180
ctcaagggca tcgccccccct ccagctcggc aactgcagcg tcgccggctg gatcctcggc     240
aaccccgagt gcgagctgct catcagcaag gagagctggt cgtacatcgt cgagaccccc     300
aaccccgaga cggcacgtg ctaccccggc tacttcgccg actacgagga gctgcgcgag     360
cagctcagca gcgtcagctc gttcgagcgc ttcgagatct cccccaagga gagcagctgg     420
cccaaccaca ccgtcaccgg cgtcagcgcc agctgctcgc acaacggcaa gagcagcttc     480
taccgcaacc tcctctggct caccggcaag aacggcctct acccgaacct cagcaagagc     540
tacgtcaaca caaggagaa ggaggtcctc gtcctctggg cgtccacca ccccccccaac     600 atcggcaacc agcgcgccct ctaccacacc gagaacgcct acgtcagcgt cgtcagcagc     660
cactacagcc gccgcttcac ccccgagatc gccaagcgcc caaggtccg cgaccaggag     720 ggccgcatca actactactg gacccctcctc gagcccggcg acaccatcat cttcgaggcc     780
aacggcaacc tgatcgcccc ctggtacgcc ttcgccctca gccgcggctt cggcagcggc     840
atcatcacca gcaacgcccc catggacgag tgcgacgcca gtgccagac ccccagggc     900 gccatcaaca gcagcctccc gttccagaac gtccaccccg tcaccatcgg cgagtgcccc     960
aagtacgtcc gcagcgccaa gctccgcatg gtcaccggcc tccgcaacat ccccagcatc    1020
```

```
cagagccgcg gcctcttcgg cgccatcgcc ggcttcatcg agggcggctg gaccggcatg    1080
gtcgacggct ggtacggcta ccaccaccag aacgagcagg gcagcggcta cgccgccgac    1140
cagaagtcga cccagaacgc catcaacggc atcaccaaca aggtcaacag cgtcatcgag    1200
aagatgaaca cccagttcac cgccgtcggc aaggagttca acaagctcga cgccgcatg     1260 gagaacctca caagaaggt cgacgacggc ttcctcgaca tctggaccta caacgccgag    1320
ctgctcgtcc tcctcgagaa cgagcgcacc ctcgacttcc acgacagcaa cgtcaagaac    1380
ctgtacgaga aggtcaagag ccagctcaag aacaacgcca aggagatcgg caacggctgc    1440
ttcgagttct accacaagtg caacaacgag tgcatggaga gcgtcaagaa cggcaccctac   1500 gactacccca gtacagcga ggagagcaag ctcaaccgcg agaagatcga cggcgtcaag    1560
ctcgagagca tgggcgtcta ccagggcggc ggcggcggcg gcggcggcta catccccgag    1620
gccccccgcg acggccaggc ctacgtccgc aaggacggcg agtgggtcct cctcagcacc    1680
ttcctgtgag                                                          1690

<210> SEQ ID NO 20
<211> LENGTH: 571
<212> TYPE: PRT
<213> ORGANISM: Artificial Sequence
<220> FEATURE:
<223> OTHER INFORMATION: Polypeptide

<400> SEQUENCE: 20

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Gly Ser Cys Pro
    130                 135                 140

Asn Ala Thr Ser Lys Ser Gly Phe Phe Ala Thr Met Ala Trp Ala Val
145                 150                 155                 160

Pro Lys Asp Asn Lys Asn Ala Thr Asn Pro Leu Thr Val Glu Val
                165                 170                 175

Pro Tyr Ile Cys Thr Glu Gly Glu Asp Gln Ile Thr Val Trp Gly Phe
            180                 185                 190

His Ser Asp Asp Lys Thr Gln Met Lys Asn Leu Tyr Gly Asp Ser Asn
        195                 200                 205

Pro Gln Lys Phe Thr Ser Ser Ala Asn Gly Val Thr Thr His Tyr Val
    210                 215                 220

Ser Gln Ile Gly Ser Phe Pro Asp Gln Thr Glu Asp Gly Gly Leu Pro
225                 230                 235                 240
```

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg Gly Phe Phe Gly Ala Ile
            340                 345                 350

Ala Gly Phe Leu Glu Gly Gly Trp Glu Gly Met Ile Ala Gly Trp His
        355                 360                 365

Gly Tyr Thr Ser His Gly Ala His Gly Val Ala Val Ala Ala Asp Leu
370                 375                 380

Lys Ser Thr Gln Glu Ala Ile Asn Lys Ile Thr Lys Asn Leu Asn Ser
385                 390                 395                 400

Leu Ser Glu Leu Glu Val Lys Asn Leu Gln Arg Leu Ser Gly Ala Met
                405                 410                 415

Asp Glu Leu His Asn Glu Ile Leu Glu Leu Asp Glu Lys Val Asp Asp
            420                 425                 430

Leu Arg Ala Asp Thr Ile Ser Ser Gln Ile Glu Leu Ala Val Leu Leu
        435                 440                 445

Ser Asn Glu Gly Ile Ile Asn Ser Glu Asp Glu His Leu Leu Ala Leu
450                 455                 460

Glu Arg Lys Leu Lys Lys Met Leu Gly Pro Ser Ala Val Glu Ile Gly
465                 470                 475                 480

Asn Gly Cys Phe Glu Thr Lys His Lys Cys Asn Gln Thr Cys Leu Asp
                485                 490                 495

Arg Ile Ala Ala Gly Thr Phe Asn Ala Gly Glu Phe Ser Leu Pro Thr
            500                 505                 510

Phe Asp Ser Leu Asn Ile Thr Ala Ala Ser Leu Asn Asp Asp Gly Leu
        515                 520                 525

Asp Asn His Thr Ile Leu Leu Tyr Tyr Gly Gly Gly Gly Gly Gly Gly
530                 535                 540

Gly Tyr Ile Pro Glu Ala Pro Arg Asp Gly Gln Ala Tyr Val Arg Lys
545                 550                 555                 560

Asp Gly Glu Trp Val Leu Leu Ser Thr Phe Leu
                565                 570

<210> SEQ ID NO 21
<211> LENGTH: 1768
<212> TYPE: DNA
<213> ORGANISM: Artificial Sequence
<220> FEATURE:
<223> OTHER INFORMATION: Polynucleotide

<400> SEQUENCE: 21
atgtacgcca agttcgcgac cctcgccgcc cttgtggctg gcgccgctgc tgaccgcatc    60
tgcaccggca tcaccagcag caacagcccc cacgtcgtca agaccgccac ccagggcgag   120
gtcaacgtca cgggcgtcat ccccctcacc accaccccca ccaagagcta cttcgccaac   180

-continued

```
ctcaagggca cccgcacccg cggcaagctc tgccccgact gcctcaactg caccgacctc    240
gacgtcgccc tcggccgccc catgtgcgtc ggcaccaccc ccagcgccaa ggccagcatc    300
ctccacgagg tcaagcccgt caccagcggc tgcttcccca tcatgcacga ccgcaccaag    360
atccgccagc tccccaacct cctccgcggc tacgagaaca tccgcctcag cacccagaac    420
gtcatcgacg ccgagaaggc cccggcggc ccctaccgcc tcggcaccag cggctcgtgc    480
cccaacgcca ccagcaagag cggcttcttc gccaccatgg cctgggccgt ccccaaggac    540
aacaacaaga acgccaccaa ccccctgacc gtcgaggtcc cctacatctg caccgagggc    600
gaggaccaga tcaccgtctg gggcttccac agcgacgaca gacccagat gaagaacctc    660
tacggcgaca gcaaccccca gaagttcacc agcagcgcca acggcgtcac cacccactac    720
gtcagccaga tcggcagctt ccccgaccag accgaggacg cgggcctccc ccagtcgggc    780
cgcatcgtcg tcgactacat gatgcagaag cccggcaaga ccggcaccat cgtctaccag    840
cgcggcgtcc tcctgcccca gaaggtctgg tgcgcctcgg ccgcagcaa ggtcatcaag    900
ggcagcctcc cgctcatcgg cgaggccgac tgcctccacg agaagtacgg cggcctcaac    960
aagagcaagc cctactacac gggcgagcac gccaaggcca tcggcaactg ccccatctgg   1020
gtcaagaccc ccctcaagct cgccaacggc accaagtacc gccccccgc caagctcctc   1080
aaggagcggg gcttcttcgg cgccatcgcc ggcttcctcg agggcggctg ggagggcatg   1140
atcgccggct ggcacggcta caccagccac ggcgcccacg gcgtcgccgt cgccgccgac   1200
ctcaagtcga cccaggaggc catcaacaag atcaccaaga acctcaacag cctcagcgag   1260
ctggaggtca agaacctcca gcgcctctcg ggcgccatgg acgagctgca caacgagatc   1320
ctcgagctgg acgagaaggt cgacgacctc cgcgccgaca ccatcagcag ccagatcgag   1380
ctggccgtcc tcctcagcaa cgagggcatc atcaacagcg aggacgagca cctcctggcc   1440
ctcgagcgca agctcaagaa gatgctcggc ccagcgccg tcgagatcgg caacggctgc   1500
ttcgagacca agcacaagtg caaccagacc tgcctcgacc ggatcgccgc cggcaccttc   1560
aacgccggcg agttcagcct ccccaccttc gacagcctca acatcaccgc cgccagcctc   1620
aacgacgacg gcctcgacaa ccacaccatc ctgctctact acgcggcgg cggcggcggc   1680
ggcggctaca tccccgaggc ccccgcgac ggccaggcct acgtccgcaa ggacggcgag   1740
tgggtcctcc tcagcacctt cctgtgag                                      1768
```

<210> SEQ ID NO 22
<211> LENGTH: 449
<212> TYPE: PRT
<213> ORGANISM: Artificial Sequence
<220> FEATURE:
<223> OTHER INFORMATION: Polypeptide

<400> SEQUENCE: 22

```
Met Tyr Ala Lys Phe Ala Thr Leu Ala Ala Leu Val Ala Gly Ala Ala
1               5                   10                  15

Ala Ser Ser Ser Asp Tyr Ser Asp Leu Gln Arg Val Lys Gln Glu Leu
            20                  25                  30

Leu Glu Glu Val Lys Lys Glu Leu Gln Lys Val Lys Glu Glu Ile Ile
        35                  40                  45

Glu Ala Phe Val Gln Glu Leu Arg Lys Arg Gly Gly Ser Val Thr Leu
    50                  55                  60

Ala Gly Asn Ser Ser Leu Cys Ser Ile Ser Gly Trp Ala Ile Tyr Thr
65                  70                  75                  80
```

Lys Asp Asn Ser Ile Arg Ile Gly Ser Lys Gly Asp Val Phe Val Ile
                85                  90                  95

Arg Glu Pro Phe Ile Ser Cys Ser His Leu Glu Cys Arg Thr Phe Phe
            100                 105                 110

Leu Thr Gln Gly Ala Leu Leu Asn Asp Lys His Ser Asn Gly Thr Val
        115                 120                 125

Lys Asp Arg Ser Pro Tyr Arg Ala Leu Met Ser Cys Pro Leu Gly Glu
    130                 135                 140

Ala Pro Ser Pro Tyr Asn Ser Lys Phe Glu Ser Val Ala Trp Ser Ala
145                 150                 155                 160

Ser Ala Cys His Asp Gly Met Gly Trp Leu Thr Ile Gly Ile Ser Gly
                165                 170                 175

Pro Asp Asn Gly Ala Val Ala Val Leu Lys Tyr Asn Gly Ile Ile Thr
            180                 185                 190

Glu Thr Ile Lys Ser Trp Lys Lys Arg Ile Leu Arg Thr Gln Glu Ser
        195                 200                 205

Glu Cys Val Cys Val Asn Gly Ser Cys Phe Thr Ile Met Thr Asp Gly
    210                 215                 220

Pro Ser Asn Gly Ala Ala Ser Tyr Lys Ile Phe Lys Ile Glu Lys Gly
225                 230                 235                 240

Lys Val Thr Lys Ser Ile Glu Leu Asn Ala Pro Asn Phe His Tyr Glu
                245                 250                 255

Glu Cys Ser Cys Tyr Pro Asp Thr Gly Thr Val Met Cys Val Cys Arg
            260                 265                 270

Asp Asn Trp His Gly Ser Asn Arg Pro Trp Val Ser Phe Asn Gln Asn
        275                 280                 285

Leu Asp Tyr Gln Ile Gly Tyr Ile Cys Ser Gly Val Phe Gly Asp Asn
    290                 295                 300

Pro Arg Pro Lys Asp Gly Glu Gly Ser Cys Asn Pro Val Thr Val Asp
305                 310                 315                 320

Gly Ala Asp Gly Val Lys Gly Phe Ser Tyr Lys Tyr Gly Asn Gly Val
                325                 330                 335

Trp Ile Gly Arg Thr Lys Ser Asn Arg Leu Arg Lys Gly Phe Glu Met
            340                 345                 350

Ile Trp Asp Pro Asn Gly Trp Thr Asp Thr Asp Ser Asp Phe Ser Val
        355                 360                 365

Lys Gln Asp Val Val Ala Ile Thr Asp Trp Ser Gly Tyr Ser Gly Ser
    370                 375                 380

Phe Val Gln His Pro Glu Leu Thr Gly Leu Asp Cys Ile Arg Pro Cys
385                 390                 395                 400

Phe Trp Val Glu Leu Val Arg Gly Leu Pro Arg Glu Asn Thr Thr Ile
                405                 410                 415

Trp Thr Ser Gly Ser Ser Ile Ser Phe Cys Gly Val Asn Ser Asp Thr
            420                 425                 430

Ala Asn Trp Ser Trp Pro Asp Gly Ala Glu Leu Pro Phe Thr Ile Asp
        435                 440                 445

Lys

<210> SEQ ID NO 23
<211> LENGTH: 628
<212> TYPE: PRT
<213> ORGANISM: Myceliophthora thermophila

<400> SEQUENCE: 23

```
Met His Ala Leu Ser Ser Leu Ala Val Leu Gly Ala Trp Ala Val Gln
1               5                   10                  15

Thr Val Leu Gly Arg Pro Ala Thr Leu Ser Lys Arg Ala Thr Asp Ser
            20                  25                  30

Phe Ile Glu Thr Glu Thr Pro Ile Ala Trp Glu Lys Leu Arg Cys Asn
        35                  40                  45

Ile Gly Ala Asn Gly Cys Ala Ala Ser Gly Ala Ala Ala Gly Val Val
    50                  55                  60

Ile Ala Ser Pro Ser Lys Ser Asp Pro Asp Tyr Phe Tyr Thr Trp Thr
65                  70                  75                  80

Arg Asp Ala Gly Leu Val Leu Thr Gly Ile Val Asp Ala Leu Ser Gln
                85                  90                  95

Asn Tyr Ser Ala Ala Leu Gln Thr Asn Ile Gln Asp Tyr Ile Ile Ala
            100                 105                 110

Gln Ala Lys Leu Gln Gly Val Ser Asn Pro Ser Gly Ser Leu Ser Asp
        115                 120                 125

Gly Thr Gly Leu Gly Glu Pro Lys Phe Asn Val Asp Leu Thr Gln Phe
    130                 135                 140

Thr Gly Asp Trp Gly Arg Pro Gln Arg Asp Gly Pro Pro Leu Arg Ala
145                 150                 155                 160

Ile Ala Leu Ile Arg Tyr Ala Lys Trp Leu Ala Ser Asn Gly Tyr Lys
                165                 170                 175

Asp Thr Ala Asn Ser Val Val Trp Pro Val Ile Lys Asn Asp Leu Ala
            180                 185                 190

Tyr Ala Ala Gln Tyr Trp Asn Glu Thr Gly Phe Asp Leu Trp Glu Glu
        195                 200                 205

Val Pro Gly Ser Ser Phe Phe Thr Ile Ala Ser Thr His Arg Ala Leu
    210                 215                 220

Val Glu Gly Ala Ala Leu Ala Ala Gln Leu Gly Thr Glu Cys Ser Ala
225                 230                 235                 240

Cys Ile Thr Val Ala Pro Gln Val Leu Cys Phe Gln Gln Ser Phe Trp
                245                 250                 255

Asn Pro Ser Gly Gly Tyr Val Val Ser Asn Ile Asn Gly Gly Asn Asn
            260                 265                 270

Arg Ser Gly Lys Asp Leu Asn Ser Val Leu Ala Ser Ile His Thr Phe
        275                 280                 285

Asp Pro Ala Val Gly Cys Asp Ser Val Thr Phe Gln Pro Cys Ser Asp
    290                 295                 300

Lys Ala Leu Ser Asn His Lys Ala Tyr Val Asp Ser Phe Arg Ser Val
305                 310                 315                 320

Tyr Ala Ile Asn Ser Gly Ile Ala Gln Gly Lys Ala Val Ala Val Gly
                325                 330                 335

Arg Tyr Ser Glu Asp Val Tyr Tyr Asn Gly Asn Pro Trp Tyr Leu Ala
            340                 345                 350

Asn Phe Ala Ala Ala Glu Gln Leu Tyr Asp Ala Val Phe Val Trp Lys
        355                 360                 365

Lys Gln Gln Ser Ile Glu Val Thr Gln Leu Ser Leu Pro Phe Phe Lys
    370                 375                 380

Asp Leu Leu Pro Gly Ile Ser Thr Gly Thr Tyr Thr Pro Ser Ser Ser
385                 390                 395                 400

Thr Tyr Gln Gln Ile Leu Asp Ala Val Ser Ala Tyr Ala Asp Gly Phe
                405                 410                 415
```

```
Ile Asp Val Ala Ala Lys Tyr Thr Pro Ser Asp Gly Ser Leu Ala Glu
            420                 425                 430

Gln Tyr Thr Arg Asp Ser Gly Gln Pro Ile Ser Ala Lys Asp Leu Thr
            435                 440                 445

Trp Ser Tyr Ala Ala Phe Leu Ser Ala Ala Asp Arg Arg Ala Gly Ile
450                 455                 460

Val Pro Ala Gly Trp Ser Ala Glu His Gly Lys Thr Leu Pro Gly Ser
465                 470                 475                 480

Cys Ser Ala Val Gln Val Ala Gly Thr Tyr Thr Gln Ala Thr Ala Thr
            485                 490                 495

Ser Phe Pro Pro Gly Gln Thr Pro Asn Pro Thr Ser Asp Thr Pro Ala
            500                 505                 510

Pro Phe Pro Thr Ala Cys Ala Asp Ser Thr Gln Val Phe Val Thr Phe
            515                 520                 525

Arg Ala Glu Val Thr Thr Gln Trp Gly Gln Ser Val Lys Val Val Gly
            530                 535                 540

Ser Ser Ser Glu Leu Gly Asn Trp Asp Val Ser Lys Ala Pro Arg Leu
545                 550                 555                 560

Ser Ala Ser Ala Tyr Thr Ala Ser Asp Pro Leu Trp Ala Ile Thr Val
            565                 570                 575

Pro Met Lys Ala Gly Gln Ser Val Gln Tyr Lys Phe Val Lys Val Asn
            580                 585                 590

Gly Asp Gly Ser Ile Gln Trp Glu Ser Asp Pro Asn Arg Gln Phe Thr
            595                 600                 605

Val Ser Ser Ser Thr Ala Ser Gly Cys Ala Trp Gln Thr Ile Glu
            610                 615                 620

Ala Thr Trp Arg
625

<210> SEQ ID NO 24
<211> LENGTH: 640
<212> TYPE: PRT
<213> ORGANISM: Aspergillus niger

<400> SEQUENCE: 24

Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
            35                  40                  45

Asp Gly Ala Trp Val Ser Gly Ala Asp Ser Gly Ile Val Val Ala Ser
50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
            85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
            115                 120                 125

Gly Glu Pro Lys Phe Asn Val Asp Glu Thr Ala Tyr Thr Gly Ser Trp
130                 135                 140

Gly Arg Pro Gln Arg Asp Gly Pro Ala Leu Arg Ala Thr Ala Met Ile
145                 150                 155                 160
```

```
Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Ser Thr
        515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575
```

```
Ala Asp Lys Tyr Thr Ser Ser Asp Pro Leu Trp Tyr Val Thr Val Thr
            580                 585                 590

Leu Pro Ala Gly Glu Ser Phe Glu Tyr Lys Phe Ile Arg Ile Glu Ser
        595                 600                 605

Asp Asp Ser Val Glu Trp Glu Ser Asp Pro Asn Arg Glu Tyr Thr Val
    610                 615                 620

Pro Gln Ala Cys Gly Thr Ser Thr Ala Thr Val Thr Asp Thr Trp Arg
625                 630                 635                 640

<210> SEQ ID NO 25
<211> LENGTH: 1920
<212> TYPE: DNA
<213> ORGANISM: Artificial Sequence
<220> FEATURE:
<223> OTHER INFORMATION: Polynucleotide

<400> SEQUENCE: 25
```

| | | | | |
|---|---|---|---|---|
| atgtcgttcc | gatctctact | cgccctgagc | ggcctcgtct | gcacagggtt ggcaaatgtg | 60 |
| atttccaagc | gcgcgacctt | ggattcatgg | ttgagcaacg | aagcgaccgt ggctcgtact | 120 |
| gccatcctga | ataacatcgg | gcggacggt | gcttgggtgt | cgggcgcgga ctctggcatt | 180 |
| gtcgttgcta | gtcccagcac | ggataacccg | gactacttct | acacctggac tcgcgactct | 240 |
| ggtctcgtcc | tcaagaccct | cgtcgatctc | ttccgaaatg | gagataccag tctcctctcc | 300 |
| accattgaga | actacatctc | cgcccaggca | attgtccagg | gtatcagtaa ccctctggt | 360 |
| gatctgtcca | gcggcgctgg | tctcggtgaa | cccaagttca | atgtcgatga gactgcctac | 420 |
| actggttctt | ggggacggcc | gcagcgagat | ggtccggctc | tgagagcaac tgctatgatc | 480 |
| ggcttcgggc | agtggctgct | tgacaatggc | tacaccagca | ccgcaacgga cattgtttgg | 540 |
| cccctcgtta | ggaacgacct | gtcgtatgtg | gctcaatact | ggaaccagac aggatatgat | 600 |
| ctctgggaag | aagtcaatgg | ctcgtctttc | tttacgattg | ctgtgcaaca ccgcgccctt | 660 |
| gtcgaaggta | gtgccttcgc | gacggccgtc | ggctcgtcct | gctcctggtg tgattctcag | 720 |
| gcacccgaaa | ttctctgcta | cctgcagtcc | ttctggaccg | gcagcttcat tctggccaac | 780 |
| ttcgatagca | gccgttccgg | caaggacgca | aacacccctcc | tgggaagcat ccacaccttt | 840 |
| gatcctgagg | ccgcatgcga | cgactccacc | ttccagccct | gctccccgcg cgcgctcgcc | 900 |
| aaccacaagg | aggttgtaga | ctcttttccgc | tcaatctata | ccctcaacga tggtctcagt | 960 |
| gacagcgagg | ctgttgcggt | gggtcggtac | cctgaggaca | cgtactacaa cggcaacccg | 1020 |
| tggttcctgt | gcaccttggc | tgccgcagag | cagttgtacg | atgctctata ccagtgggac | 1080 |
| aagcaggggt | cgttggaggt | cacagatgtg | tcgctggact | tcttcaaggc actgtacagc | 1140 |
| gatgctgcta | ctggcaccta | ctcttcgtcc | agttcgactt | atagtagcat tgtagatgcc | 1200 |
| gtgaagactt | tcgccgatgg | cttcgtctct | attgtggaaa | ctcacgccgc aagcaacggc | 1260 |
| tccatgtccg | agcaatacga | caagtctgat | ggcgagcagc | tttccgctcg cgacctgacc | 1320 |
| tggtcttatg | ctgctctgct | gaccgccaac | aaccgtcgta | actccgtcgt gcctgcttct | 1380 |
| tggggcgaga | cctctgccag | cagcgtgccc | ggcacctgtg | cggccacatc tgccattggt | 1440 |
| acctacagca | gtgtgactgt | cacctcgtgg | ccgagtatcg | tggctactgg cggcaccact | 1500 |
| acgacggcta | ccccactgg | atccggcagc | gtgacctcga | ccagcaagac caccgcgact | 1560 |
| gctagcaaga | ccagcaccag | tacgtcatca | acctcctgta | ccactcccac cgccgtggct | 1620 |
| gtgactttcg | atctgacagc | taccaccacc | tacggcgaga | catctacct ggtcggatcg | 1680 |
| atctctcagc | tgggtgactg | ggaaaccagc | gacggcatag | ctctgagtgc tgacaagtac | 1740 |

```
acttccagcg acccgctctg gtatgtcact gtgactctgc cggctggtga gtcgtttgag   1800
tacaagttta tccgcattga gagcgatgac tccgtggagt gggagagtga tcccaaccga   1860
gaatacaccg ttcctcaggc gtgcggaacg tcgaccgcga cggtgactga cacctggcgg   1920
```

<210> SEQ ID NO 26
<211> LENGTH: 389
<212> TYPE: PRT
<213> ORGANISM: Myceliophthora thermophila

<400> SEQUENCE: 26

```
Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Glu Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Val Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Asn Ile Gly Ala Gln Arg
    290                 295                 300

Val Val Gly Ala Thr Gln Trp Leu Arg Ala Asn Gly Lys Leu Gly Val
305                 310                 315                 320

Leu Gly Glu Phe Ala Gly Gly Ala Asn Ala Val Cys Gln Gln Ala Val
                325                 330                 335

Thr Gly Leu Leu Asp His Leu Gln Asp Asn Ser Asp Val Trp Leu Gly
```

Ala Leu Trp Trp Ala Ala Gly Pro Trp Trp Gly Asp Tyr Met Tyr Ser
        340                 345                 350

Phe Glu Pro Pro Ser Gly Thr Gly Tyr Val Asn Tyr Asn Ser Ile Leu
        355                 360                 365

Lys Lys Tyr Leu Pro
        370                 375                 380

385

<210> SEQ ID NO 27
<211> LENGTH: 1167
<212> TYPE: DNA
<213> ORGANISM: Artificial Sequence
<220> FEATURE:
<223> OTHER INFORMATION: Polynucleotide

<400> SEQUENCE: 27

```
atgaagtcct ccatcctcgc cagcgtcttc gccacgggcg ccgtggctca aagtggtccg      60
tggcagcaat gtggtggcat cggatggcaa ggatcgaccg actgtgtgtc gggttaccac     120
tgcgtctacc agaacgattg gtacagccag tgcgtgcctg cgcggcgtc gacaacgctc     180
cagacatcta ccacgtccag gcccaccgcc accagcaccg cccctccgtc gtccaccacc     240
tcgcctagca agggcaagct caagtggctc ggcagcaacg agtcgggcgc cgagttcggg     300
gagggcaact accccggcct ctggggcaag cacttcatct tcccgtcgac ttcggcgatt     360
cagacgctca tcaatgatgg atacaacatc ttccggatcg acttctcgat ggagcgtctg     420
gtgcccaacc agttgacgtc gtccttcgac gagggctacc tccgcaacct gaccgaggtg     480
gtcaacttcg tgacgaacgc gggcaagtac gccgtcctgg acccgcacaa ctacggccgg     540
tactacggca acgtcatcac ggacacgaac gcgttccgga ccttctggac caacctggcc     600
aagcagttcg cctccaactc gctcgtcatc ttcgacacca caacgagta caacacgatg     660
gaccagaccc tggtgctcaa cctcaaccag gccgccatcg acggcatccg ggccgccggc     720
gcgacctcgc agtacatctt cgtcgagggc aacgcgtgga gcggggcctg gagctggaac     780
acgaccaaca ccaacatggc cgccctgacg gacccgcaga acaagatcgt gtacgagatg     840
caccagtacc tcgactcgga cagctcgggc acccacgccg agtgcgtcag cagcaacatc     900
ggcgcccagc gcgtcgtcgg agccacccag tggctccgcg ccaacggcaa gctcggcgtc     960
ctcggcgagt tcgccggcgg cgccaacgcc gtctgccagc aggccgtcac cggcctcctc    1020
gaccacctcc aggacaacag cgacgtctgg ctgggtgccc tctggtgggc cgccggtccc    1080
tggtggggcg actacatgta ctcgttcgag cctccttcgg gcaccggcta tgtcaactac    1140
aactcgatcc taaagaagta cttgccg                                        1167
```

<210> SEQ ID NO 28
<211> LENGTH: 281
<212> TYPE: PRT
<213> ORGANISM: Artificial Sequence
<220> FEATURE:
<223> OTHER INFORMATION: Polypeptide

<400> SEQUENCE: 28

Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

```
Ile Lys Thr Glu Glu Asp Pro Ile Ile Lys Gln Asp Thr Pro Ser Asn
 50                  55                  60

Leu Asp Phe Asp Phe Ala Leu Pro Gln Thr Ala Thr Ala Pro Asp Ala
 65                  70                  75                  80

Lys Thr Val Leu Pro Ile Pro Glu Leu Asp Asp Ala Val Val Glu Ser
                 85                  90                  95

Phe Phe Ser Ser Ser Thr Asp Ser Thr Pro Met Phe Glu Tyr Glu Asn
             100                 105                 110

Leu Glu Asp Asn Ser Lys Glu Trp Thr Ser Leu Phe Asp Asn Asp Ile
         115                 120                 125

Pro Val Thr Thr Asp Asp Val Ser Leu Ala Asp Lys Ala Ile Glu Ser
     130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Lys Ser His His Val
            180                 185                 190

Gly Lys Asp Asp Glu Ser Arg Leu Asp His Leu Gly Val Val Ala Tyr
        195                 200                 205

Asn Arg Lys Gln Arg Ser Ile Pro Leu Ser Pro Ile Val Pro Glu Ser
210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                245                 250                 255

Val Glu Glu Leu Leu Ser Lys Asn Tyr His Leu Glu Asn Glu Val Ala
            260                 265                 270

Arg Leu Lys Lys Leu Val Gly Glu Arg
        275                 280

<210> SEQ ID NO 29
<211> LENGTH: 27
<212> TYPE: PRT
<213> ORGANISM: Artificial Sequence
<220> FEATURE:
<223> OTHER INFORMATION: Peptide

<400> SEQUENCE: 29

Gly Tyr Ile Pro Glu Ala Pro Arg Asp Gly Gln Ala Tyr Val Arg Lys
1               5                  10                  15

Asp Gly Glu Trp Val Leu Leu Ser Thr Phe Leu
            20                  25

<210> SEQ ID NO 30
<211> LENGTH: 85
<212> TYPE: PRT
<213> ORGANISM: Artificial Sequence
<220> FEATURE:
<223> OTHER INFORMATION: Polynucleotide

<400> SEQUENCE: 30

Gly Gly Cys Thr Ala Cys Ala Thr Cys Cys Cys Gly Ala Gly Gly
1               5                  10                  15

Cys Cys Cys Cys Cys Gly Cys Gly Ala Cys Gly Gly Cys Cys Ala
            20                  25                  30

Gly Gly Cys Cys Thr Ala Cys Gly Thr Cys Cys Gly Cys Ala Ala Gly
```

```
                    35                  40                  45
Gly Ala Cys Gly Gly Cys Gly Ala Gly Thr Gly Gly Gly Thr Cys Cys
            50                  55                  60

Thr Cys Cys Thr Cys Ala Gly Cys Ala Cys Cys Thr Thr Cys Cys Thr
65                  70                  75                  80

Gly Thr Gly Ala Gly
                85

<210> SEQ ID NO 31
<211> LENGTH: 5
<212> TYPE: PRT
<213> ORGANISM: Artificial Sequence
<220> FEATURE:
<223> OTHER INFORMATION: Peptide

<400> SEQUENCE: 31

Val Ile Ser Lys Arg
1               5

<210> SEQ ID NO 32
<211> LENGTH: 8
<212> TYPE: PRT
<213> ORGANISM: Artificial Sequence
<220> FEATURE:
<223> OTHER INFORMATION: Peptide

<400> SEQUENCE: 32

Asp Tyr Lys Asp Asp Asp Asp Lys
1               5
```